United States Patent
Wagers et al.

(10) Patent No.: US 12,415,001 B2
(45) Date of Patent: Sep. 16, 2025

(54) RNA-GUIDED SYSTEMS FOR IN VIVO GENE EDITING

(71) Applicant: President and Fellows of Harvard College, Cambridge, MA (US)

(72) Inventors: Amy J. Wagers, Cambridge, MA (US); Mohammadsharif Tabebordbar, Cambridge, MA (US); Wei Leong Chew, Boston, MA (US); George M. Church, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 188 days.

(21) Appl. No.: 18/145,996

(22) Filed: Dec. 23, 2022

(65) Prior Publication Data

US 2023/0211016 A1    Jul. 6, 2023

Related U.S. Application Data

(63) Continuation of application No. 16/834,339, filed on Mar. 30, 2020, now Pat. No. 11,666,665, which is a continuation of application No. 15/531,751, filed as application No. PCT/US2015/063181 on Dec. 1, 2015, now abandoned.

(Continued)

(51) Int. Cl.
| | |
|---|---|
| *A61K 48/00* | (2006.01) |
| *C12N 9/22* | (2006.01) |
| *C12N 15/10* | (2006.01) |
| *C12N 15/11* | (2006.01) |
| *C12N 15/86* | (2006.01) |
| *C12N 15/90* | (2006.01) |

(52) U.S. Cl.
CPC .............. *A61K 48/005* (2013.01); *C12N 9/22* (2013.01); *C12N 15/102* (2013.01); *C12N 15/11* (2013.01); *C12N 15/86* (2013.01); *C12N 15/907* (2013.01); *C12N 2310/20* (2017.05); *C12N 2750/14143* (2013.01)

(58) Field of Classification Search
CPC .......... A61K 48/00; A61K 48/05; C12N 9/22; C12N 15/11; C12N 15/86; C12N 15/102; C12N 15/907; C12N 2310/20
See application file for complete search history.

(56) References Cited

U.S. PATENT DOCUMENTS

| | | |
|---|---|---|
| 7,973,015 B2 | 7/2011 | van Ommen et al. |
| 2012/0196370 A1 | 8/2012 | Urnov et al. |

(Continued)

FOREIGN PATENT DOCUMENTS

| | | |
|---|---|---|
| WO | 2014/186585 A2 | 11/2014 |
| WO | 2014/197748 A2 | 12/2014 |

(Continued)

OTHER PUBLICATIONS

Mali et al, Science 339: 823-826, Feb. 15, 2013; 41 pages total, including Supplementary materials.*

(Continued)

*Primary Examiner* — Kevin K Hill
(74) *Attorney, Agent, or Firm* — Banner & Witcoff, Ltd.

(57) ABSTRACT

Methods of editing target nucleic acids are provided using a guide RNA and a Cas9 protein to excise exons in a target gene and where the edited gene is expressed to produce a truncated polypeptide.

16 Claims, 50 Drawing Sheets
Specification includes a Sequence Listing.

Mouse DMD exon 52 + 53 can be removed by CRISPR double cut

Related U.S. Application Data

(60) Provisional application No. 62/085,785, filed on Dec. 1, 2014.

(56) References Cited

U.S. PATENT DOCUMENTS

| | | | |
|---|---|---|---|
| 2014/0140969 A1 | 5/2014 | Beausejour et al. | |
| 2014/0242664 A1 | 8/2014 | Zhang et al. | |
| 2016/0058889 A1* | 3/2016 | Olson | A61K 48/0058 424/94.6 |
| 2016/0312198 A1* | 10/2016 | Joung | C12N 15/111 |

FOREIGN PATENT DOCUMENTS

| | | | |
|---|---|---|---|
| WO | WO 14/197748 | * | 12/2014 |
| WO | 2015/138739 A2 | | 9/2015 |
| WO | WO 15/138739 | * | 9/2015 |
| WO | 2016/161380 A1 | | 10/2016 |

OTHER PUBLICATIONS

Flanking definition, www.merriam-webster.com/dictionary/flank; last visited Mar. 26, 2025.*

Long et al. "Prevention of muscular dystrophy in mice by CRISPR/Cas9-mediated editing of germline DNA," SCIENCE ePub Aug. 14, 2014 vol. 345 No. 6201 pp. 1184-1188.

Aartsma-Rus et al. "Theoretic Applicability of Antisense-Mediated Exon Skipping for Duchenne Muscular Dystrophy Mutations" Human Mutation; vol. 30; No. 3, pp. 293-299; Mar. 2009.

Dunckley et al. "Modification of splicing in the dystrophin gene in cultured Mdx muscle cells by antisense oligoribonucleotides" Human Molecular Genetics; vol. 5; No. 1; pp. 1083-1090; Jul. 1998.

Wilton et al. "Specific removal of the nonsense mutation from the mdx dystrophin mRNA using antisense bligonucleotides" Neuromuscular Disorders; vol. 9; No. 5; pp. 330-338; Jul. 1999.

Sakuma et al. "Multiplex genome engineering in human cells using all-in-one CRISPR/Cas9 vector system" Scientific Reports; vol. 4; Article No. 5400; doi.org/10.1038/srep05400; 6 pages; available online Jun. 23, 2014.

Martz "A CRISPR possibility for DMD" Science-Business exchange; vol. 7; No. 1115; 2 pages; doi/org/10.1038/scibx.2014.1115, available online Oct. 2, 2014.

Oct. 5, 2022—(US) Non Final Office Action—U.S. Appl. No. 16/834,338.

Mali et al. "RNA-Guided Human Genome Engineering via Cas9" Science; Feb. 15, 2013; vol. 339; Issue 6121; pp. 823-826 and Supplementary Materials pp. 1-36.

* cited by examiner

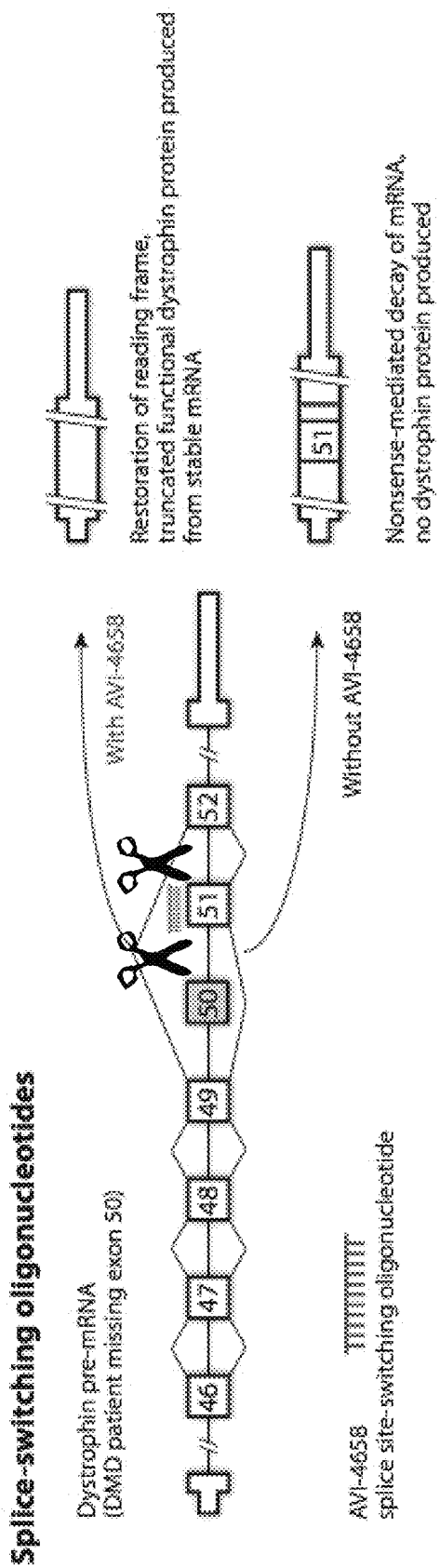

Mouse DMD exon 23 can be removed by CRISPR double cut in C2C12 myoblasts

Genomic DNA PCR

Mouse DMD exon 23 can be skipped at the mRNA level by CRISPR double cut in C2C12 myoblasts Mouse DMD exon 23 can be removed by CRISPR double cut in mdx muscle fibers

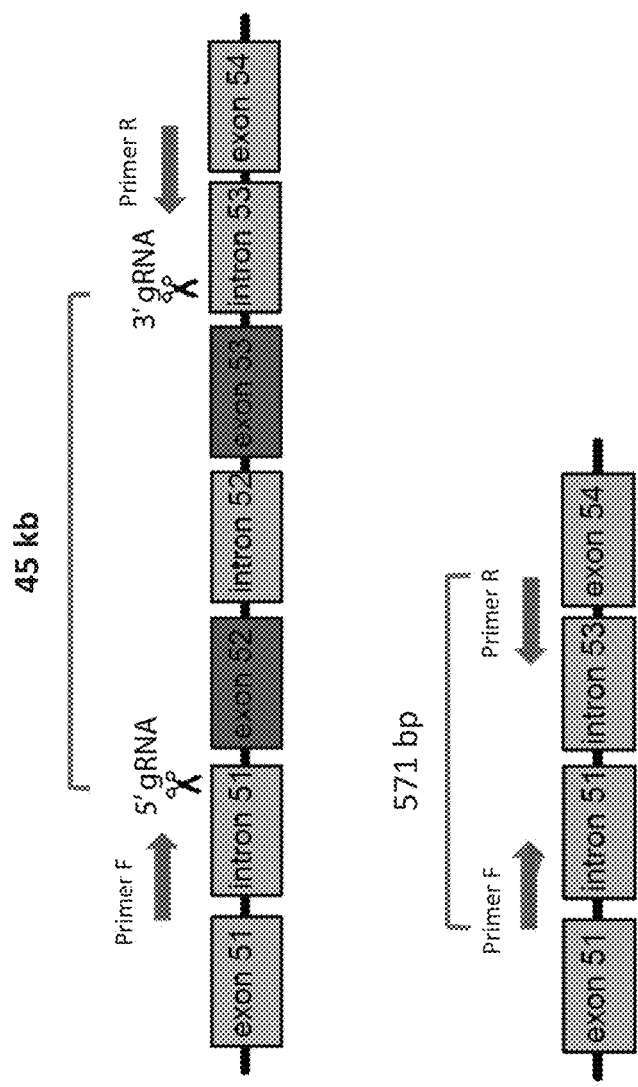
Figure 5A. Mouse DMD exon 52 + 53 can be removed by CRISPR double cut

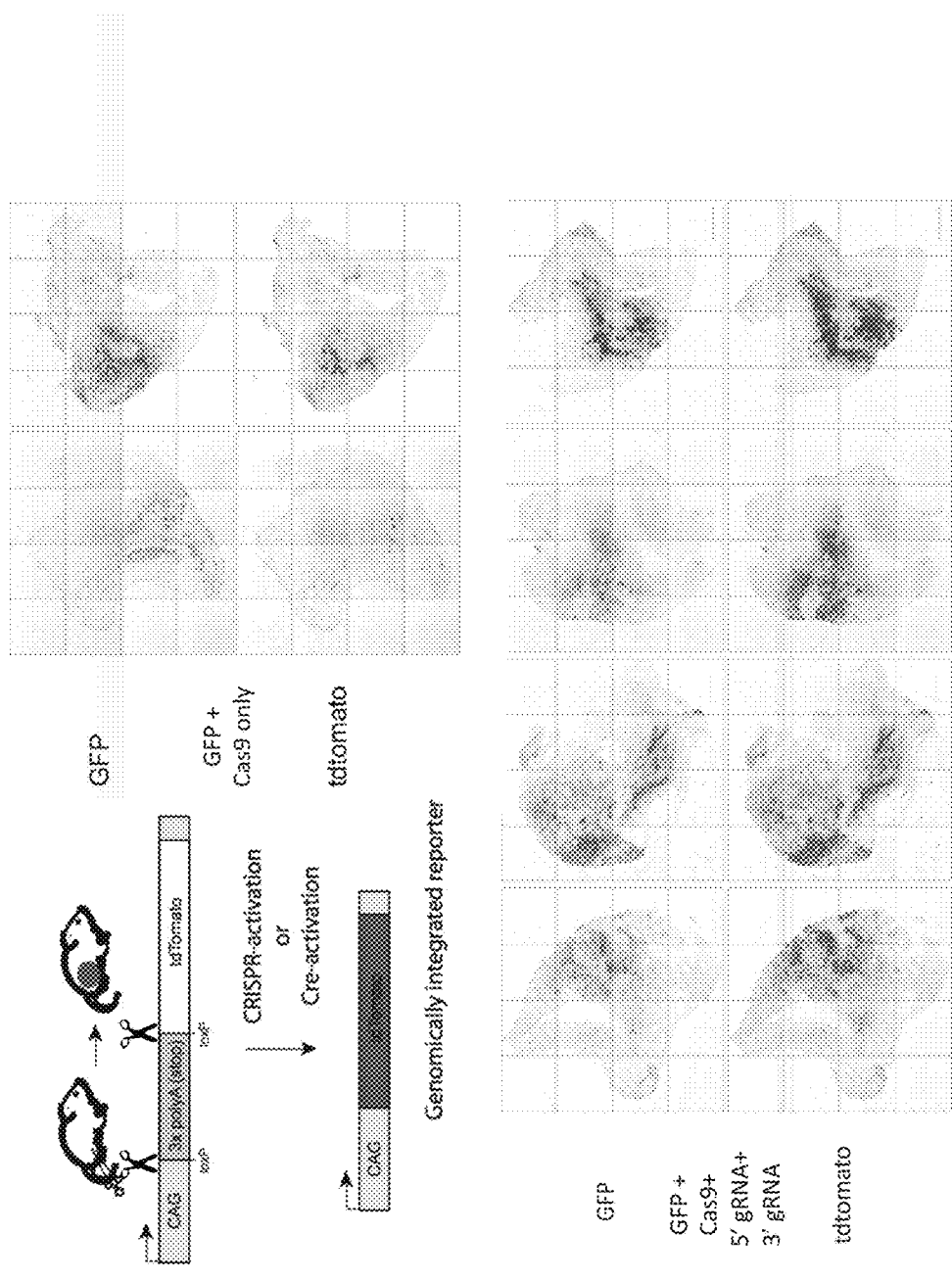

A multiplex-able reporter system for detecting CRISPR *in vivo* activity

Figure 8
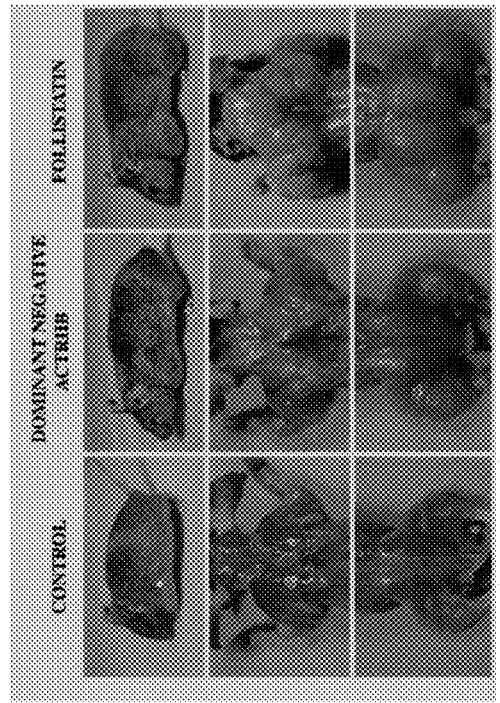
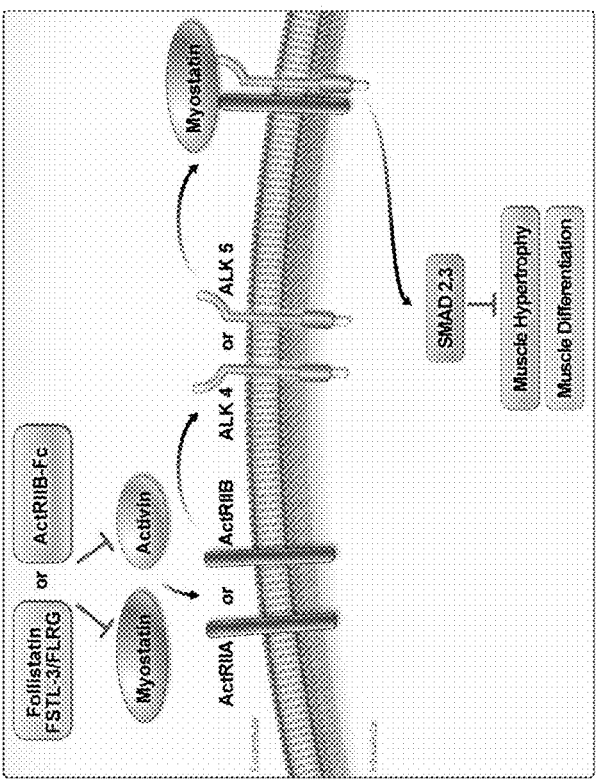
Lee and Glass Skeletal Muscle 2011
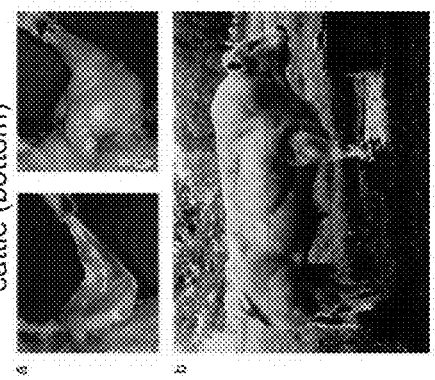
Mstn null mouse (top right) and cattle (bottom)
Se-Jin Lee, Annu. Rev. Cell Dev. Biol. 2004

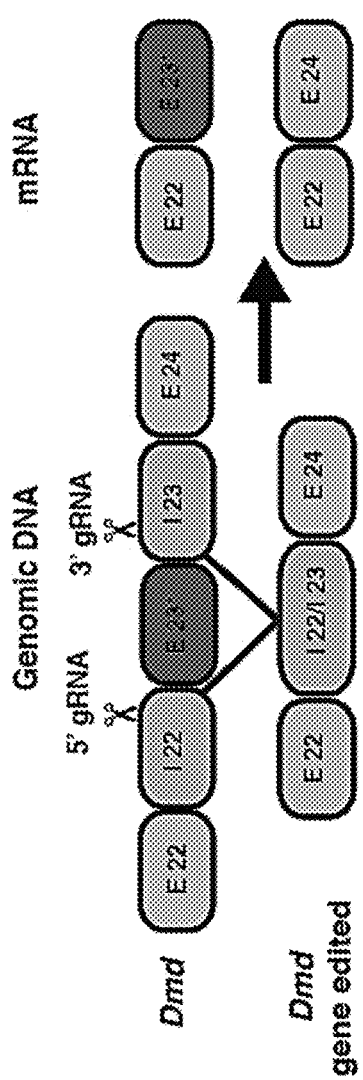
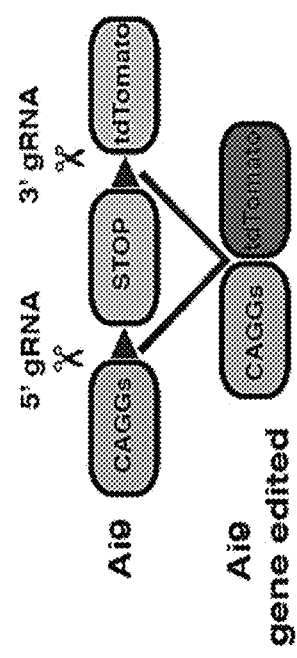

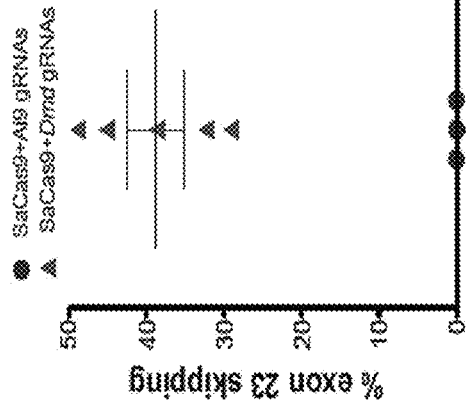
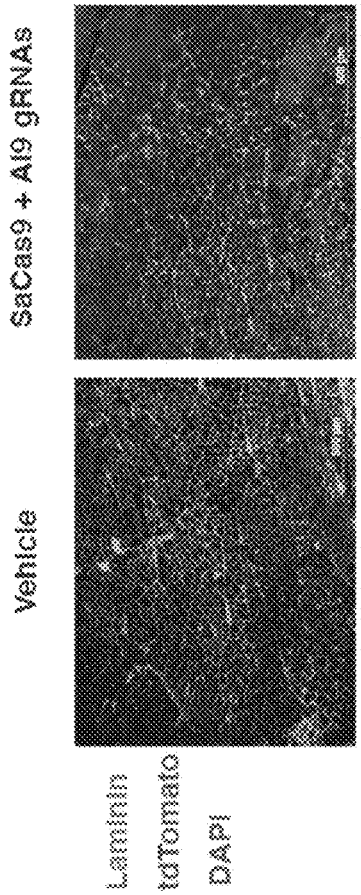
Figure 15A
Figure 15B
Figure 15C
Figure 15D

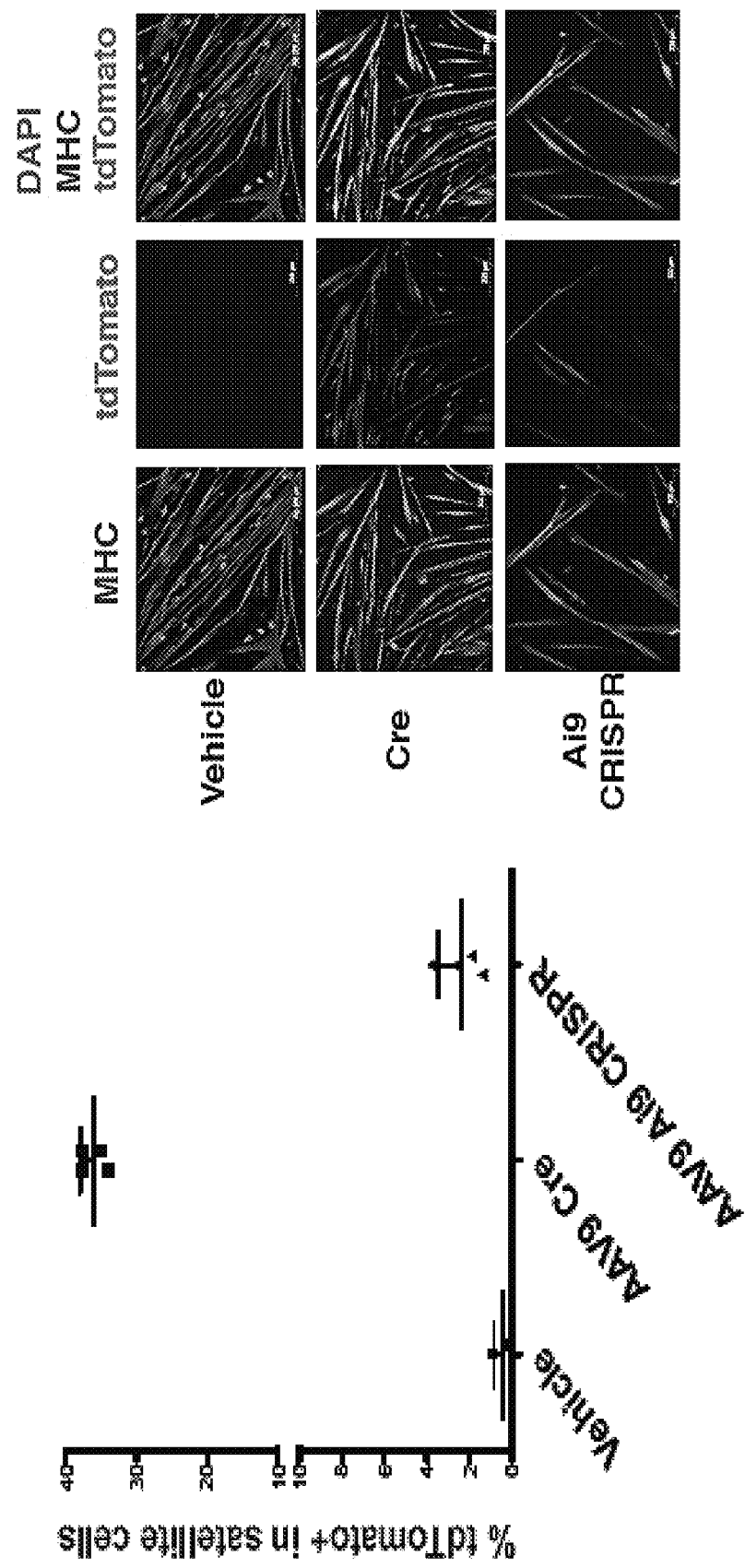

RNA-GUIDED SYSTEMS FOR IN VIVO GENE EDITING

RELATED APPLICATION DATA

This application is a continuation application which claims priority to U.S. patent application Ser. No. 16/834,339, filed Mar. 30, 2020, which is a continuation application which claims priority to U.S. patent application Ser. No. 15/531,751, filed May 31, 2017, which is a National Stage Application under 35 U.S.C. 371 of PCT application PCT/US15/63181 designating the United States and filed Dec. 1, 2015; which claims the benefit of U.S. provisional application No. 62/085,785, filed Dec. 1, 2014 which are hereby incorporated herein by reference in its entirety for all purposes.

STATEMENT OF GOVERNMENT INTERESTS

This invention was made with government support under HG005550, EY018244, HL100402, and OD004345 awarded by the National Institutes of Health. The government has certain rights in the invention.

SEQUENCE LISTING

The instant application contains a Sequence Listing which has been submitted electronically in XML format and is hereby incorporated by reference in its entirety. Said XML copy, created on Dec. 14, 2022, is named "Sequence_Listing_010498_01359_ST26" and is 47 KB in size.

BACKGROUND

Bacterial and archaeal CRISPR-Cas systems rely on short guide RNAs (gRNA) in complex with Cas proteins to direct degradation of complementary sequences present within invading foreign nucleic acid. See Deltcheva, E. et al. CRISPR RNA maturation by trans-encoded small RNA and host factor RNase III. *Nature* 471, 602-607 (2011); Gasiunas, G., Barrangou, R., Horvath, P. & Siksnys, V. Cas9-crRNA ribonucleoprotein complex mediates specific DNA cleavage for adaptive immunity in bacteria. *Proceedings of the National Academy of Sciences of the United States of America* 109, E2579-2586 (2012); Jinek, M. et al. A programmable dual-RNA-guided DNA endonuclease in adaptive bacterial immunity. *Science* 337, 816-821 (2012); Sapranauskas, R. et al. The *Streptococcus thermophilus* CRISPR/Cas system provides immunity in *Escherichia coli*. *Nucleic acids research* 39, 9275-9282 (2011); and Bhaya, D., Davison, M. & Barrangou, R. CRISPR-Cas systems in bacteria and archaea: versatile small RNAs for adaptive defense and regulation. *Annual review of genetics* 45, 273-297 (2011). A recent in vitro reconstitution of the *S. pyogenes* type II CRISPR system demonstrated that crRNA ("CRISPR RNA") fused to a normally trans-encoded tracrRNA ("trans-activating CRISPR RNA") is sufficient to direct Cas9 protein to sequence-specifically cleave target DNA sequences matching the crRNA. Expressing a gRNA with a 'spacer' homologous to a target site results in Cas9 recruitment and endonucleolytic cleavage of the target DNA protospacer. See H. Deveau et al., Phage response to CRISPR-encoded resistance in *Streptococcus thermophilus*. *Journal of Bacteriology* 190, 1390 (February 2008). Various uses of CRISPR/Cas9 systems are known. See WO2014/099744, WO2013176772, U.S. Pat. No. 8,697,359 and Sternberg et al., *Nature*, Vol. 507, pp. 62-67 (2014).

Duchenne muscular dystrophy (DMD) is one of the most common X-linked genetic disorders in humans, and arises from mutations in the Dystrophin gene that cause loss of protein expression (see A. H. Burghes, C. Logan, X. Hu, B. Belfall, R. G. Worton, P. N. Ray, A cDNA clone from the Duchenne/Becker muscular dystrophy gene. *Nature* 328, 434-437 (1987)). Dystrophin is an essential structural protein in muscle fibers, J. M. Ervasti, K. P. Campbell, Membrane organization of the dystrophin-glycoprotein complex. *Cell* 66, 1121-1131 (1991), and its absence destabilizes the muscle fiber membrane, increasing the susceptibility of muscle fibers to contraction-induced injury, K. P. Campbell, S. D. Kahl, Association of dystrophin and an integral membrane glycoprotein. *Nature* 338, 259-262 (1989), which eventually leads to loss of mobility and premature death in patients.

SUMMARY

Aspects of the present disclosure are directed to a method of altering the sequence of a full length biologically active polypeptide to produce an altered biologically active polypeptide. The gene encoding the full length biologically active polypeptide is altered to remove sequences encoding for portions of the biologically active polypeptide that do not prevent the biological activity of the polypeptide, or otherwise allow the altered or modified polypeptide to have an activity similar to the full length or unmodified polypeptide. According to one aspect, the gene is altered using a DNA binding protein, such as a Cas9 protein. According to one aspect, the gene is altered using a CRISPR/Cas9 system. According to one aspect, the gene is altered using a CRISPR/Cas9 system in vivo. According to one aspect, a CRISPR/Cas9 system is delivered into a cell where the CRISPR/Cas9 system cuts the target gene to remove sequences encoding for portions of the biologically active polypeptide that do not prevent the biological activity of the polypeptide. In this manner, the altered or modified or truncated polypeptide has an activity the same as or similar to that of the full length, unaltered, unmodified or non-truncated polypeptide. According to one aspect, the cell may be a cell in a cell culture, an embryonic cell or a cell in an animal that is post embryonic stage, such as a mature animal. Accordingly, aspects of the present disclose include carrying out the methods described herein in vivo in an animal. According to one aspect, the altered gene is expressed to produce an altered biologically active polypeptide which may be referred to herein as a truncated biologically active polypeptide. The biologically active polypeptide is truncated to the extent that it lacks one or more sequences found in the full length polypeptide. The polypeptide is "truncated" to the extent that the truncated polypeptide excludes amino acid sequences that are present in the full length or non-truncated polypeptide. A truncated biologically active polypeptide lacks one or more sequences found in the full length polypeptide yet retains the same or substantially similar or similar biological activity of the full length polypeptide. In this aspect, the biological activity of the full length polypeptide is retained in the truncated biologically active polypeptide despite having one or more portions of the polypeptide removed. In another aspect, the biological activity may be altered by the modification of one or more sequences in the truncated biologically active polypeptide. For example, the modification may result in a partially active protein or a dominant negative protein.

Aspects of the present disclosure are directed to a method of genetically altering a nucleic acid sequence, such as a target gene, to excise one or more nucleic acid portions or sections or sequences of the gene encoding a biologically functional polypeptide using a CRISPR/Cas9 system. According to certain aspects, the CRISPR Cas9 system includes a Cas9 protein and two or more guide RNA. The two or more guide RNA are complementary to corresponding target nucleic acid sequences on either side of, i.e. flanking, the nucleic acid portion or section or sequence of the target gene to be excised or removed. The guide RNA bind to the corresponding target nucleic acid sequences and the Cas9 protein cuts the double stranded nucleic acid at two or more cut sites flanking the one or more nucleic acid portions or sections or sequences thereby excising or removing the one or more nucleic acid portions or sections or sequences. The gene having two or more cut sites recombines to form an altered gene with the one or more nucleic acid portions or sections or sequences being absent. The gene is referred to herein as an altered target gene, which may also be referred to as a modified target gene or truncated target gene. The altered target gene is then expressed to produce an altered biologically functional polypeptide, which may retain full or partial biological activity, or may exhibit loss of function or dominant inhibitory activity.

According to one aspect, the method is carried out within a cell, i.e. in vivo. The cell can be a eukaryotic cell. According to one aspect, the nucleic acid portion is a target excision sequence and the two or more guide RNAs are complementary to flanking sequences on either side of the target excision sequence. According to one aspect, the target excision sequence includes one or more exons in the target gene encoding a biologically functional polypeptide. According to one aspect, the two or more guide RNAs bind to complementary target genomic DNA sequences and the Cas9 protein cleaves the two or more target genomic DNA sequences thereby removing the one or more exons from the target gene to produce an altered target gene. According to one aspect, the altered target gene recombines. According to one aspect, the altered target gene recombines at a reading frame in the target gene. The cell expresses the altered target gene which has recombined to produce a biologically functional polypeptide which is truncated compared to the full length polypeptide. According to one aspect, the cell expresses the altered and recombined target gene to produce an altered biologically functional polypeptide. According to one aspect, the altered biologically functional polypeptide is truncated relative to the full length biologically functional polypeptide.

According to methods described herein, a complex is formed including a guide RNA, a DNA binding protein, such as a Cas9 protein, and a double stranded DNA target sequence. According to certain aspects, DNA binding proteins within the scope of the present disclosure include a protein that forms a complex with the guide RNA and with the guide RNA and or the complex binding to a double stranded DNA sequence. This aspect of the present disclosure may be referred to as co-localization of the RNA and DNA binding protein to or with the double stranded DNA. In this manner, a DNA binding protein-guide RNA complex may be used to cut DNA at a specific target DNA sequence.

According to certain aspects, the term "guide RNA" in the context of a CRISPR Cas9 system is known to those of skill in the art and includes a portion, such as a 20 nucleotide spacer portion, that is complementary to a target nucleic acid protospacer. Methods of designing guide RNA are well known to those of skill in the art. Methods described herein include contacting the target nucleic acid sequence with a plurality of guide RNA sequences, each having a portion complementary to the target nucleic acid sequence.

According to one aspect, the target nucleic acid is a double stranded nucleic acid. According to one aspect, the target nucleic acid is double stranded genomic DNA. According to one aspect, the target nucleic acid is chromosomal DNA. According to one aspect, the target nucleic acid is RNA.

According to one aspect, the Cas9 protein is wild type Cas9, a Cas9 nickase or a nuclease null Cas9, as known to those of skill in the art. According to one aspect, the nuclease null Cas9 excludes one or more nucleases. Methods of isolating wild type Cas9 are known to those of skill in the art. Methods of making a Cas9 nickase are known to those of skill in the art. Methods of making a nuclease null Cas9 are known to those of skill in the art.

According to one aspect, the cell is a eukaryotic cell. According to one aspect, the cell is a yeast cell, a plant cell, a vertebrate cell, or an animal cell, such as an adult animal cell. According to one aspect, the cell is a mammalian cell. According to one aspect, the cell is a human cell.

According to one aspect, the guide RNA is between about 10 to about 500 nucleotides. According to one aspect, the guide RNA is between about 20 to about 100 nucleotides. According to one aspect, a scaffold for the guide RNA is between about 80 to about 95 nucleotides and is fused to a variable spacer sequence between about 16 to about 40 nucleotides. According to one aspect, the guide RNA is a tracrRNA-crRNA fusion.

According to one aspect, a method of producing an altered gene product in a eukaryotic cell includes the steps of providing to the cell two or more guide RNAs and a Cas9 protein, wherein the two or more guide RNAs are complementary to two or more target genomic DNA sequences flanking a target excision sequence including one or more exons in a target gene encoding a biologically functional polypeptide, wherein the two or more guide RNAs bind to the two or more complementary target genomic DNA sequences and the Cas9 protein cleaves the two or more target genomic DNA sequences thereby removing the one or more exons from the target gene to produce an altered target gene, and wherein the altered target gene recombines in the target gene, and wherein the eukaryotic cell expresses the altered target gene to produce an altered biologically functional polypeptide.

According to one aspect, the altered target gene recombines at a reading frame in the target gene. According to one aspect, the altered target gene recombines at a shifted reading frame in the target gene, such as a frameshift downstream of the excision.

According to one aspect, an altered biologically functional polypeptide lacks a polypeptide sequence corresponding to the one or more exons removed from the target gene.

According to one aspect, the two or more guide RNAs and the Cas9 protein are foreign to the eukaryotic cell. According to one aspect, the two or more guide RNAs and the Cas9 protein are foreign to each other. According to one aspect, the two or more guide RNAs and the Cas9 protein are non-naturally occurring.

According to one aspect, the two or more guide RNAs and the Cas9 protein are provided to a cell using methods known to those of skill in the art. According to one aspect, the two or more guide RNAs are provided to the cell by electroporation of the two or more guide RNAs into the cell. According to one aspect, the Cas9 protein is provided to the cell by electroporation of the Cas9 protein into the cell. According to one aspect, the Cas9 protein is provided to the cell by liposomal encapsulation, such as by lipofection. According to one aspect, the Cas9 protein is provided to the cell by viral delivery, such as by lentivirus, adenovirus, adeno-associated virus, retrovirus, herpes simplex virus, or sendai virus.

According to one aspect, the two or more guide RNAs are provided to the cell by introducing into the cell a first foreign nucleic acid sequence encoding the two or more guide RNAs, wherein the first foreign nucleic acid is expressed. According to one aspect, the two or more guide RNAs are provided to the cell by introducing into the cell a first foreign nucleic acid sequence encoding the two or more guide RNAs present in a vector wherein the first foreign nucleic acid is expressed.

According to one aspect, the Cas 9 protein is provided to the cell by introducing into the cell a second foreign nucleic acid sequence encoding the Cas 9 protein wherein the second foreign nucleic acid sequence is expressed.

According to one aspect, the Cas 9 protein is provided to the cell by introducing into the cell a second foreign nucleic acid sequence encoding the Cas 9 protein present in a vector wherein the second foreign nucleic acid sequence is expressed.

According to one aspect, the eukaryotic cell is a yeast cell, a plant cell, a vertebrate cell, a mammalian cell (e.g., a human cell), or a non-mammalian cell (e.g., a fish cell, bird cell). According to one aspect, the eukaryotic cell is within a mammal According to one aspect, the eukaryotic cell is a skeletal muscle cell or a cardiac muscle cell.

According to one aspect, the target excision sequence is greater than 45 kb. According to one aspect, the target gene encodes dystrophin protein. According to one aspect, the target gene encodes dystrophin protein, and the one or more exons is exon 23. According to one aspect, the target gene encodes dystrophin protein, and the one or more exons is exon 52 and exon 53. According to one aspect, the one or more exons are in the exon 45-55 region.

According to one aspect, the guide RNA includes between about 10 to about 250 nucleotides. According to one aspect, the guide RNA includes between about 20 to about 100 nucleotides. According to one aspect, the guide RNA includes a guide sequence fused to a trans-activating cr (tracr) sequence.

According to one aspect, the ratio range of plasmid encoding the Cas9 protein to the plasmid encoding the guide RNA is between 1:10 and 10:1. An exemplary ratio range of plasmid encoding the Cas9 protein to the plasmid encoding the guide RNA is between 1:5 and 2:1. One of skill in the art would readily understand based on the present disclosure that any particular ratio depends on at least cell type. According to one aspect, the plasmid encoding the guide RNA is modified to increase the expression of the RNA by removing a potential premature transcription termination site.

According to one aspect, the one or more exons include a mutation. According to one aspect, the Cas9 protein is provided to the cell by electroporation of the Cas9 mRNA into the cell, by liposomal encapsulation, or by viral delivery. According to one aspect, the guide RNA and the Cas9 protein co-localize to the target genomic DNA sequence to form a complex.

According to one aspect, the guide RNA and the Cas9 protein are combined and then contacted with the target gene. According to one aspect, the guide RNA and the Cas9 protein are combined and then contacted with the target gene within a cell.

According to one aspect, a plurality of guide RNAs with each having a portion complementary to a target genomic DNA sequence are provided to the cell.

Further features and advantages of certain embodiments of the present invention will become more fully apparent in the following description of embodiments and drawings thereof, and from the claims.

BRIEF DESCRIPTION OF THE DRAWINGS

The foregoing and other features and advantages of the present invention will be more fully understood from the following detailed description of illustrative embodiments taken in conjunction with the accompanying drawings in which:

FIG. 1 is a schematic diagram of the Dystrophin pre-mRNA of a Duchenne Patient with exon 50 deletion. Skipping exon 51 at the mRNA level leads to restoration of reading frame and production of a truncated but partially functional Dystrophin protein. Exon skipping can be caused by antisense oligonucleotides at the RNA splicing stage, which needs repeated administration of high doses of the oligonucleotide, or by a one-time deletion of exon 51 from the genomic DNA using a CRISPR Cas9 system.

FIG. 5A is a schematic diagram of the mdx4cv mouse genomic DNA at the mutated exon 53 locus before (top) and after (bottom) cutting the DNA with two gRNAs targeting 5' of exon 52 and 3' of exon 53. Deletion of exons 52 and 53 from the DNA and skipping these exons in the mRNA restores the reading frames and leads to expression of a truncated but functional protein in mdx4cv mouse muscle (see Mitrpant et. al, By-passing the nonsense mutation in the 4 CV mouse model of muscular dystrophy by induced exon skipping, J Gene Med. 2009 January; 11(1):46-56).

FIG. 6A is a schematic diagram of an in vivo CRISPR activity reporter system in mouse muscle, wherein the mouse strain was obtained from the Jackson Library (stock number 007905, world wide website jaxmice.jax.org/strain/007905.html). The Ai9 reporter construct integrated into the mouse Rosa26 locus contains a 3×STOP cassette between the promoter and the tdtomato coding sequence, which upon excision of the 3×STOP cassette by cutting with two gRNAs at 5' and 3' sites of the cassette (or by Cre-mediated excision), expresses tdTomato under the control of a CAG promoter.

FIG. 6B illustrates pictures of Ai9 muscle sections electroporated with GFP and Cas9 only (top), or GFP, Cas9 and two gRNAs targeting 5' and 3' of the STOP cassette (bottom).

FIG. 8 is a diagram illustrating muscle hypertrophy induced by a non-functional myostatin-activin receptor pathway.

FIG. 14A is a schematic of the Ai9 allele used for tdTomato fluorescent reporting of gene editing in CRISPR transduced cells. Precise excision of the 3×STOP cassette induced by paired CRISPR targeting enables tdTomato expression from the ubiquitous CAGGs promoter.

FIG. 14B is a schematic of CRISPR-mediated excision of DMD exon 23, which in mdx mice bears a nonsense mutation (E23*) that results in destabilization of DMD mRNA and absence of Dystrophin expression in muscle. Targeted excision of E23* creates a hybrid intron (122/23), and subsequent transcription and splicing generates an exon "skipped" mRNA in which exon 22 (E22) is fused directly to exon 24 (E24), restoring Dystrophin reading frame and producing a truncated but still functional Dystrophin protein.

FIG. 14C is a schematic of the Ai9 targeting gRNA constructs.

FIG. 14D is a schematic of the coupled Ai9-DMD23 gRNA constructs.

FIG. 15A is representative immunofluorescence analysis of muscles from adult mdx;Ai9 mice injected intramuscularly with vehicle (left) or dual AAVs encoding for SaCas9 and Ai9 gRNAs (right). The dual AAV-CRISPR system efficiently targets the Ai9 locus in adult dystrophic muscle, resulting in tdTomato expression (red). Individual muscle fibers are marked by laminin (green), and nuclei by DAPI (blue). Scale bar: 500 um.

FIG. 15B depicts the detection of permanent exon skipping by genomic PCR using primers spanning DMD exon 23 (left). DNA was isolated from tibialis anterior muscle harvested from mdx;Ai9 mice injected intramuscularly with AAV-CRISPR targeting the Ai9 or DMD23 locus. Exon 23 excision in DNA is detected only in muscles receiving AAV-DMD23 gRNAs. Sanger sequencing trace confirms precise deletion of exon 23 from the genome (right). (SEQ ID NO:4)

FIG. 15C depicts the detection of exon skipping in the mRNA by RT-PCR (left). Sequencing result from unedited and exon skipped mRNA, confirms skipping of exon 23 in the mRNA (right). (SEQ ID NO:5-6)

FIG. 15D graphically depicts the quantification of exon skipping in injected muscles by Taqman-based real time PCR. Data plotted for individual mice (n=5 receiving DMD23 gRNAs (blue) and n=3 receiving Ai9 gRNAs (red). Overlay indicates mean+/−SD for Sa Cas9+DMD gRNA group.

FIG. 17C graphically depicts the quantification of tdTomato+ cells among ZsGreen+ satellite cells isolated from mice injected intramuscularly with vehicle, AAV9-Cre or AAV9-Ai9 CRISPR.

FIG. 17D depicts the representative immunofluorescence images of myotubes differentiated from FACSorted Pax7-ZsGreen+ cells from vehicle (top), AAV9-Cre (middle) and AAV9-Ai9 CRISPR (bottom) injected muscles. Myosin heavy chain (MHC, green); tdTomato (red). Scale bar: 200 um.

DETAILED DESCRIPTION

Figure 2A:
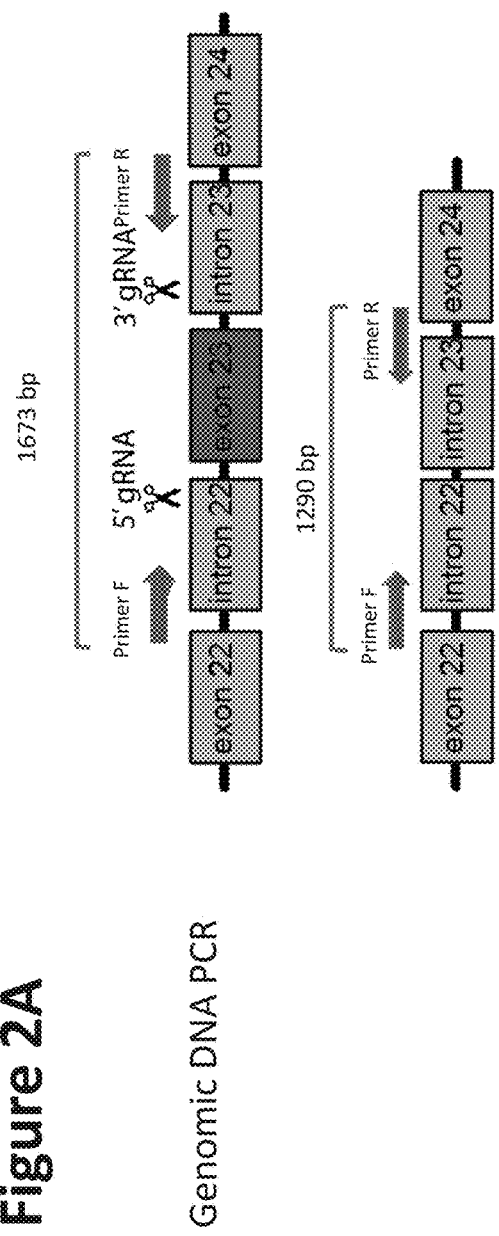
FIG. 2A is a schematic diagram of the mdx mouse genomic DNA at the mutated exon 23 locus before (top) and after (bottom) cutting the DNA with two gRNAs targeting 5' and 3' of exon 23.

Embodiments of the present disclosure are based on the use of DNA binding proteins and guide RNA to co-localize at or complex at a target nucleic acid and then cut or cleave the target nucleic acid in a manner to remove a nucleic acid sequence, which may be referred to herein as an excision sequence. Such DNA binding proteins include RNA-guided DNA binding proteins readily known to those of skill in the art to bind to DNA for various purposes. Such DNA binding proteins may be naturally occurring. DNA binding proteins included within the scope of the present disclosure include those which may be guided by RNA, referred to herein as guide RNA. According to this aspect, the guide RNA and the RNA guided DNA binding protein form a co-localization complex at the DNA. According to certain aspects, the DNA binding protein may be a nuclease-null DNA binding protein which otherwise may have one or more nucleases attached thereto. According to this aspect, the nuclease-null DNA binding protein may result from the alteration or modification of a DNA binding protein having nuclease activity. Such DNA binding proteins having nuclease activity are known to those of skill in the art, and include naturally occurring DNA binding proteins having nuclease activity, such as Cas9 proteins present, for example, in Type II CRISPR systems. Such Cas9 proteins and Type II CRISPR systems are well documented in the art. See Makarova et al., *Nature Reviews, Microbiology*, Vol. 9, June 2011, pp. 467-477 including all supplementary information hereby incorporated by reference in its entirety.

In general, a CRISPR locus is characterized by an array of repetitive sequences (direct repeats) interspaced by short stretches of non-repetitive sequences (spacers). The non-coding CRISPR array is transcribed and cleaved within direct repeats into short crRNAs containing individual spacer sequences, which direct Cas nucleases to the target site (protospacer). The Type II CRISPR system carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer.

Exemplary DNA binding proteins having nuclease activity function to nick or cut double stranded DNA. Such nuclease activity may result from the DNA binding protein having one or more polypeptide sequences exhibiting nuclease activity. Such exemplary DNA binding proteins may have two separate nuclease domains with each domain responsible for cutting or nicking a particular strand of the double stranded DNA. Exemplary polypeptide sequences having nuclease activity known to those of skill in the art include the McrA-HNH nuclease related domain and the RuvC-like nuclease domain. Accordingly, exemplary DNA binding proteins are those that in nature contain one or more of the McrA-HNH nuclease related domain and the RuvC-like nuclease domain. According to certain aspects, the DNA binding protein is altered or otherwise modified to inactivate the nuclease activity. Such alteration or modification includes altering one or more amino acids to inactivate the nuclease activity or the nuclease domain Such modification includes removing the polypeptide sequence or polypeptide sequences exhibiting nuclease activity, i.e. the nuclease domain, such that the polypeptide sequence or polypeptide sequences exhibiting nuclease activity, i.e. nuclease domain, are absent from the DNA binding protein. Other modifications to inactivate nuclease activity will be readily apparent to one of skill in the art based on the present disclosure. Accordingly, a nuclease-null DNA binding protein includes polypeptide sequences modified to inactivate nuclease activity or removal of a polypeptide sequence or sequences to inactivate nuclease activity. The nuclease-null DNA binding protein retains the ability to bind to DNA even though the nuclease activity has been inactivated. When a nuclease null DNA binding protein is used, the nuclease null DNA binding protein has been modified to include one or more DNA nucleases, which may be more specific, such as Fok1, in cutting DNA than the nucleases associated with wild type Cas9. Accordingly, the DNA binding protein includes the polypeptide sequence or sequences required for DNA binding but may lack the one or more or all of the nuclease sequences exhibiting nuclease activity. Accordingly, the DNA binding protein includes the polypeptide sequence or sequences required for DNA binding but may have one or more or all of the nuclease sequences exhibiting nuclease activity inactivated.

According to one aspect, a DNA binding protein having two or more nuclease domains may be modified or altered to inactivate all but one of the nuclease domains. Such a modified or altered DNA binding protein is referred to as a DNA binding protein nickase, to the extent that the DNA binding protein cuts or nicks only one strand of double stranded DNA. When guided by RNA to DNA, the DNA binding protein nickase is referred to as an RNA guided DNA binding protein nickase. Accordingly, useful Cas9 proteins may be a wild type Cas9, a Cas9 nickase or a nuclease null Cas9 and homologs and orthologs thereof. See Jinek et al., Science 337, 816-821 (2012) hereby incorporated by reference in its entirety.

In S. pyogenes, Cas9 generates a blunt-ended double-stranded break 3 bp or 4 bp upstream of the protospacer-adjacent motif (PAM) via a process mediated by two catalytic domains in the protein: an HNH domain that cleaves the complementary strand of the DNA and a RuvC-like domain that cleaves the non-complementary strand. See Jinek et al., Science 337, 816-821 (2012) hereby incorporated by reference in its entirety. Cas9 proteins are known to exist in many Type II CRISPR systems including the following as identified in the supplementary information to Makarova et al., Nature Reviews, Microbiology, Vol. 9, June 2011, pp. 467-477: *Methanococcus maripaludis* C7; *Corynebacterium diphtheriae*; *Corynebacterium efficiens* YS-314; *Corynebacterium glutamicum* ATCC 13032 Kitasato; *Corynebacterium glutamicum* ATCC 13032 Bielefeld; *Corynebacterium glutamicum* R; *Corynebacterium kroppenstedtii* DSM 44385; *Mycobacterium abscessus* ATCC 19977; *Nocardia farcinica* IFM10152; *Rhodococcus erythropolis* PR4; *Rhodococcus jostii* RHA1; *Rhodococcus opacus* B4 uid36573; *Acidothermus cellulolyticus* 11B; *Arthrobacter chlorophenolicus* A6; *Kribbella flavida* DSM 17836 uid43465; *Thermomonospora curvata* DSM 43183; *Bifidobacterium dentium* Bd1; *Bifidobacterium longum* DJO10A; *Slackia heliotrinireducens* DSM 20476; *Persephonella marina* EX H1; *Bacteroides fragilis* NCTC 9434; *Capnocytophaga ochracea* DSM 7271; *Flavobacterium psychrophilum* JIP02 86; *Akkermansia muciniphila* ATCC BAA 835; *Roseiflexus castenholzii* DSM 13941; *Roseiflexus* RS1; *Synechocystis* PCC6803; *Elusimicrobium minutum* Pei191; uncultured Termite group 1 bacterium phylotype Rs D17; *Fibrobacter succinogenes* S85; *Bacillus cereus* ATCC 10987; *Listeria innocua*; *Lactobacillus casei*; *Lactobacillus rhamnosus* GG; *Lactobacillus salivarius* UCC118; *Streptococcus agalactiae* A909; *Streptococcus agalactiae* NEM316; *Streptococcus agalactiae* 2603; *Streptococcus dysgalactiae equisimilis* GGS 124; *Streptococcus equi zooepidemicus* MGCS10565; *Streptococcus gallolyticus* UCN34 uid46061; *Streptococcus gordonii* Challis subst CH1; *Streptococcus mutans* NN2025 uid46353; *Streptococcus mutans*; *Streptococcus pyogenes* M1 GAS; *Streptococcus pyogenes* MGAS5005; *Streptococcus pyogenes* MGAS2096; *Streptococcus pyogenes* MGAS9429; *Streptococcus pyogenes* MGAS10270; *Streptococcus pyogenes* MGAS6180; *Streptococcus pyogenes* MGAS315; *Streptococcus pyogenes* SSI-1; *Streptococcus pyogenes* MGAS 10750; *Streptococcus pyogenes* NZ131; *Streptococcus thermophiles* CNRZ1066; *Streptococcus thermophiles* LMD-9; *Streptococcus thermophiles* LMG 18311; *Clostridium botulinum* A3 Loch Maree; *Clostridium botulinum* B Eklund 17B; *Clostridium botulinum* Ba4 657; *Clostridium botulinum* F Langeland; *Clostridium cellulolyticum* H10; *Finegoldia magna* ATCC 29328; *Eubacterium rectale* ATCC 33656; *Mycoplasma gallisepticum*; *Mycoplasma mobile* 163K; *Mycoplasma penetrans*; *Mycoplasma synoviae* 53; *Streptobacillus moniliformis* DSM 12112; *Bradyrhizobium* BTAi1; *Nitrobacter hamburgensis* X14; *Rhodopseudomonas palustris* BisB18; *Rhodopseudomonas palustris* BisB5; *Parvibaculum lavamentivorans* DS-1; *Dinoroseobacter shibae* DFL 12; *Gluconacetobacter diazotrophicus* Pal 5 FAPERJ; *Gluconacetobacter diazotrophicus* Pal 5 JGI; *Azospirillum* B510 uid46085; *Rhodospirillum rubrum* ATCC 11170; *Diaphorobacter* TPSY uid29975; *Verminephrobacter eiseniae* EF01-2; *Neisseria meningitides* 053442; *Neisseria meningitides* alpha14; *Neisseria meningitides* Z2491; *Desulfovibrio salexigens* DSM 2638; *Campylobacter jejuni doylei* 269 97; *Campylobacter jejuni* 81116; *Campylobacter jejuni*; *Campylobacter lari* RM2100; *Helicobacter hepaticus*; *Wolinella succinogenes*; *Tolumonas auensis* DSM 9187; *Pseudoalteromonas atlantica* T6c; *Shewanella pealeana* ATCC 700345; *Legionella pneumophila* Paris; *Actinobacillus succinogenes* 130Z; *Pasteurella multocida*; *Francisella tularensis novicida* U112; *Francisella tularensis holarctica*; *Francisella tularensis* FSC 198; *Francisella tularensis tularensis*; *Francisella tularensis* WY96-3418; and *Treponema denticola* ATCC 35405. Accordingly, aspects of the present disclosure are directed to a Cas9 protein present in a Type II CRISPR system, which has been rendered nuclease null or which has been rendered a nickase as described herein.

The Cas9 protein may be referred by one of skill in the art in the literature as Csn1. The *S. pyogenes* Cas9 protein sequence is shown below. See Deltcheva et al., Nature 471, 602-607 (2011) hereby incorporated by reference in its entirety. There may be protein-level modifications that are made to the *S. pyogenes* Cas9 protein sequence for activity in eukaryotic cells. One example may be nuclear-localization signals, including 2 or 3 in the N or C termini of *S. pyogenes* Cas9.

According to certain aspects, a guide RNA corresponding to the target double stranded nucleic acid sequence of interest, i.e. the guide RNA may bind to the target double stranded nucleic acid sequence of interest and also complex with Cas9, is designed using methods known to those of skill in the art, preincubated with Cas9 and then added to a sample, which may be a single cell or collection of cells, containing the target DNA. The guide RNA and Cas9 will then co-localize to and form a complex with the target DNA. One of skill based on the present disclosure will readily be able to identify or design guide RNAs and Cas9 proteins which co-localize to a DNA including a target nucleic acid. The guide RNAs can be made by direct solid-phase synthesis of RNA (available from vendors such as IDT) or by in vitro transcription of solid-phase synthesized DNA oligos. The gRNA can be synthesized from array-synthesized oligos, and amplified.

Target nucleic acids include any nucleic acid sequence to which a co-localization complex as described herein can be useful to cut. Target nucleic acids include genes. The target nucleic acid may be within DNA extracted from a single cell. The target nucleic acid may be DNA extracted from a single chromosome. The target nucleic acid may be within DNA within a single cell. For purposes of the present disclosure, DNA, such as double stranded DNA, can include the target nucleic acid and a co-localization complex can bind to or otherwise co-localize with the DNA at or adjacent or near the target nucleic acid and in a manner to cut the target nucleic acid. Such target nucleic acids can include endogenous (or naturally occurring) nucleic acids and exogenous (or foreign) nucleic acids.

As used herein, the term "chromosome" refers to the support for the genes carrying heredity in a living cell, including DNA, protein, RNA and other associated factors. The conventional international system for identifying and numbering the chromosomes of the human genome is used herein. The size of an individual chromosome may vary within a multi-chromosomal genome and from one genome to another. A chromosome can be obtained from any species. A chromosome can be obtained from an adult subject, a juvenile subject, an infant subject, from an unborn subject (e.g., from a fetus, e.g., via prenatal test such as amniocentesis, chorionic villus sampling, and the like or directly from the fetus, e.g., during a fetal surgery) from a biological sample (e.g., a biological tissue, fluid or cells (e.g., sputum, blood, blood cells, tissue or fine needle biopsy samples, urine, cerebrospinal fluid, peritoneal fluid, and pleural fluid, or cells therefrom) or from a cell culture sample (e.g., primary cells, immortalized cells, partially immortalized cells or the like). In certain exemplary embodiments, one or more chromosomes can be obtained from one or more genera including, but not limited to, Homo, Drosophila, Caenorhabditis, Danio, Cyprinus, Equus, Canis, Ovis, Ocorynchus, Salmo, Bos, Sus, Gallus, Solanum, Triticum, Oryza, Zea, Hordeum, Musa, Avena, Populus, Brassica, Saccharum and the like.

The following examples are set forth as being representative of the present disclosure. These examples are not to be construed as limiting the scope of the present disclosure as these and other equivalent embodiments will be apparent in view of the present disclosure, figures and accompanying claims.

EXAMPLE I

In Vivo Gene Editing in Cells

According to one aspect, methods are described herein for site-specific exon removal (i.e., skipping) in a target gene in a cell using a CRISPR/Cas9 system. The edited gene is then expressed to produce a truncated polypeptide. According to one aspect, the truncated polypeptide has an activity similar to the full length polypeptide. According to one aspect, the cell can be a somatic cell, such as a tissue cell, such as a mammalian tissue cell. The cell can be a skeletal muscle cell, liver cell, blood cell, heart cell, skin cell, brain cell, peripheral neuronal cell, gut cell, lung cell, kidney cell, bladder cell, bone cell, fat cell, blood vessel cell or stem cell. According to one aspect, the site specific exon skipping is permanent to the extent that the target exon is removed from the target gene and the target gene is then expressed, such as by the cell, to form a protein lacking the polypeptide sequence corresponding to the removed exon. According to one aspect, the exon to be removed from the target gene includes a mutation which negatively affects the biological activity of the polypeptide. When the exon with the mutation is removed from the gene, expression of the altered gene produces an altered polypeptide which exhibits the biological activity of the full length polypeptide without the mutation.

One exemplary embodiment of the present disclosure is a method of exon removal in the Dystrophin gene in skeletal muscle using a CRISPR/Cas9 system. Duchenne Muscular Dystrophy (DMD) is an X-linked skeletal muscle disorder that afflicts 1 in every 3000 to 4000 male births and is characterized by progressive muscle wasting and weakness. DMD is caused by mutations in the Dystrophin locus, including large deletions and point mutations. Many DMD mutations cause frameshifts in the coding sequence of Dystrophin, resulting in degradation of the Dystrophin mRNA via nonsense mediated decay and absence of Dystrophin protein from the surface of muscle fibers. Loss of Dystrophin destabilizes the muscle fiber membrane, leading to contraction-mediated muscle damage and progressive loss of functional muscle. The Dystrophin protein is large and includes a central "rod" domain formed from repeating spectrin-like coils that appear largely dispensable, as reducing the number of repeats from 24 to 8 allows for relatively intact function.

According to one aspect, methods are provided herein for removing exons within the rod domain that introduce frameshifting mutations using a CRISPR/Cas9 system. Such an altered gene when expressed can produce a truncated and partially functional protein that can counter loss of functional or biologically active Dystrophin. Accordingly, aspects of the present disclosure are directed to removing one or more mutations from the Dystrophin gene using a CRISPR/Cas9 system with two or more guide RNAs to excise the one or more mutations resulting in an edited Dystrophin gene. The edited Dystrophin gene is then expressed to produce a functional truncated Dystrophin protein.

According to one aspect, guide RNA are designed to target sequences to direct Cas9-mediated cleavage of DNA at specific genetic sequences within the Dystrophin gene flanking a particular target mutation, such as a point mutation. Cleavage at both flanking sites excises the intervening DNA to remove the mutation and to introduce a precise deletion that restores the proper reading frame of the protein.

One of ordinary skill in the art will readily identify other target genes for exon excision where the exon includes a mutation and where excision of the exon produces an altered polypeptide having biological activity similar to the full length polypeptide without the mutation. Additional exemplary target genes include genes known to be associate with cancer, such as oncogenes, genes associated with amyotrophic lateral sclerosis, genes associated with trinucleotide repeat disorders including polyglutamine diseases such as Huntington's disease, prior-related diseases such as Creutzfeldt-Jakob disease and Fatal Familial Insomnia and genes associated with Marfan syndrome and Dysferlin-associated dystrophies (Aartsma-Rus et. al, Therapeutic exon skipping for dysferlinopathies?, *Eur J Hum Genet.* 2010 August; 18(8):889-94.)

EXAMPLE II

Construction and Screening of Guide RNA Plasmids

Candidate guide RNAs (gRNAs) were designed by searching the sequences flanking exon 23 and exons 52 and 53 of the mouse Dystrophin gene for appropriate sequence features (e.g., presence of PAM sequence). The sequences for the DNA binding portion of the guide RNAs were determined and are listed below:

```
Exon 23 5' (left) guide RNA:
                               (SEQ ID NO: 15)
GAATAATTTCTATTATATTACA Exon 23 3' (right) guide RNA:
                               (SEQ ID NO: 16)
TTCGAAAATTTCAGGTAAGCCG Exon 52 5' (left) guide RNA:
                               (SEQ ID NO: 17)
TCATTTCTAAAAGTCTTTTGCC Exon 53 3' (right) guide RNA:
                               (SEQ ID NO: 18)
TTTGAGACACAGTATAGGTTAT
```

Full length sequences are provided below.

```
Exon 23 5' (left) guide RNA:
                               (SEQ ID NO: 19)
GAATAATTTCTATTATATTACAGTTTaAGAGCTAtgctgGAAAcagcaTA GCAAGTTtAAATAAGGCTAGTCCGTTATCAACTTGAAAAAGTGGCACCGA

GTCGGTGCTTTTTTT

Exon 23 3' (right) guide RNA:
                               (SEQ ID NO: 20)
TTCGAAAATTTCAGGTAAGCCGGTTTaAGAGCTAtgctgGAAAcagcaTA GCAAGTTtAAATAAGGCTAGTCCGTTATCAACTTGAAAAAGTGGCACCGA

GTCGGTGCTTTTTTT

Exon 52 5' (left) guide RNA:
                               (SEQ ID NO: 21)
TCATTTCTAAAAGTCTTTTGCCGTTTaAGAGCTAtgctgGAAAcagcaTA GCAAGTTtAAATAAGGCTAGTCCGTTATCAACTTGAAAAAGTGGCACCGA

GTCGGTGCTTTTTTT

Exon 53 3' (right) guide RNA:
                               (SEQ ID NO: 22)
TTTGAGACACAGTATAGGTTATGTTTaAGAGCTAtgctgGAAAcagcaTA GCAAGTTtAAATAAGGCTAGTCCGTTATCAACTTGAAAAAGTGGCACCGA

GTCGGTGCTTTTTTT
```

Lack of predicted off target sites in other coding regions of the mouse genome was confirmed for candidate gRNAs by aligning the protospacers to the mouse genome using Blast online tool. Confirmed protospacers were cloned into gRNA cloning vector (world wide website addgene.org/41824/) using overlap extension PCR. Different pairs of guide RNA plasmids flanking exon 23 or exons 52 and 53 were co-transfected with Sp hCas9_p2A GFP encoding plasmid into mouse C2C12 myoblast cells using lipofectamine 2000 Reagent (Invitrogen) according to the manufacturer's instructions. After three to four days, the transfected cells were sorted out based on GFP expression, and genomic DNA was extracted using the quickextract DNA extraction solution (Epicentre). Primers flanking the gRNA target sites were used to amplify exon 23 and also exons 52 and 53 by PCR. The PCR products were purified and sequenced by Sanger and deep sequencing. Guide RNA pairs with the highest efficiency for removing the targeted Dystrophin exons were used for the in vivo experiments.

EXAMPLE III

In Vivo Electroporation

Animals were anesthetized using Isoflurane and injected with 50 ul of 2 mg/ml hyaluronidase in the tibialis anterior muscles. After 1 hour, two plasmids encoding the two gRNAs, hCas9 encoding plasmid or hCas9 mRNA (Trilink), and GFP encoding plasmid were co-injected in the hyaluronidase-injected muscles. hCas9 is humanized codon optimized S. pyogenes Cas9, and the gene encoding hCas9 was obtained from addgene (world wide website addgene-.org/41815.) Muscles were electroporated by applying 10 pulses of 20 ms at 200 V/cm with 100 ms intervals using an ECM 830 electro square porator (BTX Harvard apparatus) and a two needle array.

EXAMPLE IV

Single Fiber Isolation and Sequencing

Animals were sacrificed and injected muscles were harvested 10 days after electroporation and digested with 0.2% collagenase type II in DMEM for 50 min in a 37° C. water bath. Muscles were triturated with a fire polished Pasteur pipette and GFP+ transduced single fibers were isolated using a fluorescent dissection microscope. DNA was isolated from single fibers by quickextract DNA extraction solution (Epicentre). Targeted exons were PCR amplified using primers flanking the gRNA target sites. Deep sequencing libraries were prepared by adding adaptors to the PCR products using PCR, and libraries were sequenced by Illumina Miseq.

EXAMPLE V

Excision of Target Exon Using a CRISPR Cas9 System

Cas9 with addition of 3×NLSs and multiplexed guide RNAs flanking exon 23 (mutated in the mdx mouse model of DMD) were delivered directly into skeletal muscle fibers in vivo (see FIG. 4) and into cultured mouse C2C12 myoblasts (See FIGS. 2 and 3).

The sequence of the Cas9 protein (with the addition of 3×NLSs in italics) that was used is shown below:

(SEQ ID NO: 23)
MDKKYSIGLDIGTNSVGWAVITDEYKVPSKKFKVLGNTDR

HSIKKNLIGALLFDSGETAEATRLKRTARRRYTRRKNRICY

LQEIFSNEMAKVDDSFFHRLEESFLVEEDKKHERHPIFGNIV

DEVAYHEKYPTIYHLRKKLVDSTDKADLRLIYLALAHMIK

FRGHFLIEGDLNPDNSDVDKLFIQLVQTYNQLFEENPINAS

GVDAKAILSARLSKSRRLENLIAQLPGEKKNGLFGNLIALS

LGLTPNFKSNFDLAEDAKLQLSKDTYDDDLDNLLAQIGDQ

YADLFLAAKNLSDAILLSDILRVNTEITKAPLSASMIKRYDE

HHQDLTLLKALVRQQLPEKYKEIFFDQSKNGYAGYIDGGA

SQEEFYKFIKPILEKMDGTEELLVKLNREDLLRKQRTFDNG

-continued
SIPHQIHLGELHAILRRQEDFYPFLKDNREKIEKILTFRIPYY

VGPLARGNSRFAWMTRKSEETITPWNFEEVVDKGASAQSF

IERMTNFDKNLPNEKVLPKHSLLYEYFTVYNELTKVKYVT

EGMRKPAFLSGEQKKAIVDLLFKTNRKVTVKQLKEDYFKK

IECFDSVEISGVEDRFNASLGTYHDLLKIIKDKDFLDNEENE

DILEDIVLTLTLFEDREMIEERLKTYAHLFDDKVMKQLKRR

RYTGWGRLSRKLINGIRDKQSGKTILDFLKSDGFANRNFM

QLIHDDSLTFKEDIQKAQVSGQGDSLHEHIANLAGSPAIKK

GILQTVKVVDELVKVMGRHKPENIVIEMARENQTTQKGQ

KNSRERMKRIEEGIKELGSQILKEHPVENTQLQNEKLYLYY

LQNGRDMYVDQELDINRLSDYDVDHIVPQSFLKDDSIDNK

VLTRSDKNRGKSDNVPSEEVVKKMKNYWRQLLNAKLITQ

RKFDNLTKAERGGLSELDKAGFIKRQLVETRQITKHVAQIL

DSRMNTKYDENDKLIREVKVITLKSKLVSDFRKDFQFYKV

REINNYHHAHDAYLNAVVGTALIKKYPKLESEFVYGDYK

VYDVRKMIAKSEQEIGKATAKYFFYSNIMNFFKTEITLANG

EIRKRPLIETNGETGEIVWDKGRDFATVRKVLSMPQVNIVK

KTEVQTGGFSKESILPKRNSDKLIARKKDWDPKKYGGFDS

PTVAYSVLVVAKVEKGKSKKLKSVKELLGITIMERSSFEKN

PIDFLEAKGYKEVKKDLIIKLPKYSLFELENGRKRMLASAG

ELQKGNELALPSKYVNFLYLASHYEKLKGSPEDNEQKQLF

VEQHKHYLDEIIEQISEFSKRVILADANLDKVLSAYNKHRD

KPIREQAENIIHLFTLTNLGAPAAFKYFDTTIDRKRYTSTKE

VLDATLIHQSITGLYETRIDLSQLGGD*SRADPKKKRKVDPKK*

*KRKVDPKKKRKV*-

Figure 4A:
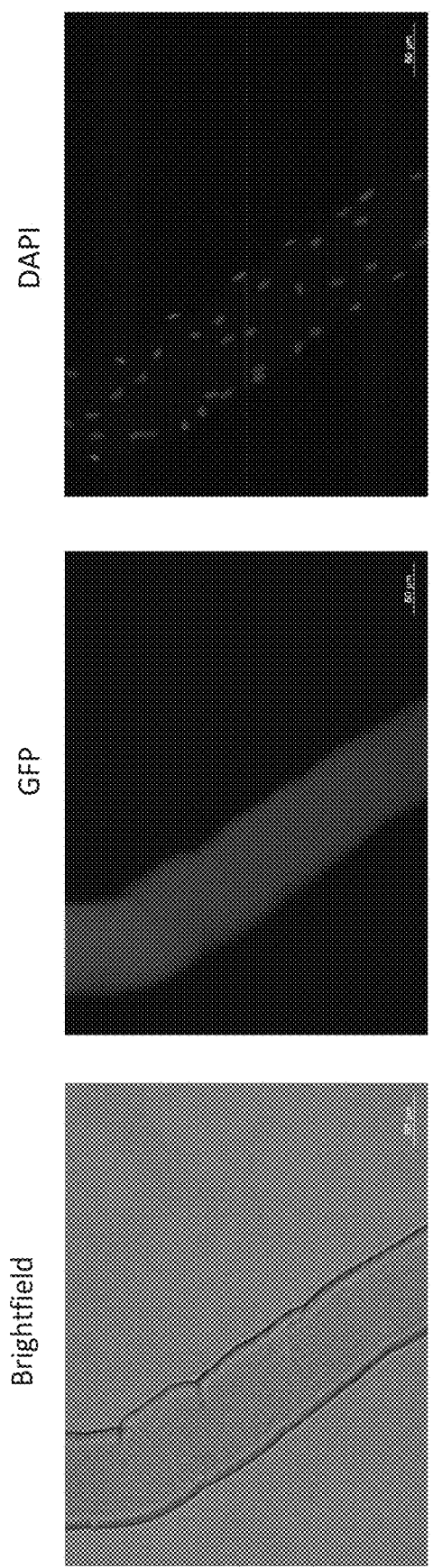
FIG. 4A is a diagram illustrating brightfield and epi-flourescent images of a multinucleated single fiber.
Figure 4B:
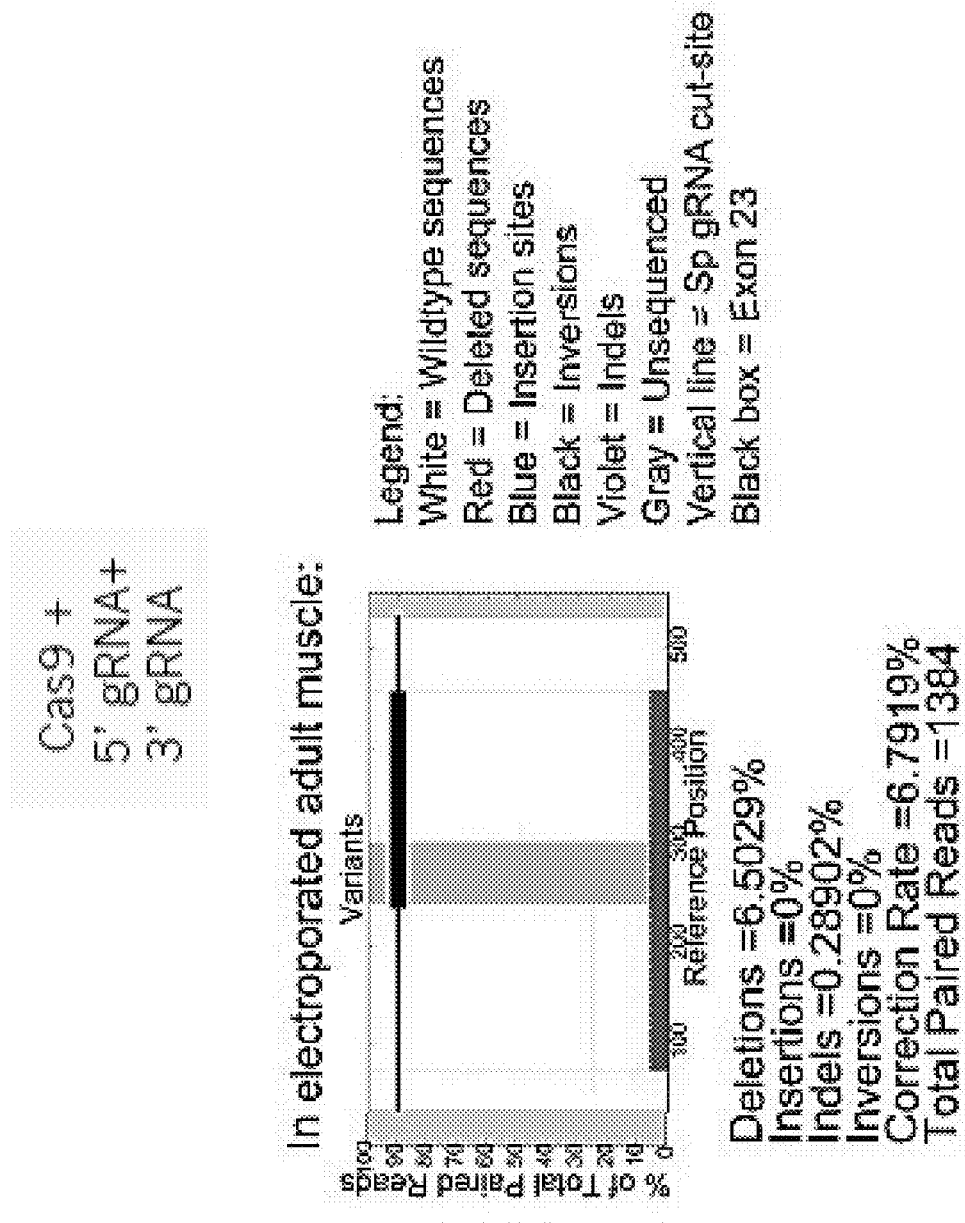
FIG. 4B is a graph illustrating results from deep sequencing of exon 23 genomic DNA amplicons from a mdx single fiber electroporated with Cas9 and two gRNAs targeting 5' and 3' of exon 23. The red signal shows the percentage of the deletion in the amplicons and the dashed lines indicate the gRNA targeting sites.

PCR amplification and DNA sequencing of the PCR product from individual muscle fibers harvested from electroporated muscle at 10 days after electroporation demonstrated that electroporation with skeletal muscle of the combination of Cas9 and exon 23 guide RNAs resulted in double cutting of the genomic DNA and deletion of the intervening sequence to restore transcript reading frame (See FIG. 4).

Figure 5B:
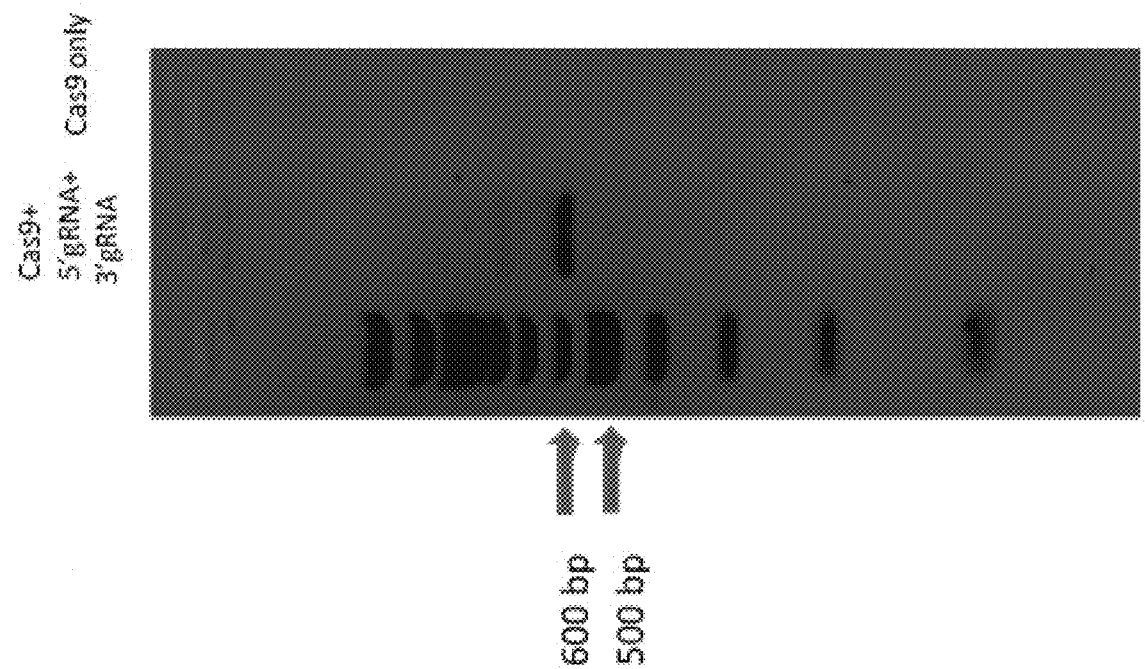
FIG. 5B is an image illustrating PCR product amplified by a primer pair spanning exons 52 and 53 of Dystrophin gene from genomic DNA of C2C12 myoblasts transfected with Cas9 only or Cas9 and two gRNAs targeting 5' of exon 52 and 3' of exon 53. Amplification only occurs when 45 kb of genomic DNA containing exons 52 and 53 between the two gRNA target sites is excised.
Figure 7A:
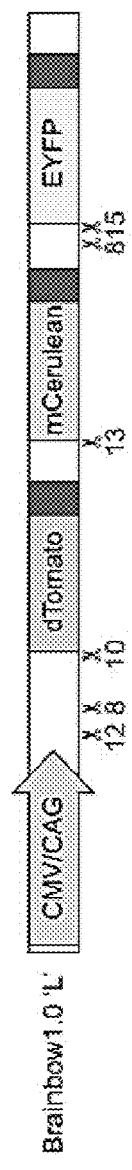
FIG. 7A is a schematic diagram of a multiplex-able CRISPR-dependent fluorescent reporter, derived from Brainbow1.0 'L' (see Livit et al., Nature, 450(7166):56-62 (2007)). Excision of the dTomato cassette by guide RNAs CB12 or CB10 with guide RNA CB13 leads to mCerulean expression, while excision of tdTomato and mCerulean cassette by guide RNAs CB12 or CB10 with guide RNA CB15, or by guide RNA CB8 only, leads to EYFP expression.
Figure 7B:
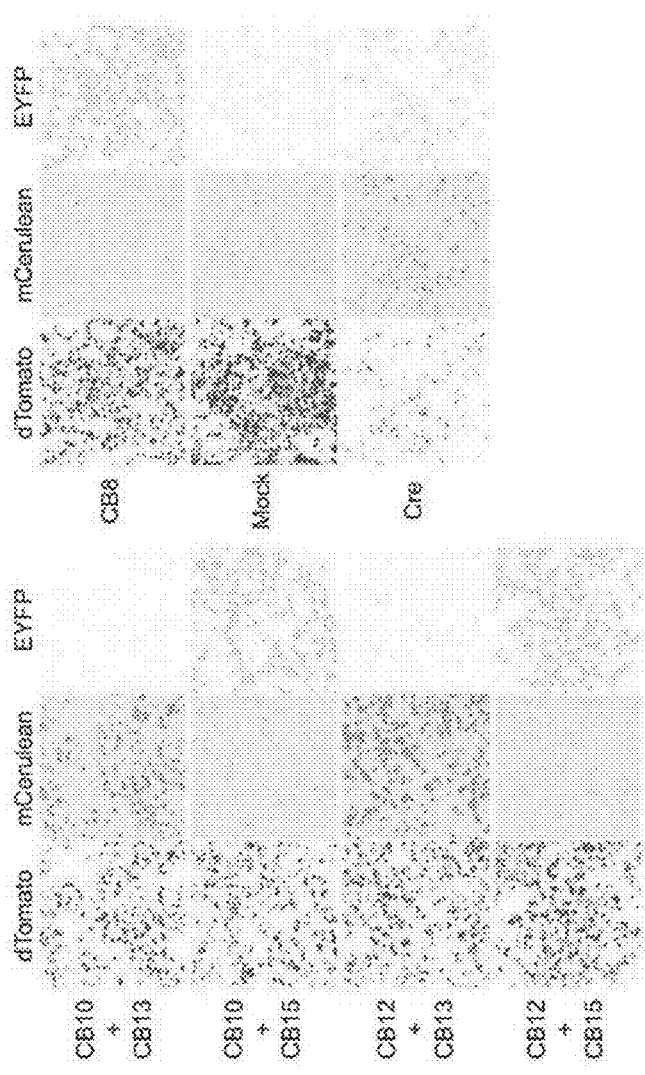
FIG. 7B illustrates results from transfection of CRISPR in HEK293 cells expressing the Brainbow1.0 'L' construct results in CRISPR-mediated fluorescent activation.
Figure 7C:
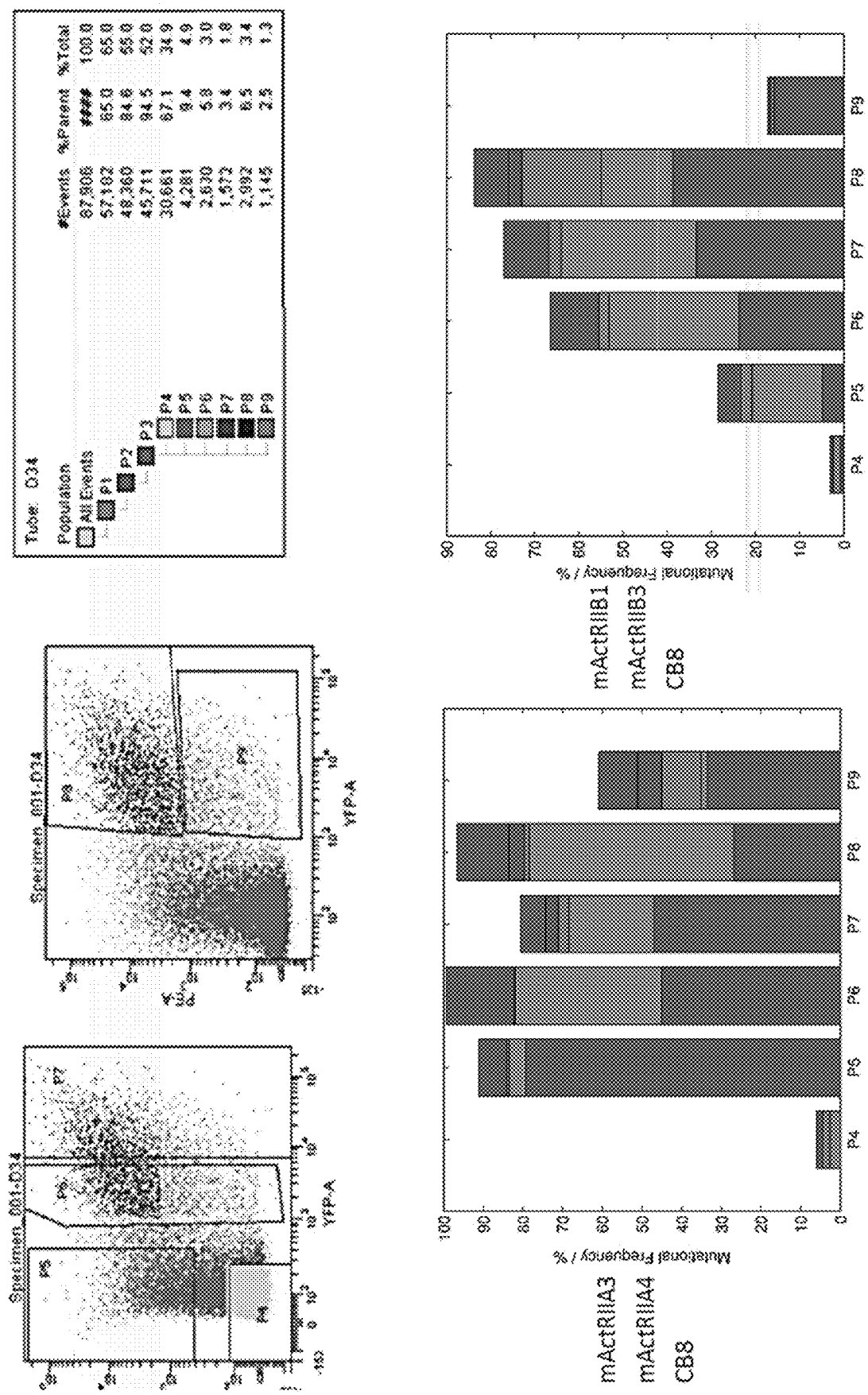
FIG. 7C illustrates results from linkage of guide RNA CB8 to guide RNAs targeting endogenous genes of interest (GOI) which selectively enriches for GOI mutants in the EYFP-positive subpopulations. C2C12 were co-lipofected with plasmids encoding Brainbow1.0 Cas9, and a single plasmid encoding guide RNA CB8 together with 2 guide RNAs targeting GOI. Cells were sorted based on dTomato and EYFP fluorescence intensities. Subpopulations were then deep sequenced for the GOI loci. EYFP-positive subpopulations (P5-P9) harbor GOI mutations >10-fold more than non-fluorescent subpopulation (P4).
Figure 9:
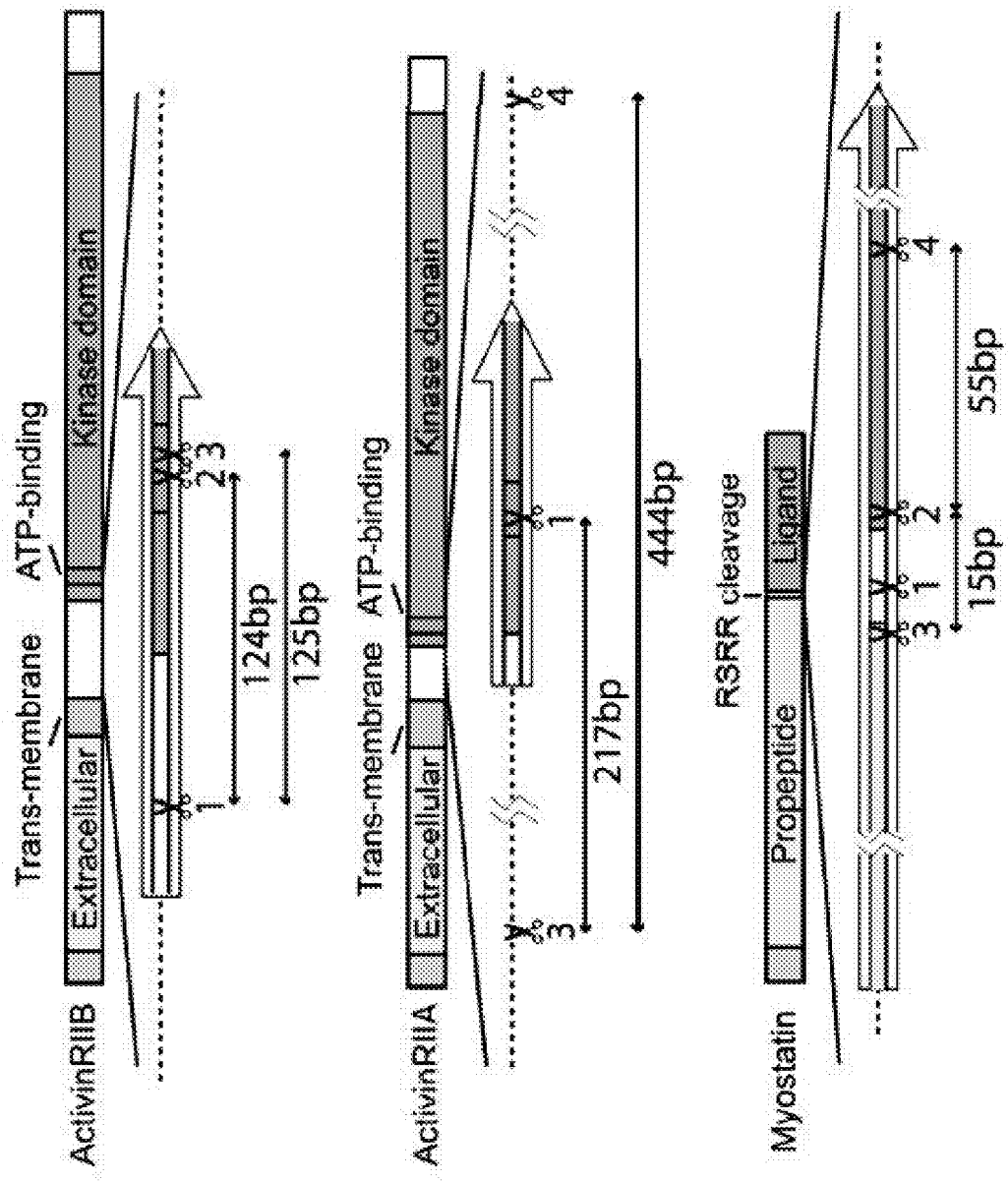
FIG. 9 is a schematic diagram of guide RNAs targeting the mouse activin receptor IIB (mActRIIB), activin receptor IIA (mActRIIA), and myostatin (mMstn) genes.

Cas9 and multiplexed guide RNAs flanking exons 52 and 53 (mutated in the mdx4cv mouse model of DMD) are delivered directly into cultured mouse C2C12 myoblasts. C2C12 transfection of the combination of Cas9 and guide RNAs flanking exons 52 and 53 results in double cutting of the genomic DNA and deletion of the intervening sequence to restore transcript reading frame (See FIG. 5). According to this aspect, the CRISPR/Cas9 system can be used to excise large nucleic acid segments from a target gene, for example, so as to produce a biologically functional expressed protein.

EXAMPLE VI

In Vivo Gene Editing of Loci Corresponding to Myostatin and Its Receptors ActRIIA and ActRIIB Paired Sp gRNAs were used to generate two double-strand breaks (DSBs) flanking the desired genomic excision, promoting end-joining of the genomic sequences. Target sites were chosen to disrupt the myostatin-activin receptor pathway, thereby derepressing the myostatin-mediated inhibition of muscle growth and leading to musclehypertrophy (see Lee et al., Proc. Natl. Acad. Sci. USA, 2001; 98(16): 9306-11). For the myostatin gene, the physiological RSRR cleavage site between the propeptide and activin receptor-binding domains was targeted, to create deletions or missense mutations that result in an uncleaved myostatin protein, and nonsense mutations that result in a truncated myostatin, both dominant negative forms of myostatin. Accordingly, aspects of the present disclosure are directed to producing dominant negative forms of a protein using the Cas9 mediated methods derscribed herein. For TGFβ-family activin receptors IIB and IIA, the region between the transmembrane and kinase domains was targeted, excising the ATP-binding domains, which likewise results in dominant-negative activin ligand traps that bind cognate ligands but lack functional kinase activity.

Figure 10A:
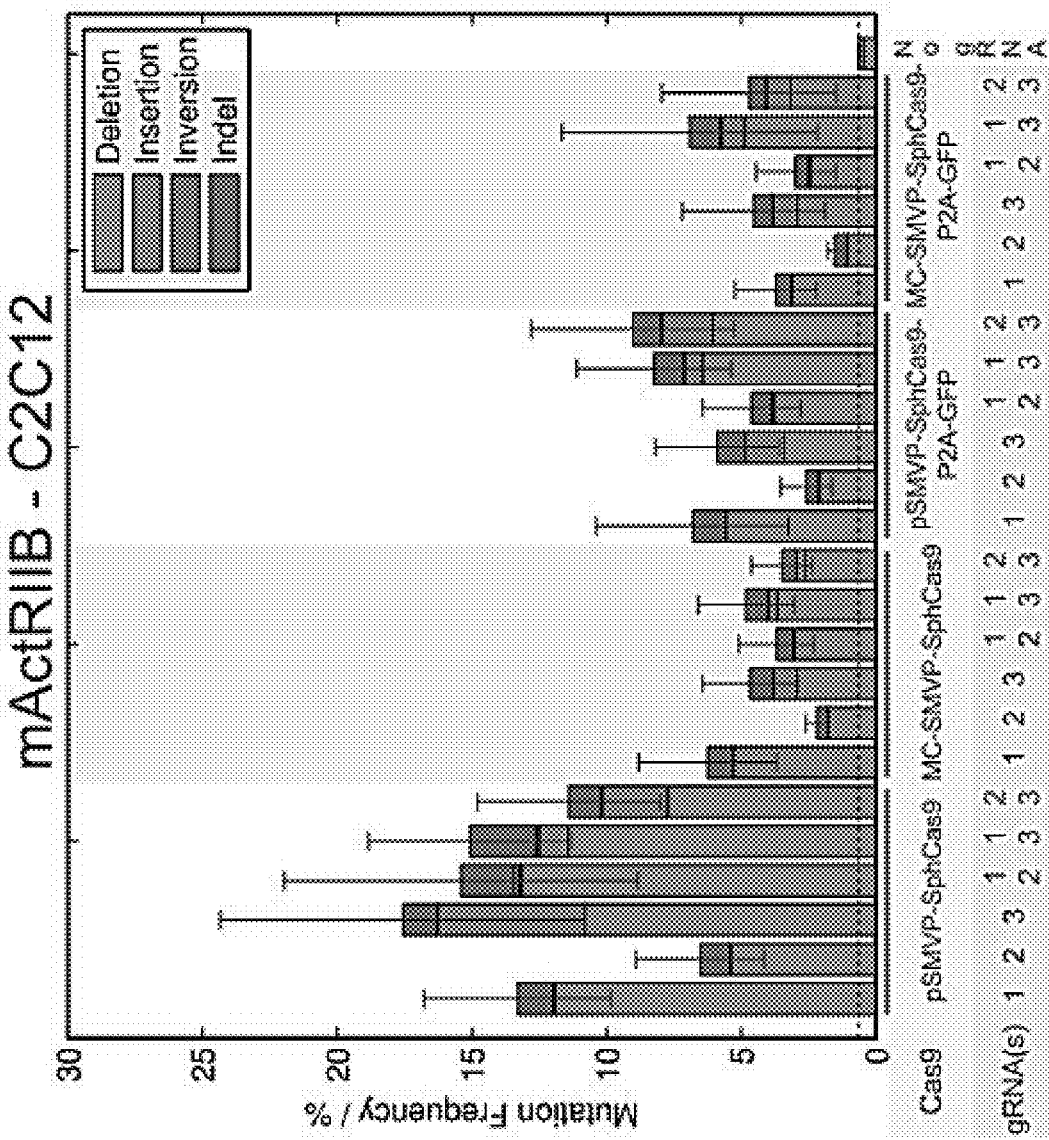
FIG. 10A illustrates results of mutation frequencies in unselected C2C12 cells lipofected with either single guide RNAs or paired guide RNAs, using four forms of Cas9-expressing constructs (pSMVP: plasmid with an SV40enhancer-CMV-chimeric intron promoter; MC-SMVP: minicircle with the same promoter; with or without P2A-turboGFP for co-translational expression of yurboGFP).
Figure 10A:
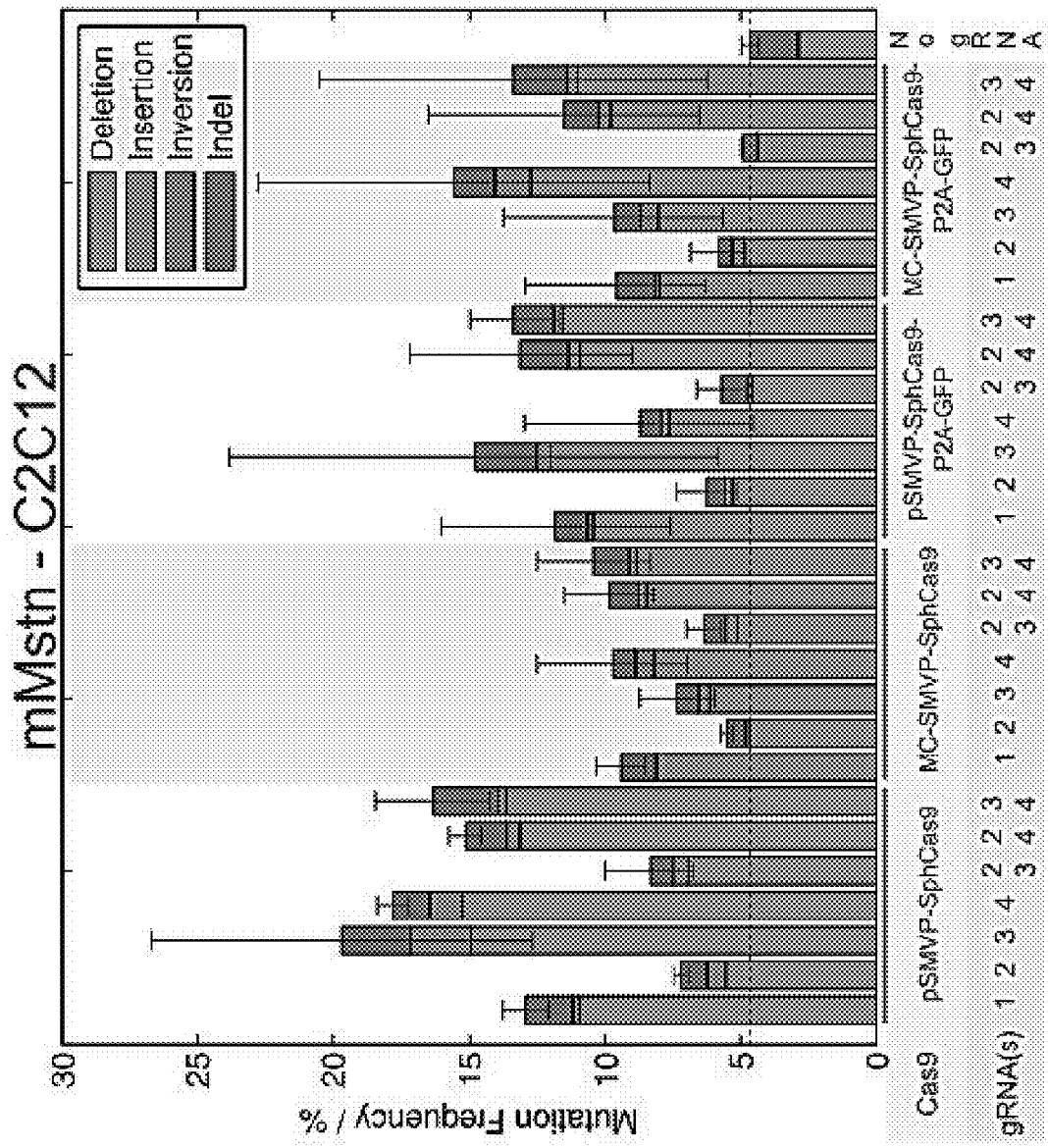
Figure 10A:
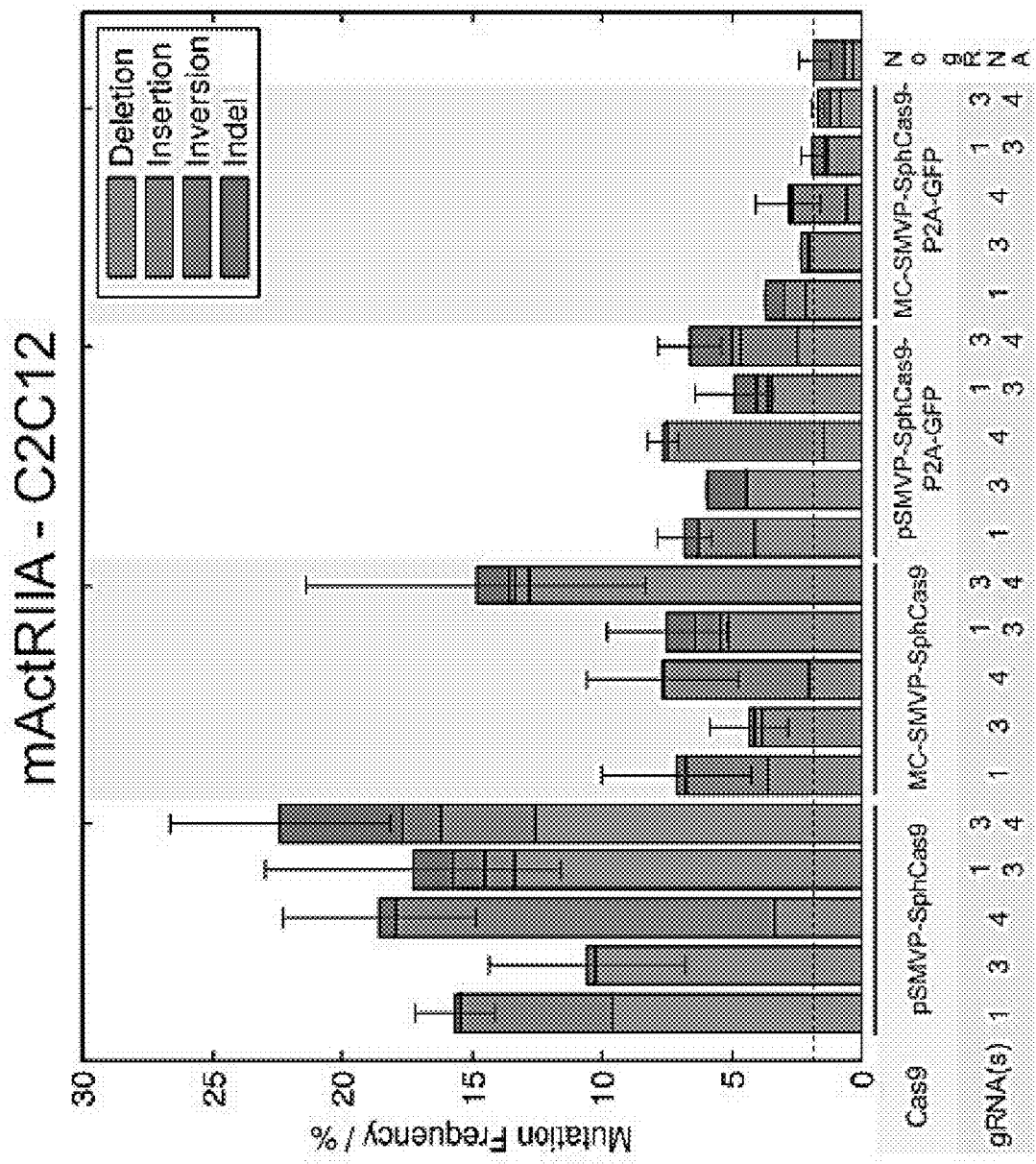
Figure 10B:
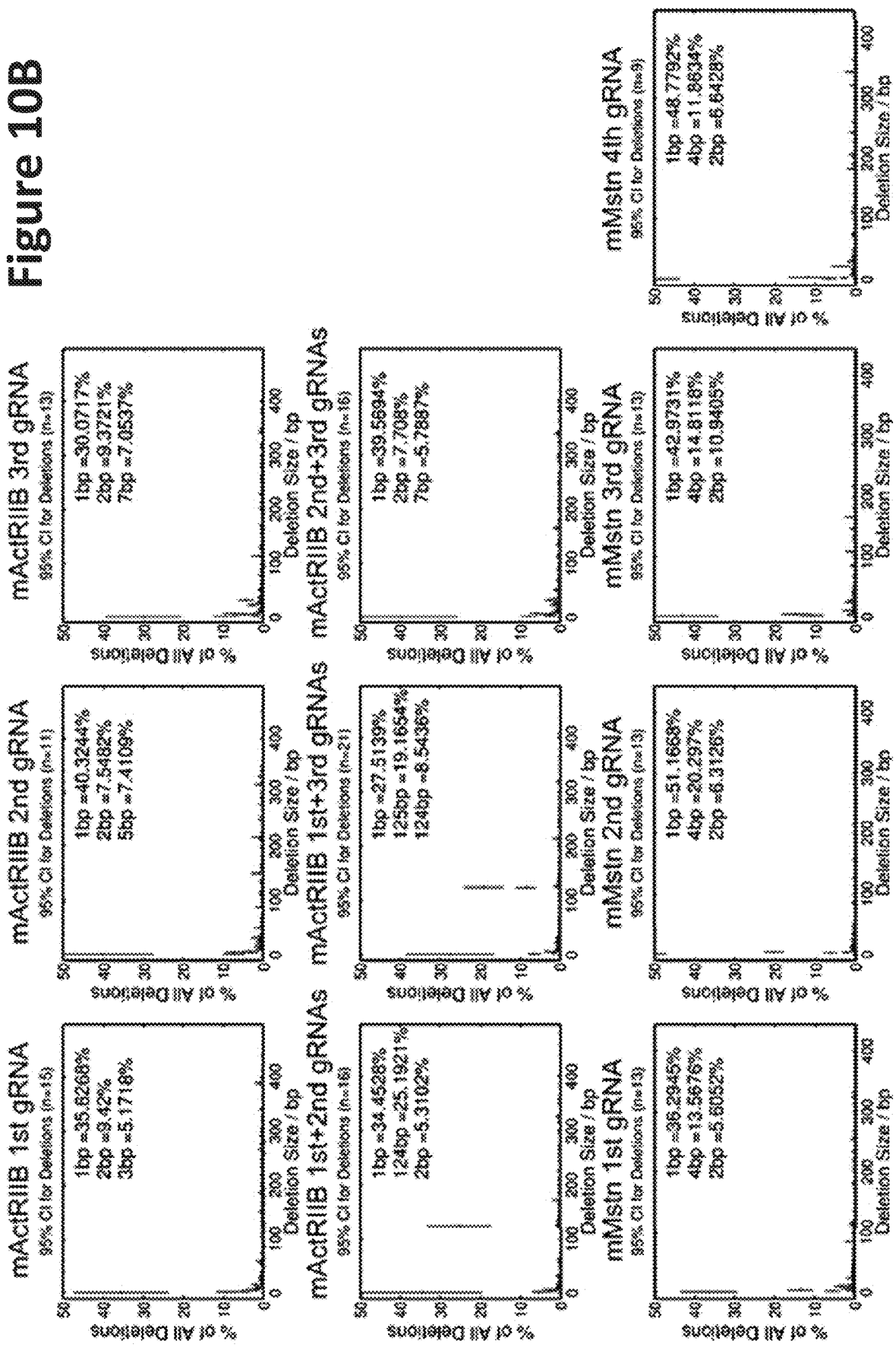
FIG. 10B illustrates deletion sizes generated by single or paired guide RNAs.
Figure 10B:
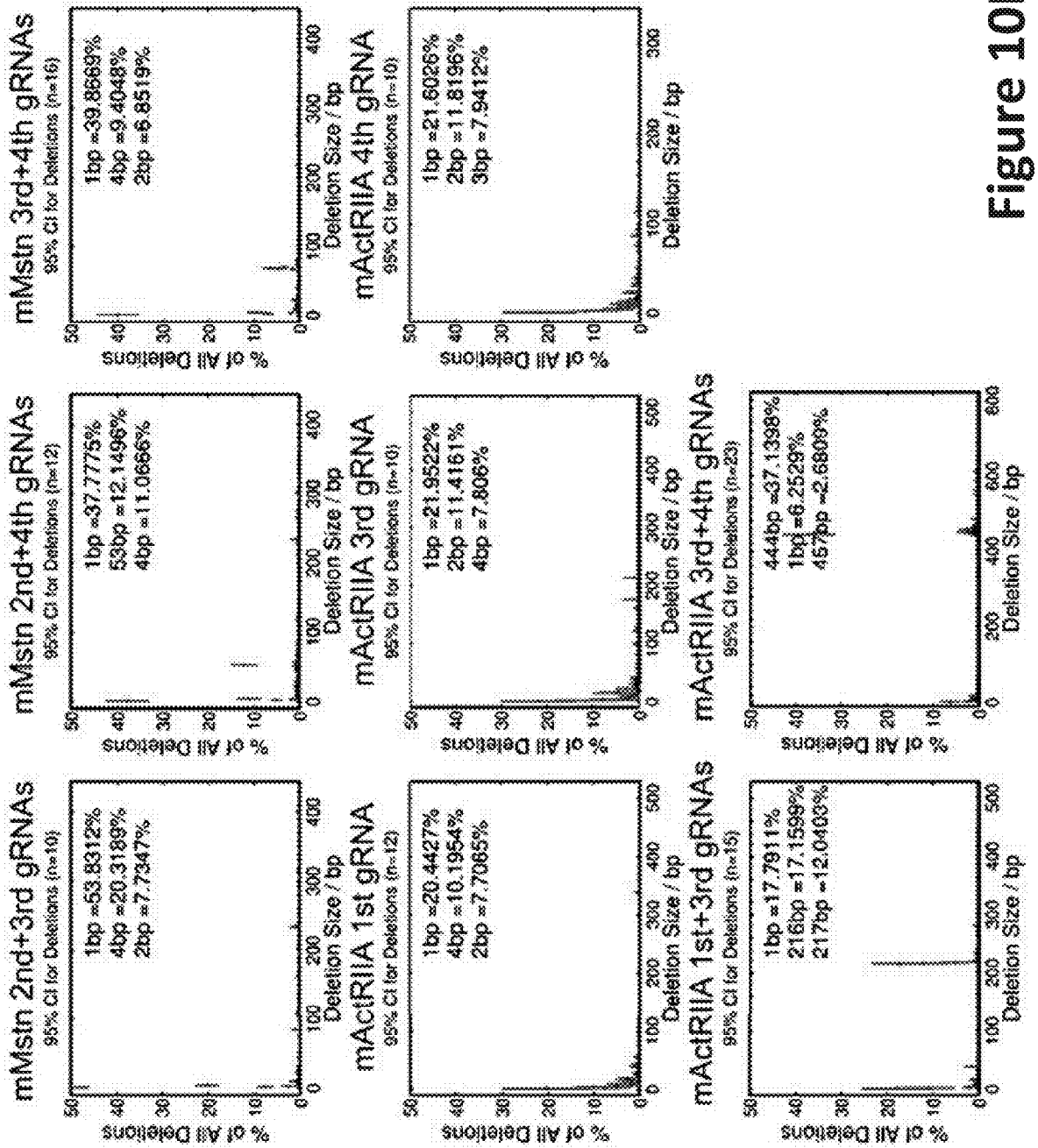
Figure 10C:
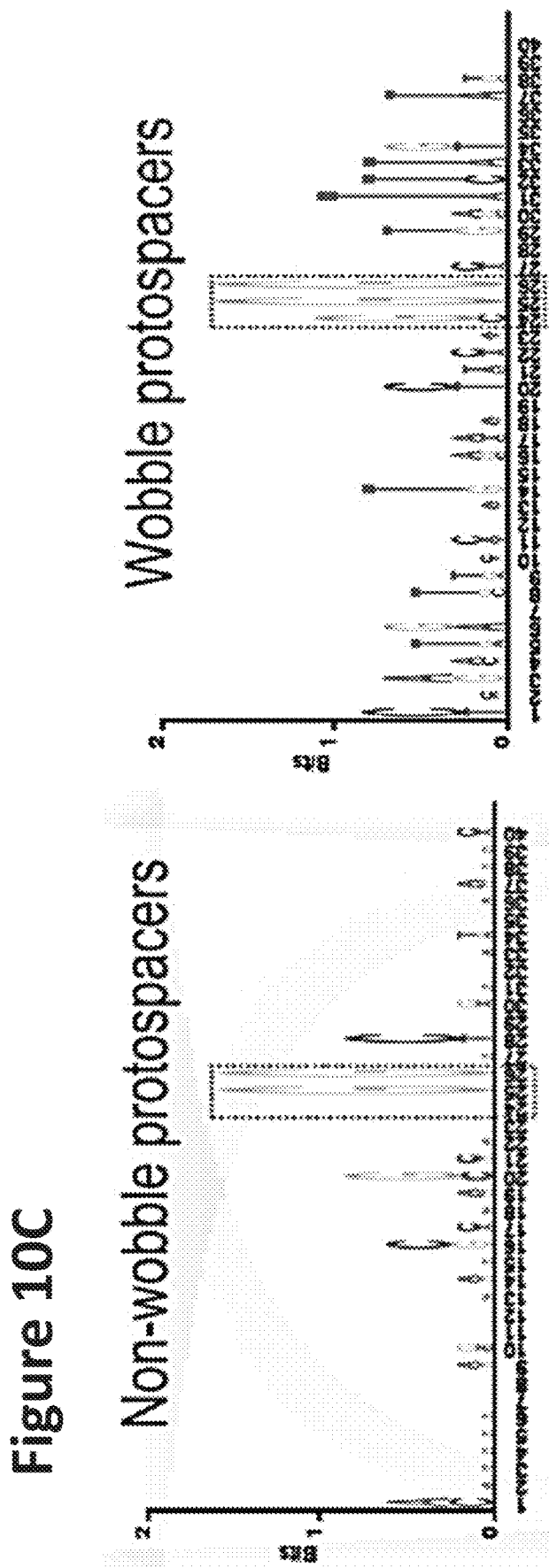
FIG. 10C is a diagram illustrating results from examining breakpoint junctions. The results reveal that genomic loci with GGG PAM exhibit cut-site wobble, where the CRISPR-induced double-strand break is 3 bp or 4 bp upstream of the PAM.
Figure 11A:
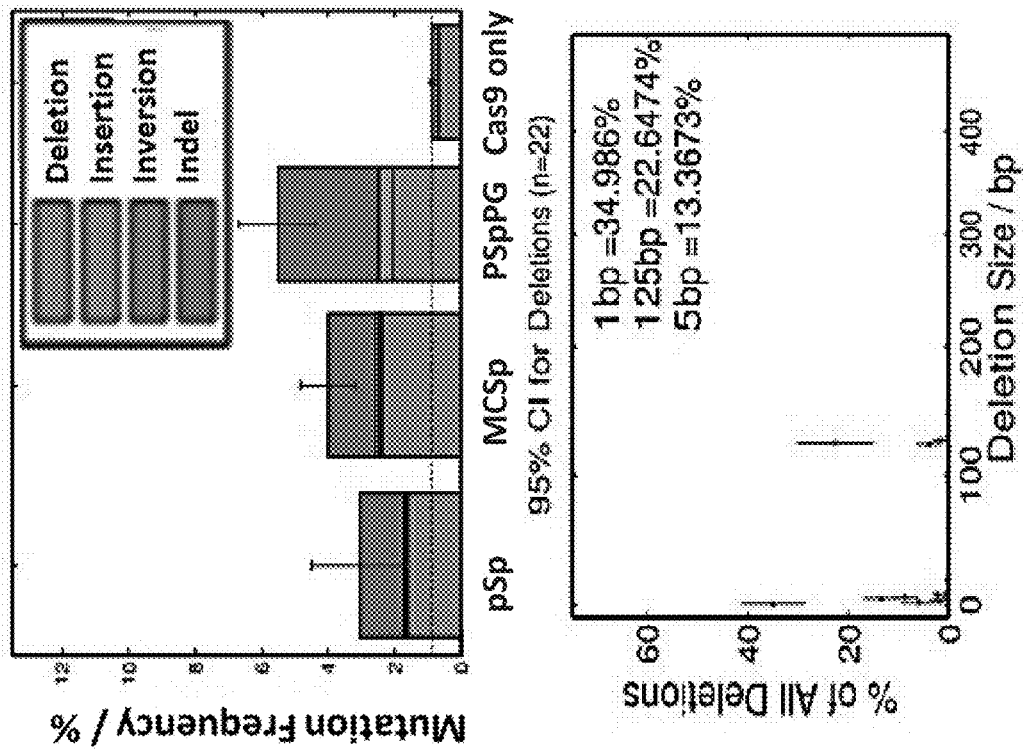
FIG. 11A illustrates results from CRISPR-mediated gene editing in adult muscle fibers. 2-10% of genomes in multi-nucleated muscle fibers were mutated after electroporation of CRISPR into adult mouse TA muscle. Using paired guide RNAs allows precise deletion of intervening genomic sequences.
Figure 11A:
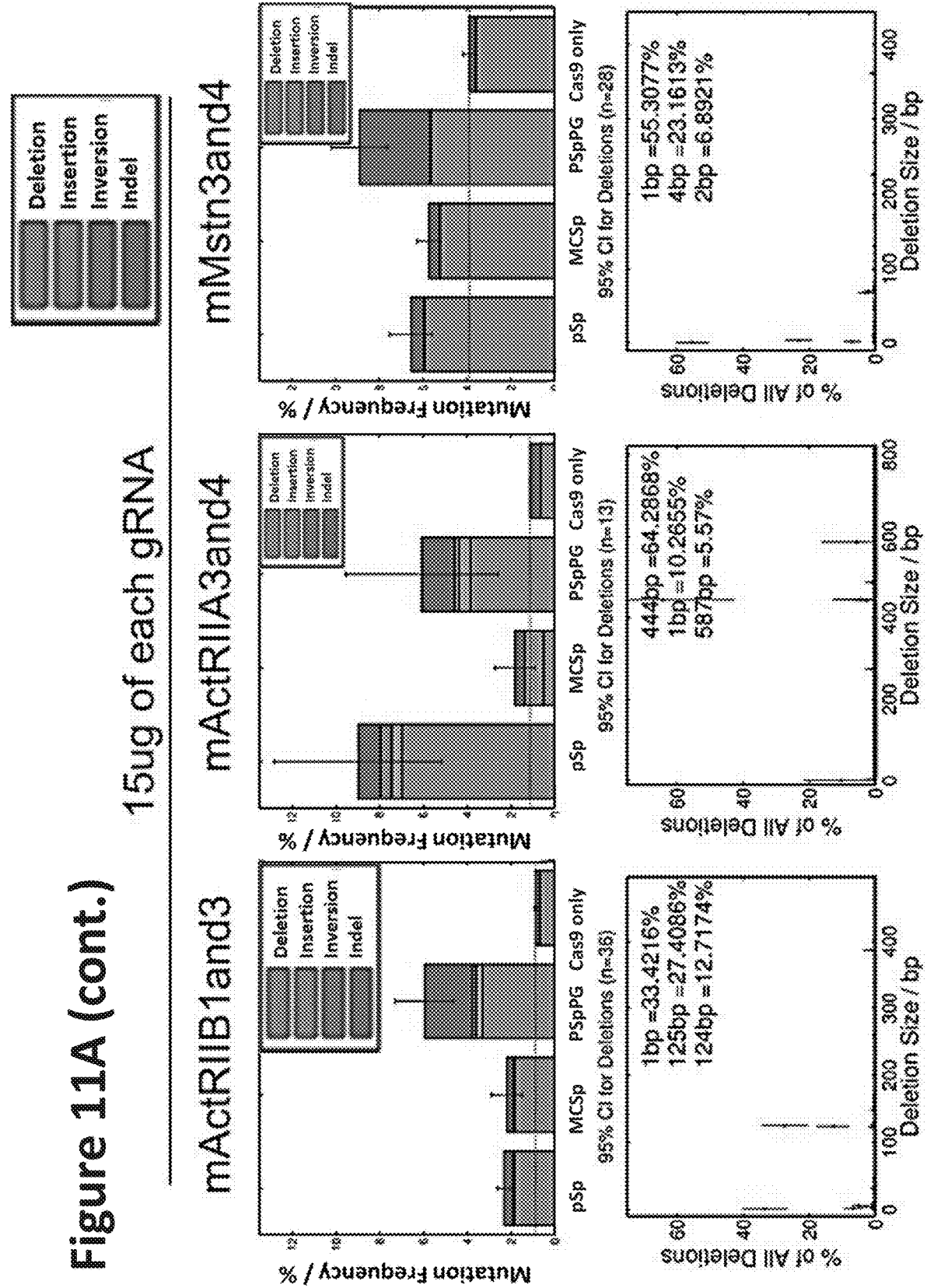
Figure 11B:
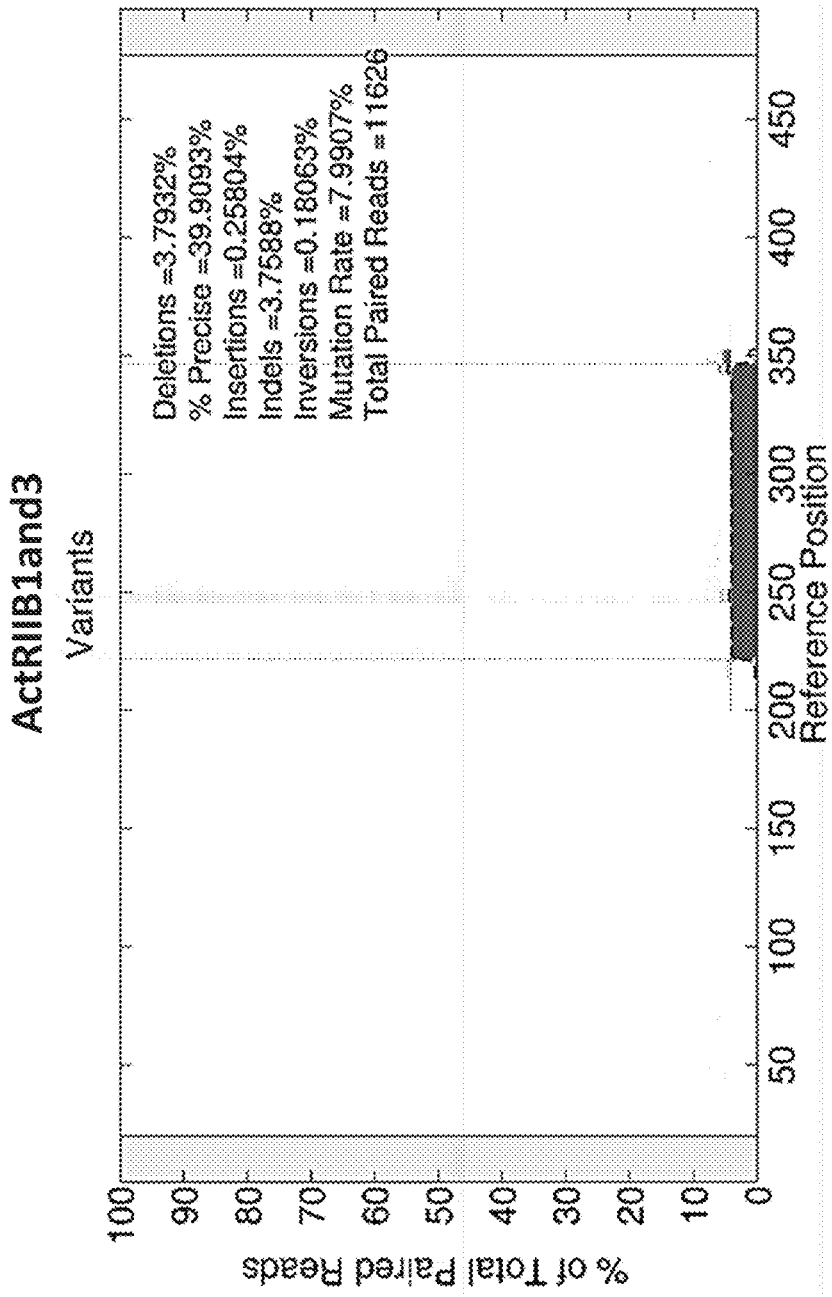
FIG. 11B illustrates results from deep sequencing alignments of a single fiber for each gene locus.
Figure 11B:
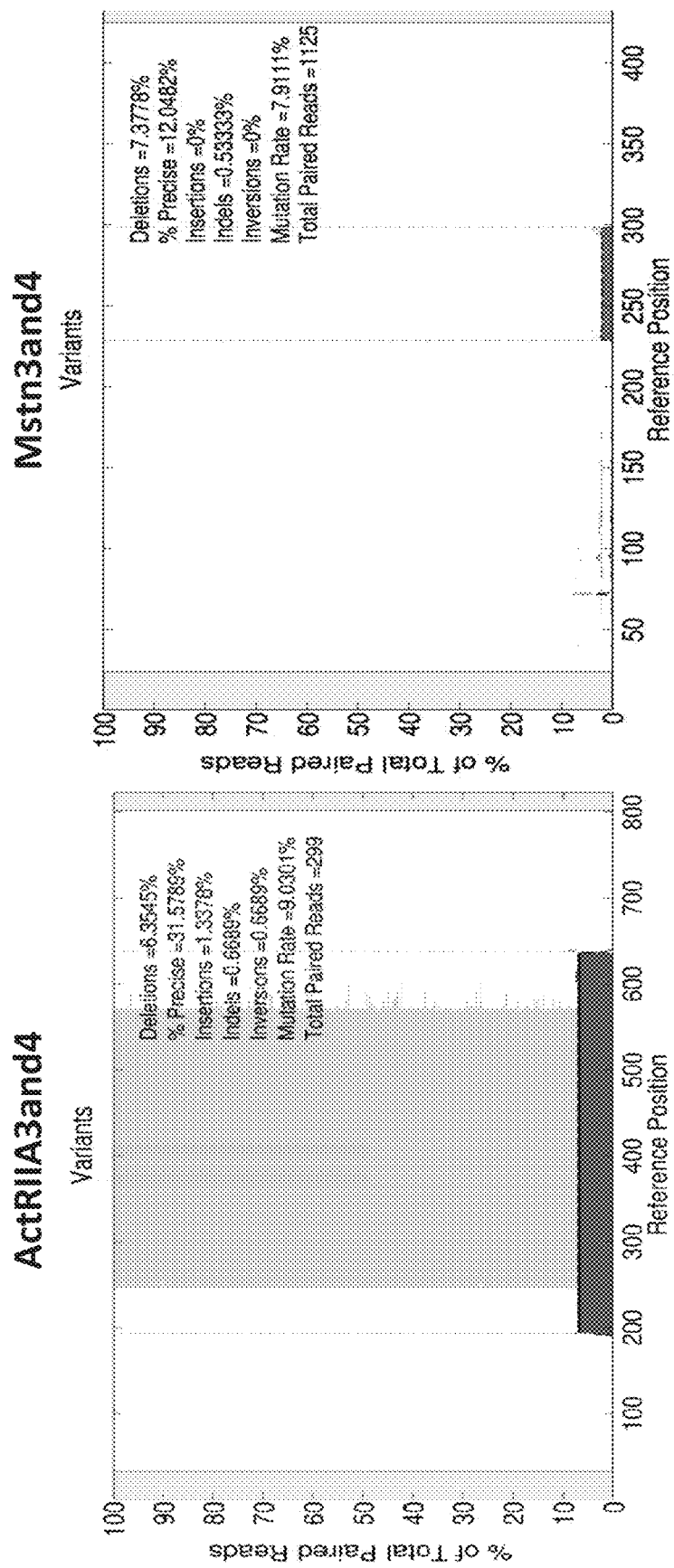

FIGS. 10A and 10B depict CRISPR lipofection in unselected C2C12 cell culture. FIG. 10A shows the panel of guide RNAs (single or paired) co-delivered with four forms of Cas9-expressing DNA constructs. For singly-transfected gRNAs, the majority of mutants harbor deletions, with the deletion window concentrated at <7 bp, but large deletions that span the entire amplicon (444-829 bp) are also observed at low frequencies (FIG. 10B). Transfection of paired gRNAs dramatically shifts the deletion profile towards intervening excision. Deep sequencing reveals that the significant proportion of breakpoint junctions are formed by end-joining of the flanking genomic sequences, corresponding to end-ligation between the SpCas9 cut-sites 3 bp 5' from the PAM NGG. Shifting the gRNA by 1 bp (compare mActRIIB1 with mActRIIB2 or mActRIIB3) shifts the excision product by 1 bp. Precise excisions can be generated through all combinations of PAMs-orientation of paired gRNAs, such as same direction, 'inwards pointing', or 'outwards pointing' PAMs. For some gRNAs pairs, wobble was observed in the breakpoints, where the putative cut-sites were shifted lbp from the expected sites (i.e. 4 bp 5' of PAM sequence, such that co-delivery of mActRIIB1 and mActRIIB3 gives rise to both 124 bp and 125 bp deletion sizes). Sequence consensus reveals that cut-site wobble manifests in the context of a GGG PAM (FIG. 10C).

Cas9 and multiplexed guide RNAs flanking sp 3$^{rd}$ ActRIIA and sp 4$^{th}$ ActRIIA were delivered directly into skeletal muscle fibers in vivo. The spacer sequences for the Sp gRNAs are listed below:

```
1st ActRIIB
                                        (SEQ ID NO: 24)
GGGCCATGTGGACATCCATGAGGTGAGACAGTGCCAGCGT

2nd ActRIIB
                                        (SEQ ID NO: 25)
GGCCTGAAGCCACTACAGCTGCTGGAGATCAAGGCTC

3rd ActRIIB
                                        (SEQ ID NO: 26)
GGCCTGAAGCCACTACAGCTGCTGGAGATCAAGGCTCG

1st ActRIIA
                                        (SEQ ID NO: 27)
GCCATTGCAGCTGTTAGAAGTGAAAGCAAG

3rd ActRIIA
                                        (SEQ ID NO: 28)
GGCCCTAGCATCTAAGTTCTCGCAGGC

4th ActRIIA
                                        (SEQ ID NO: 29)
GGTCATTCCATCTCAGCTGTGACAGCAGCGCAGAA

1st Mstn
                                        (SEQ ID NO: 30)
GGAAGTCAAGGTGACAGACACACCCAAGAGGTCC 2nd Mstn
                                        (SEQ ID NO: 31)
GGACACACCCAAGAGGTCCCGGAGAGACTTT 3rd Mstn
                                        (SEQ ID NO: 32)
GTCAAGCCCAAAGTCTCTCCGGGACCTCTT 4th Mstn
                                        (SEQ ID NO: 33)
GGAATCCCGGTGCTGCCGCTACCCCCTCA
```

All guide RNAs use the scaffold sequence shown below of Mali et al., Science, 2013; 339(6121):836-6 hereby incorporated by reference in its entirety for all purposes.

```
                                        (SEQ ID NO: 34)
GTTTTAGAGCTAGAAATAGCAAGTTAAAATAAGGCTAGTCCGTTATCAAC
TTGAAAAAGTGGCACCGAGTCGGTGCTTTTTTT
```

Deep sequencing of the PCR product from individual muscle fibers harvested from electroporated muscle at 10 days after electroporation demonstrated that electroporation into skeletal muscle of the combination of Cas9 and guide RNAs sp 3$^{rd}$ ActRIIA and sp 4$^{th}$ ActRIIA resulted in double cutting of the genomic DNA and deletion of the intervening sequence to generate a dominant negative ActRIIA coding gene. According to certain aspects, the protein is truncated specifically after the upstream guide RNA. Paired guide RNAs were chosen to delete critical domains of the proteins, while allowing precise endpoints for the deletions, such that the N-terminal portions remain expressed, at least up to the location of the upstream guide RNA or a created premature stop codon. In the case of mActRIIB and mActRIIA, these truncated proteins bind to the cognate ligands but do not transduce the relevant signals because they lack the C-terminal kinase domains. In the case of mMstn, the RSRR cleavage signal is deleted, such that with or without a frameshift, the N-terminal propeptide serves as a dominant negative protein. It is possible to retain the reading frame, if desired, by choosing guide RNAs that have their cut sites in phase of 3n within the protein-coding sequence.

Cas9 and multiplexed guide RNAs sp 1st ActRIIB and sp 3$^{rd}$ ActRIIB were delivered directly into skeletal muscle fibers in vivo. Deep sequencing of the PCR product from individual muscle fibers harvested from electroporated muscle at 10 days after electroporation demonstrated that electroporation into skeletal muscle of the combination of Cas9 and guide RNAs sp 1st ActRIIB and sp 3$^{rd}$ ActRIIB resulted in double cutting of the genomic DNA and deletion of the intervening sequence to generate a dominant negative ActRIIB coding gene.

Cas9 and multiplexed guide RNAs sp 3$^{rd}$ myostatin (Mstn) and sp 4$^{th}$ myostatin were delivered directly into skeletal muscle fibers in vivo. Deep sequencing of the PCR product from individual muscle fibers harvested from electroporated muscle at 10 days after electroporation demonstrated that electroporation into skeletal muscle of the combination of Cas9 and guide RNAs sp 3$^{rd}$ myostatin and sp 4$^{th}$ myostatin resulted in double cutting of the genomic DNA and deletion of the intervening sequence to generate a dominant negative myostatin coding gene.

Precise cutting of genomic sequence by multiplexed guide RNAs was confirmed at the above loci as shown in FIGS. 10 and 11 indicating that the methods of in vivo gene editing can be extended to any desired gene target.

EXAMPLE VII

Ratio of Cas9 to Guide RNA

Figure 12:
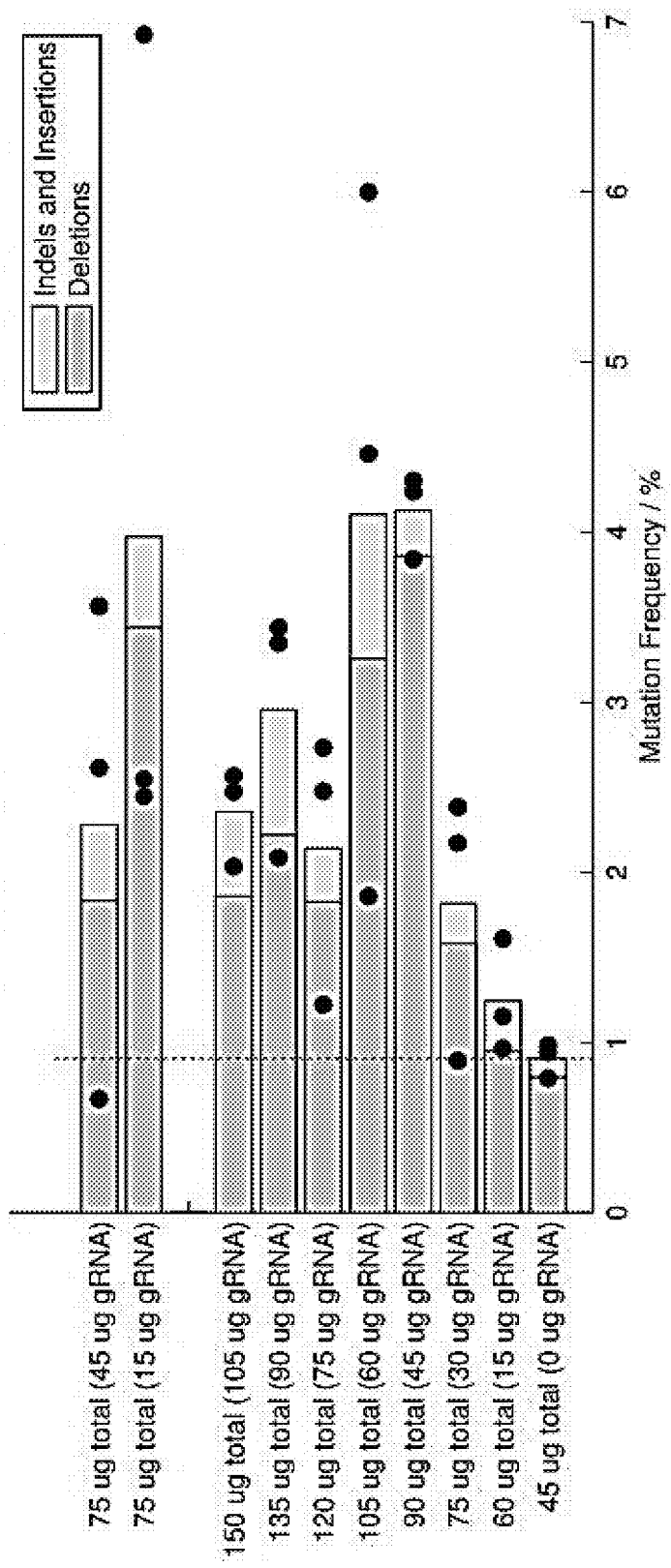
FIG. 12 is a graph illustrating inter-fiber mutational variability within the same animal Each black dot depicts the mutational frequency of a single fiber. Bars denote the mean frequency of mutational subtypes for each animal. Guide RNAs used were mActRIIB1 and mActRIIB3. n=1 mouse for each condition tested.

According to certain aspect, the ratio of Cas9 to guide RNA can affect the rate of genome modification in vivo. As shown in FIG. 12, an exemplary ratio of plasmid encoding the Cas9 protein to the plasmids encoding the guide RNA is 1:1.5 to 1:2. For the results of FIG. 12, C57Bl/6 mouse tibialis anterior (TA) muscles were electroporated with 15 ug GFP, 30 ug Cas9 and 0, 15, 30, 45, 60, 75, 90 or 105 ug of sp 1st ActRIIB and sp 3rd ActRIIB gRNA plasmids. PCR amplification and DNA sequencing of the PCR product from individual muscle fibers harvested from electroporated muscle at 10 days after electroporation demonstrated that electroporation into skeletal muscle of the combination of Cas9 and guide is most efficient when the ratio of plasmid coding Cas9 to the plasmids coding the gRNAs is 1:1.5 to 1:2.

EXAMPLE VIII

In Vivo Gene Editing in C2C12 Myoblasts

Figure 2B:
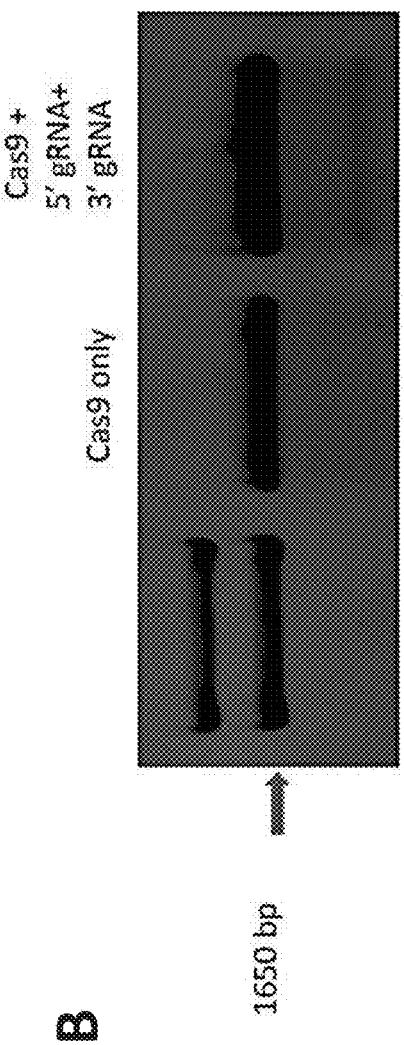
FIG. 2B is an image illustrating PCR products amplified by a primer pair spanning exon 23 of mouse Dystrophin gene from genomic DNA of C2C12 myoblasts transfected with Cas9 only or Cas9 and two gRNAs targeting 5' and 3' of exon 23. Cutting both sides of exon 23 with two gRNAs leads to excision of the exon from the DNA and amplification of a smaller PCR product corresponding to the deleted locus.
Figure 2C:
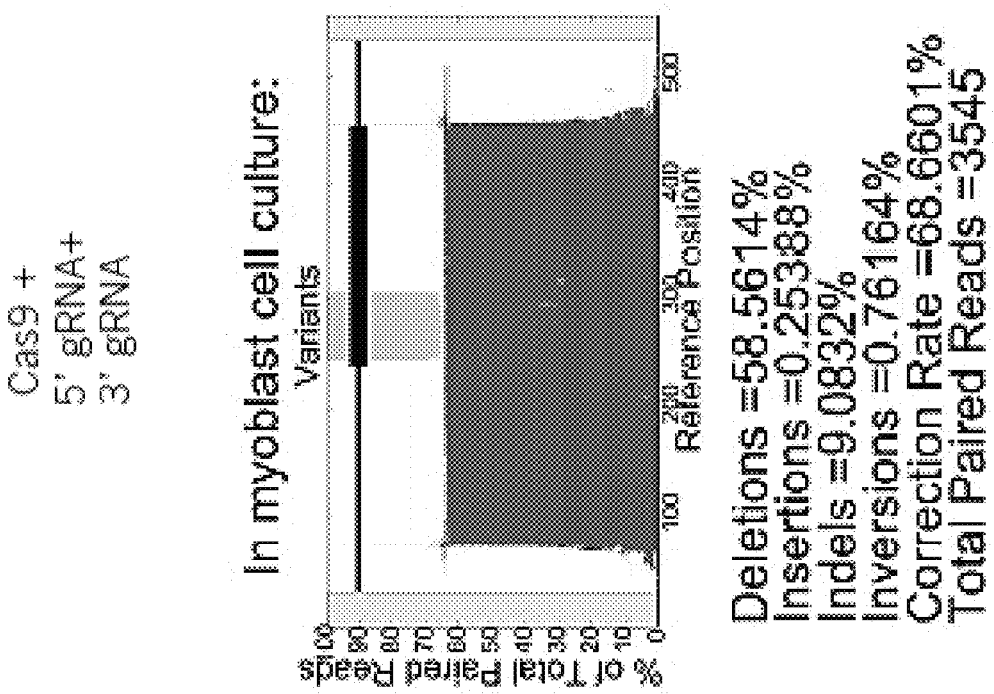
FIG. 2C is a graph illustrating results from deep sequencing of exon 23 genomic DNA amplicons from C2C12 cells transfected with Cas9 and two gRNAs targeting 5' and 3' of exon 23.

As shown in FIGS. 2, 3 and 10, the methods described herein can be applied to cultured cells, such as progenitor cells, for transplantation into an animal, such as a human. FIG. 2A is a schematic diagram of the mdx mouse genomic DNA at the mutated exon 23 locus before (top) and after (bottom) cutting the DNA with two gRNAs targeting 5' and 3' of exon 23. FIG. 2B is an image illustrating PCR products amplified by a primer pair spanning exon 23 of mouse Dystrophin gene from genomic DNA of C2C12 myoblasts transfected with Cas9 only or Cas9 and two gRNAs targeting 5' and 3' of exon 23. Cutting both sides of exon 23 with two gRNAs leads to excision of the exon from the DNA and amplification of a smaller PCR product corresponding to the deleted locus. FIG. 2C is a graph illustrating results from deep sequencing of exon 23 genomic DNA amplicons from C2C12 cells transfected with Cas9 and two gRNAs targeting 5' and 3' of exon 23.

Figure 3A:
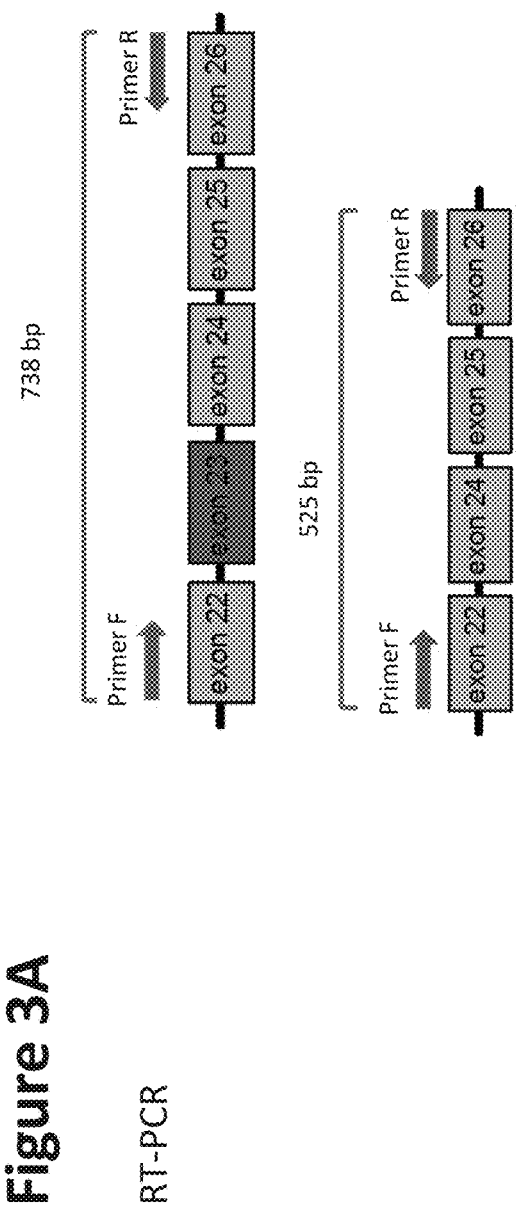
FIG. 3A is a schematic diagram of the mdx mouse mRNA at the mutated exon 23 locus before (top) and after (bottom) cutting the DNA with two gRNAs targeting 5' and 3' of exon 23. Removal of exon 23 from the mRNA restores the reading frame and leads to expression of a truncated but partially functional Dystrophin protein in dystrophic mouse muscle (Lu et. al, Functional amounts of dystrophin produced by skipping the mutated exon in the mdx dystrophic mouse, see *Nature Medicine* 9, 1009-1014 (2003).
Figure 3B:
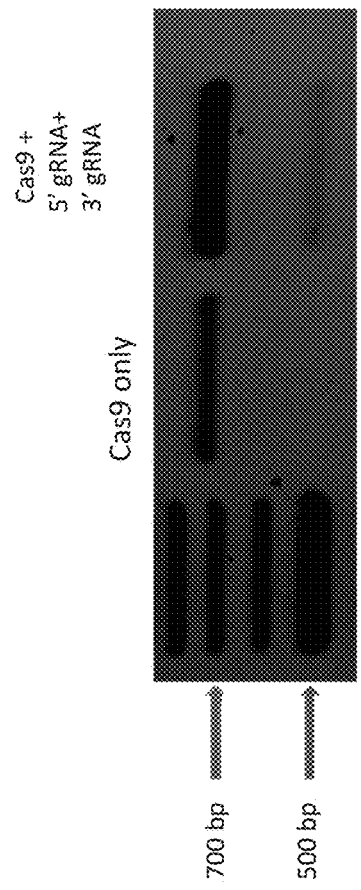
FIG. 3B is an image illustrating RT-PCR products amplified by a primer pair spanning exon 23 of mouse Dystrophin mRNA from cDNA of C2C12 myoblasts transfected with Cas9 only or Cas9 and two gRNAs targeting 5' and 3' of exon 23. Cutting both sides of Dystrophin exon 23 with two gRNAs leads to excision of the exon from the mRNA and amplification of a smaller PCR product corresponding to the transcript lacking exon 23.

FIG. 3A is a schematic diagram of the mdx mouse mRNA at the mutated exon 23 locus before (top) and after (bottom) cutting the DNA with two gRNAs targeting 5' and 3' of exon 23. Removal of exon 23 from the mRNA restores the reading frame and leads to expression of a truncated but partially functional Dystrophin protein in dystrophic mouse muscle (Lu et. al, Functional amounts of dystrophin produced by skipping the mutated exon in the mdx dystrophic mouse, Nature Medicine 9, 1009-1014 (2003). FIG. 3B is an image illustrating RT-PCR products amplified by a primer pair spanning exon 23 of mouse Dystrophin mRNA from cDNA of C2C12 myoblasts transfected with Cas9 only or Cas9 and two gRNAs targeting 5' and 3' of exon 23. Cutting both sides of Dystrophin exon 23 with two gRNAs leads to excision of the exon from the mRNA and amplification of a smaller PCR product corresponding to the transcript lacking exon 23.

FIG. 10A illustrates results of mutation frequencies in unselected C2C12 cells lipofected with either single guide RNAs or paired guide RNAs, using four forms of Cas9-expressing constructs (pSMVP: plasmid with an SV40enhancer-CMV-chimeric intron promoter; MC-SMVP: minicircle with the same promoter; with or without P2A-GFP for co-translational expression of GFP).

FIG. 10B illustrates deletion sizes generated by single or paired guide RNAs. FIG. 10C is a diagram illustrating results from examining breakpoint junctions. The results reveal that genomic loci with GGG PAM exhibit cut-site wobble, where the CRISPR-induced double-strand break is 3 bp or 4 bp upstream of the PAM.

According to this aspect, precisely edited, autologous, transplantable cells, such as progenitor cells, can be created and implanted into an animal, such as a human. Exemplary cells include stem cells such as muscle stem cells.

EXAMPLE IX

Developing a Reporter System for CRISPR In Vivo Activity

Ai9 mice (Madisen et. al A robust and high-throughput Cre reporting and characterization system for the whole mouse brain. Nat Neurosci, 2010 13(1):133-40) that harbor an inducible tdtomato reporter construct in their Rosa26 locus were used as a reporter for CRISPR in vivo double cut activity. The reporter construct includes a CAG promoter followed by a 3×STOP cassette (3×SV40 polyA translational terminators) and tdtomato coding sequence. Therefore tdtomato is only expressed when the 3×STOP cassette is removed (See FIG. 6). Guide RNAs were designed to target 5' and 3' sites of the 3×STOP cassette, and Ai9 TA muscles were electroporated with GFP and Cas9 only or GFP, Cas9 and two gRNAs targeting 5' and 3' of the 3×STOP cassette. Targeting both sides of the 3×STOP cassette leads to excision of the cassette from the genome and expression of tdtomato (See FIG. 6). This system can be used as a reporter for in vivo CRISPR activity in different tissues. Guide RNAs targeting different genes can also be co-delivered with the gRNAs targeting the 3×STOP cassette, and the targeted tissues can be detected and isolated based on tdtomato expression. The 3×STOP cassette is commonly used in LoxP mouse strains, and the 3×STOP gRNAs used are compatible with the large mouse collection publicly available.

EXAMPLE X

Immune Response to Cas9

Figure 13B:
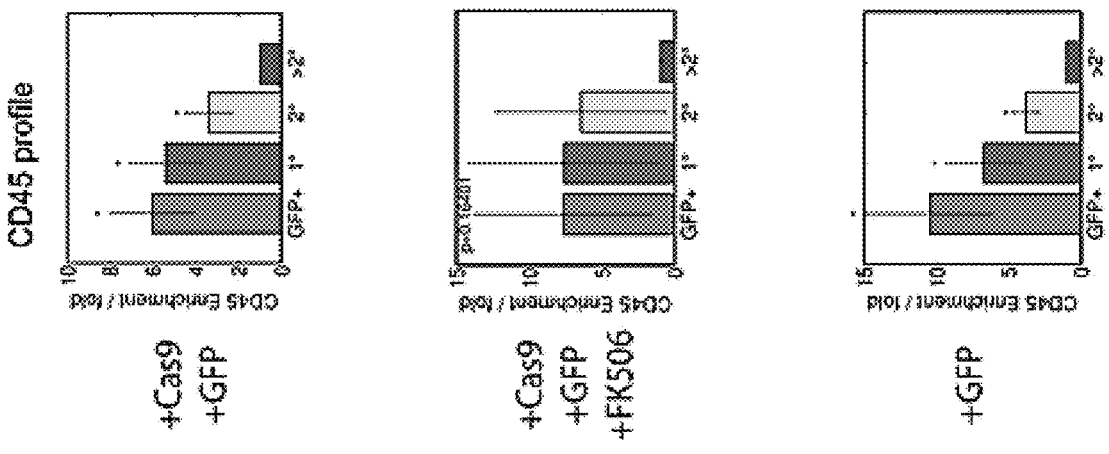
FIG. 13A-D illustrates immune response towards Cas9 and GFP, as examined with DAPI nuclear stain, CD45 antibody stain, and immune cell FACS profiling. T-cell infiltration into the transgene-expressing tissue can be alleviated with FK506 immuno-suppression.
Figure 13A:
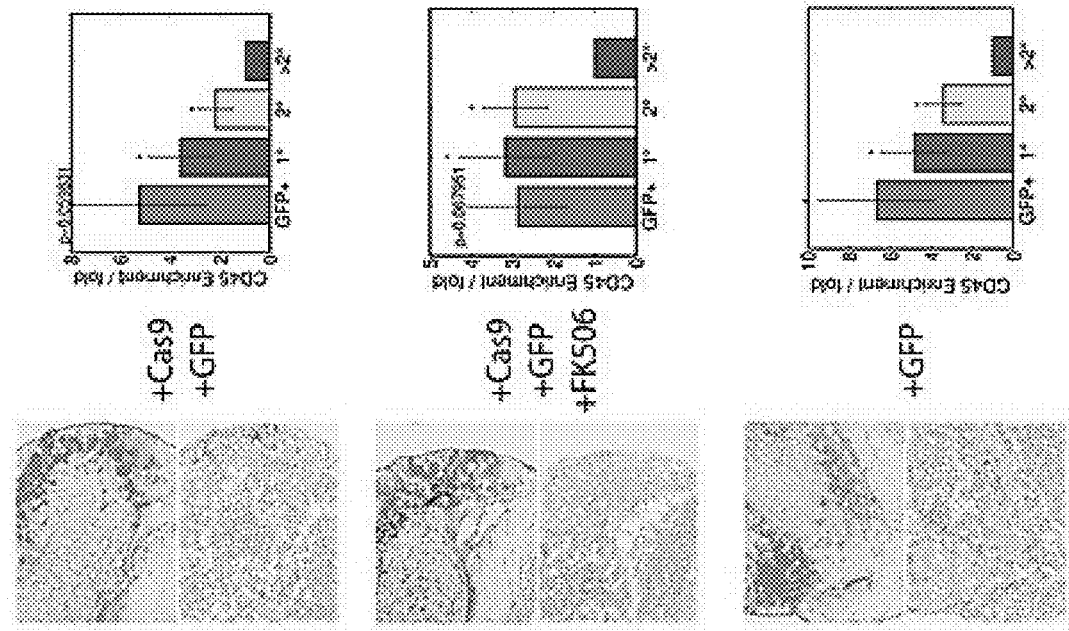
Figure 13C:
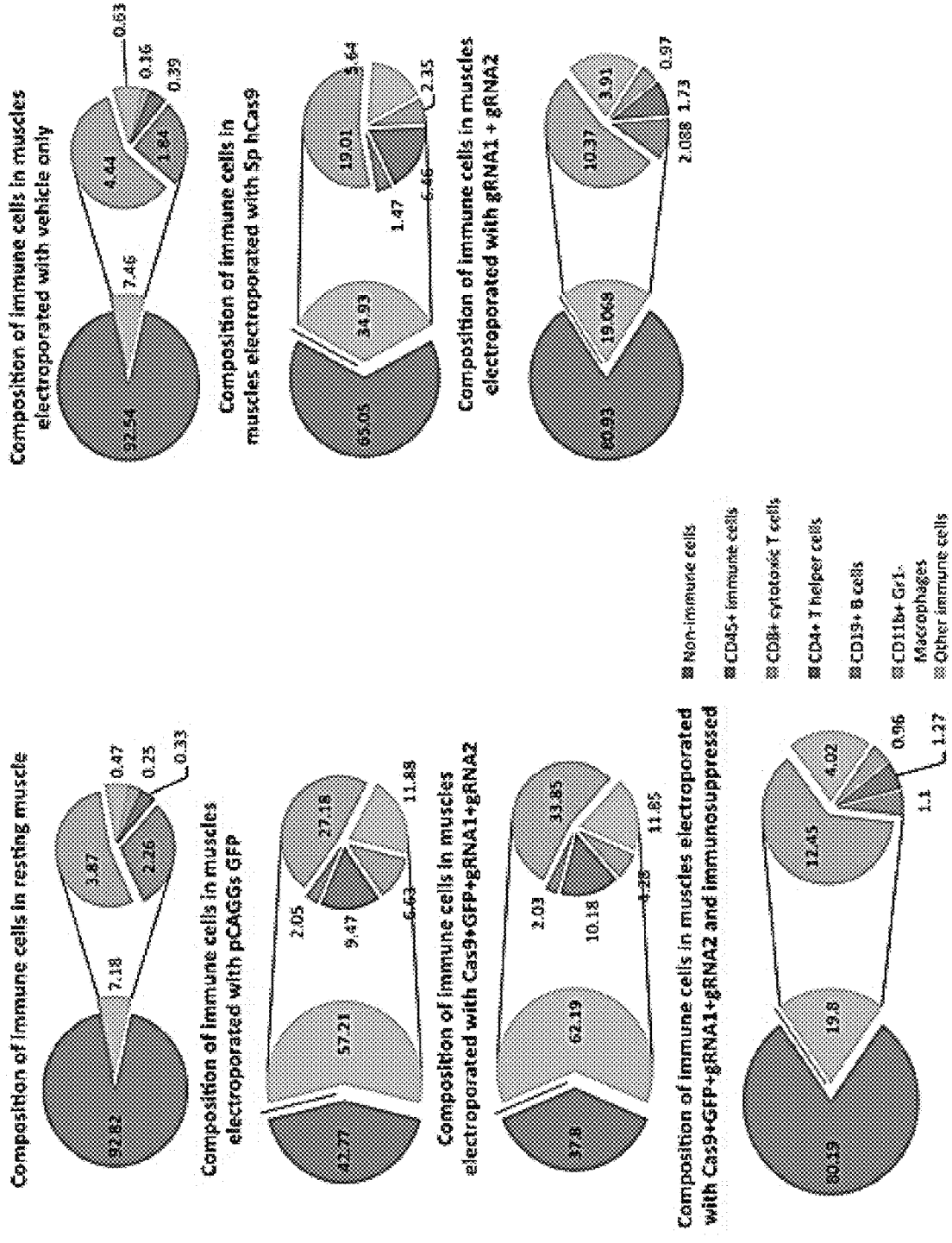
Figure 13D:
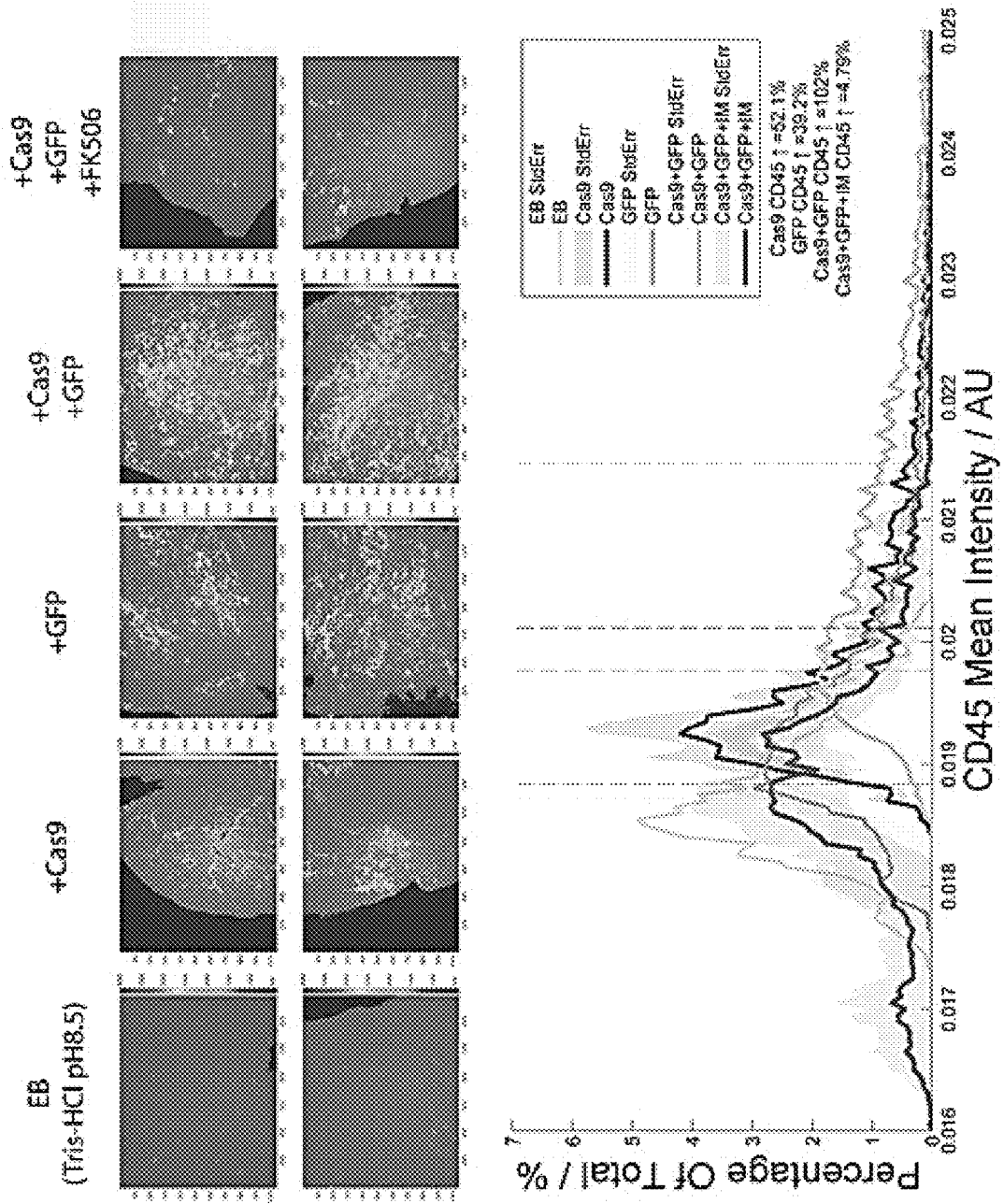

In the course of in vivo experiments, enrichment of DAPI-stained nuclei was observed in the vicinity of transgene-expressing fibers, reminiscent of immune cell infiltration. In FIG. 13A, the green represents the DAPI nuclear stain intensity around GFP-positive muscle fibers, the blue represents the DAPI stain intensity around GFP-negative muscle fibers adjacent to GFP-positive fibers (i.e., 1 degree neighbor), the yellow represents 2 degree neighbor, and the red represents 3 degree or more neighbor. Both Cas9 and GFP are exogenous transgenes that could elicit an immune response, which is a potential concern that needs to be resolved, especially in anticipation of clinical adoption of CRISPR-mediated gene therapy. The immunological cell-types present within injected muscles were profiled by antibody-staining and FACS (FIG. 13C). Similar to the GFP-only control, CRISPR induced immune cell infiltration throughout the injected muscle, enriched around transgene-expressing fibers, was visualized by CD45 antibody staining (FIGS. 13B, 13D). To alleviate the T-cell response, mice were treated with the immunosuppressant FK506, which abolishes T-cell infiltration in the injection muscle to mock-injection levels (FIGS. 13B, 13C, 13D).

EXAMPLE XI

Therapeutic Gene Editing

According to certain aspects, methods and materials are provided for editing a target gene in a cell to remove one or more exons from the target gene by administering a Cas9 protein, such as a Cas9 enzyme, and guide RNAs (CRISPR system) as described herein to an individual in need of such target gene editing, such as for treating a genetic disorder. Methods and materials are provided for therapeutic treatment of an individual suffering from Duchenne muscular dystrophy by in vivo genome editing to correct frame shifting mutations in the Dmd gene using a Cas9 enzyme and guide RNA delivered by AAV. The CRISPR system may be delivered directly to post-mitotic skeletal muscle fibers and cardiomyocytes, as well as proliferative muscle satellite cells, where the CRISPR system targets the Dmd gene for permanent exon deletion, restores Dystrophin protein expression and partially or totally recovers functional deficiencies of dystrophic muscle. The individual may be a human or a non-human animal. The Cas9 enzyme or guide RNAs may be delivered intramuscularly or systemically. Systemic administration may include intravenous administration or injection, intraperitoneal administration or injection, intramuscular administration or injection, intracranial administration or injection, intraocular administration or injection, or subcutaneous administration or injection. The Cas9 enzyme or guide RNAs may be delivered in one or more viral vectors, such as an adeno-associated virus. According to one aspect, the target gene may be the dystrophin gene and the individual may be suffering from Duchenne muscular dystrophy. According to one aspect, the target gene is in an endogenous muscle cell. According to one aspect, the target gene is in an endogenous muscle stem cell which may be referred to herein as a satellite cell. According to one aspect, a Cas9 enzyme and guide RNAs are administered to an individual to edit a target gene in a muscle cell and a target gene in a muscle stem cell. According to certain aspects, methods are provided using CRISPR/Cas9 gene editing for therapeutic modification of disease-specific alleles in muscle cells and primary muscle stem cells.

Certain exemplary aspects of the present disclosure include a permanent gene editing approach that restores Dystrophin expression in skeletal muscles, cardiac muscle, as well as muscle stem cells after intramuscular or systemic injection of adeno-associated viruses (AAVs) encoding the components of CRISPR/Cas9 gene editing system. According to certain aspects, methods described herein permanently target DMD mutations in endogenous muscle stem cells which then produce muscle cells retaining the edit to the target gene providing for long-term repair of dystrophic fibers with corrected muscle precursor cells.

Vectors are contemplated for use with the methods and constructs described herein. The term "vector" includes a nucleic acid molecule capable of transporting another nucleic acid to which it has been linked. Vectors used to deliver the nucleic acids to cells as described herein include vectors known to those of skill in the art and used for such purposes. Certain exemplary vectors may be plasmids, lentiviruses or adeno-associated viruses known to those of skill in the art. Vectors include, but are not limited to, nucleic acid molecules that are single-stranded, doublestranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, lentiviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." Common expression vectors of utility in recombinant DNA techniques are often in the form of plasmids. Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). Representative AAV viruses include those serotypes known in the art and referred to as AAV1, AAV2, AAV3, AAV4, AAV5, AAV6, AAV7, AAV8, AAV9, AAV10, and AAV11 and as described in the literature.

Methods of non-viral delivery of nucleic acids or native DNA binding protein, native guide RNA or other native species include lipofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424; WO 91/16024. Delivery can be to cells (e.g. in vitro or ex vivo administration) or target tissues (e.g. in vivo administration). The term native includes the protein, enzyme or guide RNA species itself and not the nucleic acid encoding the species.

Regulatory elements are contemplated for use with the methods and constructs described herein. The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector may comprise one or more pol III promoter (e.g. 1, 2, 3, 4, 5, or more pol III promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter and Pol II promoters described herein. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.).

Aspects of the methods described herein may make use of terminator sequences. A terminator sequence includes a section of nucleic acid sequence that marks the end of a gene or operon in genomic DNA during transcription. This sequence mediates transcriptional termination by providing signals in the newly synthesized mRNA that trigger processes which release the mRNA from the transcriptional complex. These processes include the direct interaction of the mRNA secondary structure with the complex and/or the indirect activities of recruited termination factors. Release of the transcriptional complex frees RNA polymerase and related transcriptional machinery to begin transcription of new mRNAs. Terminator sequences include those known in the art and identified and described herein.

EXAMPLE XII

Materials and Methods

Methods described in Example XI use the following general methods.

Genomic PCR: Genomic DNA were extracted from tissues and in vitro cultured cells using Quick Extract solution (Epicenter) according to manufacturer's instruction. DNA samples in Quick Extract of volumes equal to 10% of the final PCR reaction were used. Nested PCR was performed with 20 cycles of first round amplification followed by 25 cycles of second round amplification with a 1:10 dilution between the two rounds. PCR products were used for electrophoresis on 1.5% agarose gel for visualization and on 0.6% agarose gel for gel extraction. Wild-type and exon-excised bands were gel extracted and cloned into TOPO plasmids using ZeroBlunt TOPO kit (LifeTech) and subsequently transformed TOP10 competent cells. Individual colonies were sent for Sanger sequencing to confirm the correct excision of sequence flanked by two guide RNAs.

RT-PCR and Taqman-based Real Time PCR: Total RNA was isolated from tissues using TRIzol reagent (LifeTech) per manufacturer's instructions. For tissues harvested from animals, 1 ug of RNA was used for cDNA synthesis with SuperScript III MasterMix (LifeTech) in 20 uL reactions. For in vitro cultured samples, 400 ng of RNA was used for cDNA synthesis with SuperScript VILO MasterMix (LifeTech) in 20 uL reactions. RT-PCR was performed using luL or abovementioned cDNA with Q5 HotStart MasterMix (New England Biolabs) with DMD RT forward and reverse primer. Both wild-type and exon-skipped bands were gel extracted and cloned into TOPO vectors using ZeroBlunt TOPO kit (LifeTech) and subsequently transformed into TOP10 competent cells. Individual colonies were sent for Sanger sequencing. Alignment to genomic sequence was performed using Geneious software. Taqman quantitative RealTime-PCR was performed as previously described. Taqman assays against exon 4-5, for quantification of total DMD transcripts, and against exon 22-24, for quantification of exon-23-skipped transcripts were used in additional to 18s assay as endogenous control. Assays were carried out in triplicates of 10 uL reactions for each probe and with 20 ng of cDNA input. Taqman Fast Advanced master mix (LifeTech) was used with fast cycling conditions recommended by the manual. Delta-Ct values between exon 4-5 and exon 22-24 were used to quantify the percentage of exon-skipped transcripts in comparison to total DMD transcripts.

Satellite Cell Isolation and Culture: Satellite cell isolation was performed as previously described. For in vitro expansion experiments, CD45-Sca-1-Mac-1-CXCR4+ b1-integrin+ cells were seeded on collagen/laminin-coated plates in F10 (GIBCO) containing 20% horse serum (Atlanta Biologics), 1% penicillin-streptomycin (Invitrogen), and 1% glutamax (Invitrogen). 5 ng/ml bFGF (Sigma) was added to the medium daily. Medium was changed for fresh medium every other day. After 7 days, satellite cells were harvested, cell numbers were counted and cells were re-plated in multiple wells of a 96 well plate for differentiation. The next day, medium was changed to DMEM (GIBCO) containing 2% horse serum (Atlanta Biologics), 1% penicillin-streptomycin (Invitrogen). Cells were fixed after 60 or 72 hr in differentiation medium.

AAV Production: AAVs were generated through the Gene Transfer Vector Core (GTVC) at the Grousbeck Gene Therapy Center at the Schepens Eye Research Institute and Massachusetts Eye and Ear Infirmary (SERI/MEEI).

Western Blotting: Protein was extracted from tissues and cultured cells using RIPA buffer (Cell Signaling). Tissues were homogenized using GentleMACS M-tubes (Miltenyi Biotech) with protein 1.1 program. Protein was concentrated using Amicon Ultra 10k centrifugal filter units. Protein concentration was determined by BCA assay (Pierce). 25 ug, 25 ug and 50 ug of total protein per lane were used for myotubes, IM injected TA muscle and IP injected tissues, respectively. Different percentages of wild-type muscle proteins were diluted in mdx proteins from the same muscle so that the total protein of that lane was kept the same. Samples were denatured at 99° C. for 5 minutes before being loaded on to 4-20% Tris-HC1 precast Criterion gels (Bio-Rad).

Dystrophin and GAPDH (loading control) were detected by primary antibodies NCL_DYS1 (1:100, Novocastra) and sc-32233 (1:25,000, Santa-Cruz Biotechnology) followed by horse anti-mouse IgG HRP-linked (1:1,000, Cell Signaling Technology 7076P2). ChemiDoc imaging system (Bio-Rad) was used to detect chemiluminescence after using SuperDura ECL kit. Intensity of Dystrophin and GAPDH bands were quantified using ImageJ gel analysis function. Different exposures were used for some membranes for Dystrophin and GAPDH quantification to avoid overexposed bands. Relative abundance of Dystrophin in total protein was computed by the ratio of Dystrophin signal and GAPDH and presented in Arbitrary Unit (AU).

Histology: Mouse skeletal and heart muscles were dissected. Samples used for Dystrophin immunofluorescence were embedded in O.C.T compound (Tissue-Tek) right after dissection and frozen in liquid-nitrogen-cold isopentane. Sample used for tdTomato immunofluorescence were fixed in 4% PFA for 1 h at room temperature and immersed in 30% sucrose until submersion, before embedding in O.C.T. and freezing. Subsequent cryosectioning was performed using a Microm HM550 (Thermo Scientific); skeletal muscles were sectioned to a thickness of 12 μm and heart samples were sectioned at 30 μm.

Immunofluorescence: Fixed cryosections were blocked with 5% NGS, 2% BSA, 2% protein concentrate (M.O.M. Kit, Vector Laboratories, BMK-2202), and 0.1% tween-20 at room temp. for 1 h, followed by 3 washes with 1×DPBS for 5 min. each. Sections were subsequently stained with rabbit polyclonal anti-dystrophin (1:50, Abcam, ab15277) or anti-laminin (1:200, Abcam, ab11575) at 4° C. overnight, followed by 3 washes with 1×DPBS for 5 min each. Slides were then incubated with secondary goat-anti-rabbit IgG Alexa Fluor 488 (1:250, Life Technologies) at room temp. for 1 h, followed by 3 washes with 1×DPBS for 5 min. each. Slides were then mounted with mounting media containing DAPI (Vector Laboratories).

Muscle Force Analysis: Mice were anesthetized with sodium pentobarbital (80-100 mg/kg body mass). Supplemental doses were provided as necessary during the experiment. Small incisions were made to expose the right tibialis anterior (TA) tendon and right patellar tendon. The mouse was placed on the temperature controlled platform (38° C.) of an in situ test stand (Aurora Scientific model 809B, Aurora, Ontario, Canada). Silk suture (4-0) was used to attach the severed TA tendon to the lever arm of a dual mode muscle lever system (Aurora Scientific model 305C-LR). The lower right limb was stabilized by using suture attached to the patellar tendon to secure the knee to a horizontal support. Supramaximal 200 μs square-wave pulses, output by a high current muscle stimulator (Aurora Scientific, model 701A), were delivered to platinum electrodes inserted behind the knee to depolarize the peroneal nerve. The lever system was interfaced to a PC using a multi-function data acquisition board (National Instruments model USB-6229, Austin, TX). Custom software written in LabVIEW (National Instruments) was used to configure and trigger stimulation, control lever arm position, and record data to disk. After the right leg was studied, the animal was removed from the test stand and the left leg prepared and studied in an identical manner. All contractile measurements were initiated at the empirically determined optimal length ($L_0$) for tetanic tension (200 Hz stimulation). Fiber length (FL) was calculated as 0.60 $L_0$. Susceptibility to mechanical strain was evaluated by subjecting the muscle to 5 lengthening (eccentric) trials. During each lengthening trial the muscle was tetanically stimulated at $L_0$ for 100 ms and then lengthened to 1.20 FL at a velocity of +1.5 FL/s. Stimulation ceased at the conclusion of the lengthening ramp. The muscle was held for 200 ms before being returned to its $L_0$ at a velocity of −1.5 FL/s. The series of lengthening contractions was bracketed by fixed-end tetanic contractions, which were used to evaluate the overall change in force due to the lengthening contractions. One minute separated all contractions. Specific force was calculated as active tetanic force divided by physiological cross-sectional area (pCSA). The pCSA of the TA was calculated as muscle mass divided by the product of FL and muscle density. Muscle density was taken as 1.06 mg/mm$^3$.

EXAMPLE XIII

CRISPR Activity Reporter System

A CRISPR activity reporter system and related data is depicted in FIGS. 14A-14J. The CRISPER activity reporter system is a programmable system for fluorescent detection and enrichment of gene-edited cells in vitro and in vivo.

Figure 14E:
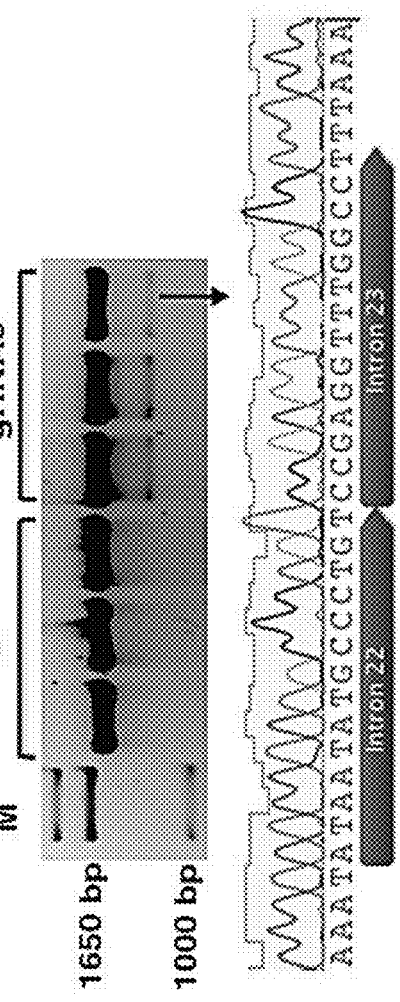
FIG. 14E depicts detection of permanent exon skipping by genomic PCR using primers spanning DMD exon 23. DNA was isolated from myotubes differentiated from sorted tdTomato+ cells derived from satellite cells previously transfected with Sp hCas9 and Ai9 gRNAs (left lanes) or coupled Ai9-DMD23 gRNAs (right lanes). Unedited genomic product, 1572 bp; gene-edited product, 1189 bp. Sanger sequencing trace confirms precise deletion of exon 23 from the genome. (SEQ ID NO:1)
Figure 14F:
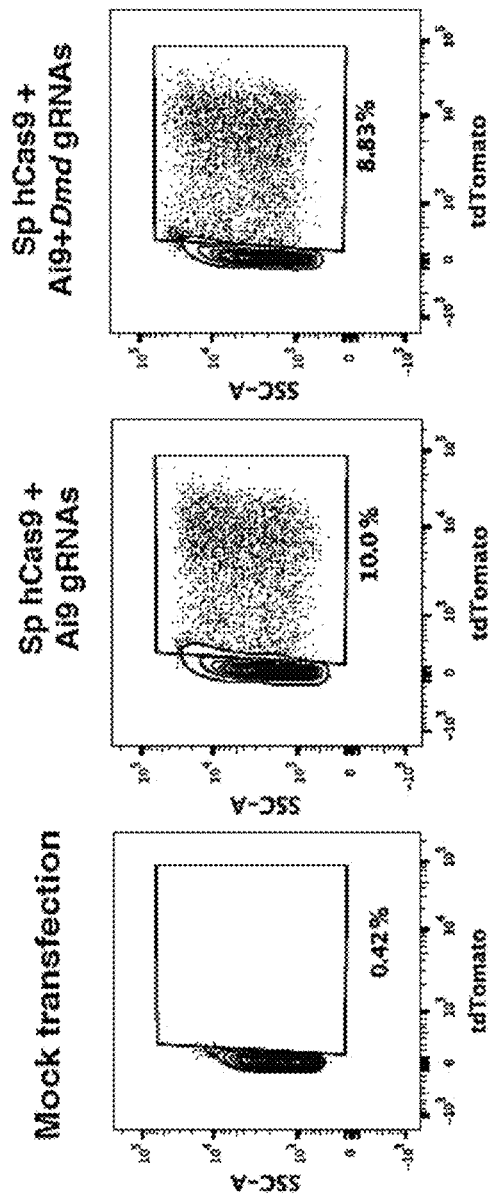
FIG. 14F illustrates FACS plots from mdx;Ai9 satellite cells transfected with plasmids encoding for Sp hCas9 and gRNAs targeting Ai9 locus (middle panel), Sp hCas9 and coupled gRNAs targeting Ai9 and DMD23 loci (right panel) or no plasmids (left panel).

According to certain aspects, a mouse reporter allele, Ai9, encodes the fluorescent tdTomato protein downstream of a ubiquitous CAGGS promoter and "floxed" STOP cassette (See FIG. 14A). Exposure to Cas9, together with paired gRNAs targeting near the 5' and 3' of loxP sites of the Ai9 allele (hereafter Ai9 gRNAs), results in precise excision of the intervening DNA and expression of the downstream tdTomato gene. This Ai9 CRISPR system thus provides sensitive, fluorescence-based detection of CRISPR activity with single cell resolution and the capacity to prospectively detect and isolate gene-edited cells by fluorescence activated cell sorting (FACS). A pair of gRNAs directed at 5' and 3' sequences flanking exon 23 of the mouse Dmd gene (hereafter Dmd23 gRNAs) were designed and tested and which enabled efficient excision of the intervening DNA. Mdx mice, which provide a genetic model of human DMD, carry a nonsense mutation in exon 23 of the Dmd gene, resulting in loss of Dystrophin protein and destabilization of DMD mRNA. According to methods described herein, skipping of exon 23 restores Dystrophin reading frame and results in production of an internally truncated, but still highly functional protein that can complement dystrophin-deficiency in dystrophic muscle. To facilitate detection of DMD gene-edited cells, the Dmd23 gRNAs were coupled to Ai9 gRNAs using a two plasmid system in which the 3' gRNAs for Ai9 and Dmd were encoded in one vector and the 5' gRNAs in another vector. This hybrid vector system effectively links expression of the CRISPR activity reporter (tdTomato) to genome editing events at the Dmd locus, because in order to express tdTomato after co-transfection with these gRNA vectors and Sp humanized Cas9 (Sp hCas9), the target cell must have received both the 5' and 3' Ai9 gRNAs, and therefore also must have received both of the linked Dmd23 gRNAs. In vitro transfection of primary satellite cells from mdx mice carrying the Ai9 allele (hereafter referred to as mdx;Ai9 mice) with Sp hCas9+Ai9-Dmd23 coupled gRNAs induced gene editing at both the Ai9 locus (demonstrated by tdTomato expression, FIG. 14F, right panel) and Dmd locus (detected by genomic PCR using primers flanking exon 23 and sequencing of amplions, which indicated precise excision and generation of a hybrid intron fusing introns 22 and 23, FIG. 14E). DMD gene editing was not seen in mdx;Ai9 cells receiving Ai9 gRNAs alone (FIG. 14E), although tdTomato expression was equivalently induced (FIG. 14F, middle panel), confirming that locus specificity in this system is determined by the genomic complementarity of the gRNAs used for programming Cas9.

Figure 14G:
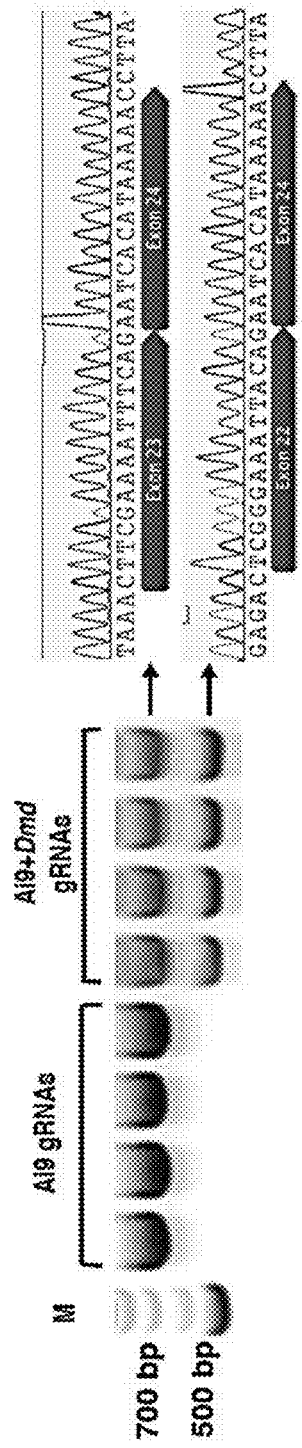
FIG. 14G depicts detection of exon 23-skipped mRNA using RT-PCR. M, molecular weight ladder, Unedited RT-PCR product 738 bp; exon skipped product 525 bp. Analysis of four representative cultures is shown for each set of gRNAs. Sanger sequencing traces confirms precise deletion of exon 23 from the mRNA. (SEQ ID NO:2-3)
Figure 14H:
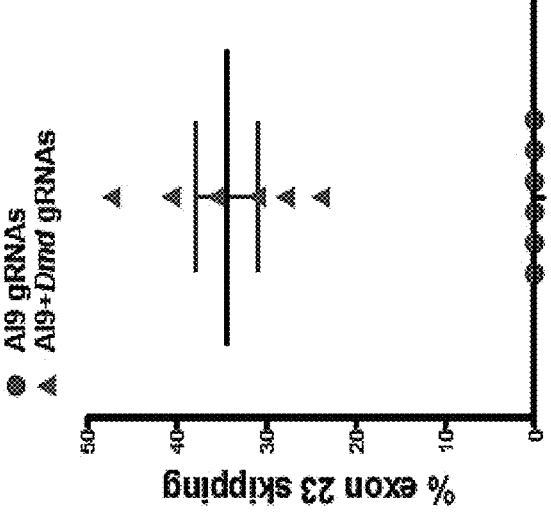
FIG. 14H graphically depicts the quantification of percent exon skipping in targeted satellite cell-derived myotubes by Taqman-based qPCR.
Figure 14I:
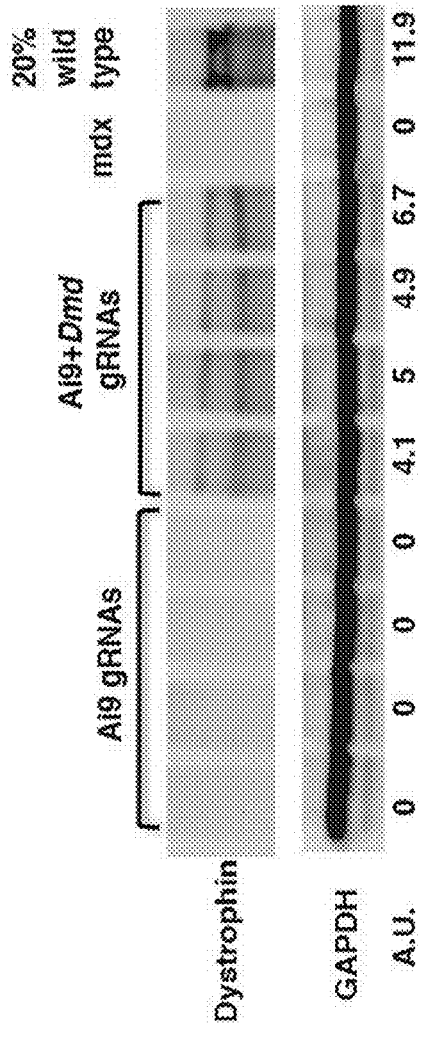
FIG. 14I depicts the Western blot for Dystrophin and GAPDH (loading control) in lysates of myotubes derived from gene-edited satellite cells. Analysis of four representative cultures is shown for each set of gRNAs, compared to lysates from cultures containing 100% unedited mdx myotubes or 80% mdx+20% wild-type myotubes. Signal intensity is quantified by densitometry at the bottom. A.U.: Arbitrary Unit normalized to GAPDH.
Figure 14J:
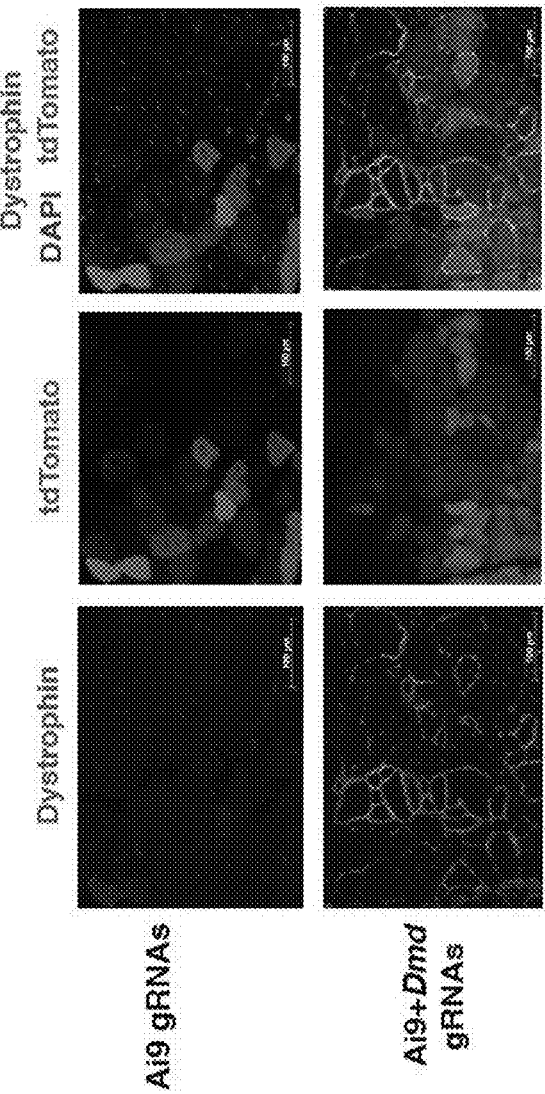
FIG. 14J illustrates dystrophin immunofluorescence in mdx muscles transplanted with satellite cells targeted with Sp hCas9+Ai9 gRNAs (top) or Sp hCas9+Ai9-DMD23 coupled gRNAs (bottom). Green, dystrophin; red, tdTomato; blue: DAPI. Scale bar: 100 um.

To confirm that CRISPR-mediated editing of the DMD locus results in permanent genomic modification and production of exon skipped mRNA and protein, co-transfected primary satellite cells were FACSorted based on tdTomato expression, expanded in vitro, and differentiated to myotubes. RNA and protein were then harvested for standard RT-PCR and sanger sequencing analysis, which demonstrated the presence of the exon 23 skipped Dmd mRNA in cells receiving Sp hCas9 and coupled Ai9-Dmd23 gRNAs, but not in cells receiving Sp hCas9 and Ai9 gRNAs only (FIG. 14G). Sequencing of the exon skipped amplicon confirmed the production of an in-frame transcript that juxtaposes exons 22 and 24. Levels of exon skipped transcripts were quantified using Taqman analysis, and represented 24-47% of total DMD mRNA in cells receiving Ai9-Dmd23 coupled gRNAs (FIG. 14H). In contrast, exon skipping was undetectable in cells receiving Sp hCas9 with only Ai9 gRNAs (FIG. 14H). Dystrophin protein expression was also restored in CRISPR-modified mdx;Ai9 cells, and was detectable by Western blot (FIG. 14I) in in vitro differentiated myotubes and immunofluescence in in vivo engrafted muscle fibers derived from gene edited satellite cells (FIG. 14J).

EXAMPLE XIV

Delivery of a CRISPR System Using AAV

Aspects of the present disclosure are directed to methods of delivering a Cas9 protein and guide RNA to a cell, including a cell within an individual, using a viral vector, such as an adeno-associated virus. AAVs are currently in use in human clinical trials and provide the opportunity for both local and systemic delivery of virally encoded gene editing complexes. Given the limited packaging capacity (4.8 kb) of AAVs, the orthologous Cas9 protein from *Streptococcus aureus* (Sa), which is ~1 kb smaller than Sp Cas9, and can target any desired locus in the genome containing a "NNGRRT" PAM sequence was used. To also employ tdTomato expression as a reporter of in vivo CRISPR activity, paired Sa gRNAs targeting sequences flanking the STOP cassette of the Ai9 allele were generated. Using the Ai9 CRISPR activity reporter, the SaCas9 gRNA scaffold was optimized by incorporating base modifications that have been reported to remove a putative RNA polymerase III transcription terminator and enhance the assembly of gRNA and catalytically inactive orthologous Sp Cas9. The same base modifications in the gRNA scaffold that increase the efficiency of Sp CRISPR complex formation also enhance gene targeting by SaCas9 (See FIG. 18A-18C). The optimized Sa gRNA scaffold was used to generate Dmd23 Sa gRNAs. 16 pairs of Dmd23 Sa gRNAs were screened and the pair with highest efficiency for precise DNA excision at exon 23 (see FIG. 18D) was identified. AAV constructs were produced encoding SaCas9 and Ai9 Sa gRNAs or Dmd23 Sa gRNAs in two different vectors (FIG. 19A) or a single vector (FIG. 19B). Two different small promoters (173CMV or elongation factor 1α short (EFS)) were used to drive expression of SaCas9 in the single vector CRISPR constructs, while SaCas9 was expressed from the SV40 enhancer and CMV promoter in the dual vector system. Dual or single CRISPR AAV constructs targeting Dmd23 (AAV-Dmd CRISPR) were used to generate AAV serotype DJ and transduce myotubes derived from mdx primary satellite cells in order to compare the efficiency of different constructs for inducing exon skipping. Quantification of exon skipping in transduced mdx myotubes showed that dual AAV constructs induce exon skipping more efficiently than the single vector constructs and that EFS-driven SaCas9 is more efficient than 173CMV-driven SaCas9 (FIG. 19C). Though both the single vector system and the two vector system produced exon skipping, the dual vector system was selected for in vivo Dmd targeting according to the methods described herein. Accordingly, methods described herein are directed to a first AAV constructs encoding SaCas9 and Ai9 Sa gRNAs and a second AAV construct encoding SaCas9 and Dmd23 Sa gRNAs. The first and second AAV constructs are introduced to a cell.

EXAMPLE XV

In Vivo Delivery of a CRISPR System Using AAV

Aspects of the present disclosure are directed to methods of gene editing by injecting a Cas9/guide RNA system encoded into one or more AAV vectors into muscle of an animal. For in vivo injections, dual AAVs were pseudotyped to serotype 9, which exhibits robust transduction of mouse skeletal and cardiac muscle. The tibialis anterior (TA) muscles of mdx;Ai9 mice were injected with AAV9-SaCas9+AAV9-Ai9 gRNAs (7.5E+11 vg each) or vehicle to test the potential for in vivo targeting of an endogenous gene in multinucleated muscle fibers. Four weeks later, muscles were harvested for immunofluorescence to assess genomic editing events. TdTomato fluorescence was detected in muscles injected with AAV-Ai9 CRISPR, but not in muscles injected with vehicle alone (FIG. 15A) demonstrating precise genome editing in multinucleated skeletal muscle fibers after in vivo delivery of CRISPR AAV.

Figure 15E:
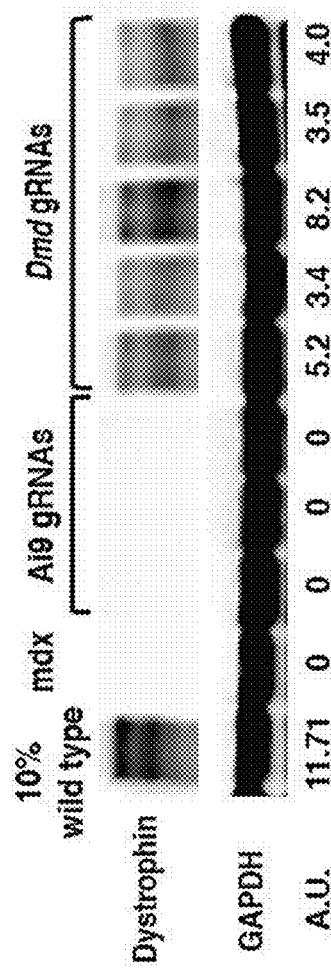
FIG. 15E illustrates the Western blot for Dystrophin and GAPDH (loading control) in muscles injected with AAV-CRISPR using Ai9 (left) or DMD (right) gRNAs, quantified by densitometry at the bottom. A.U.: Arbitrary Unit normalized to GAPDH.
Figure 15F:
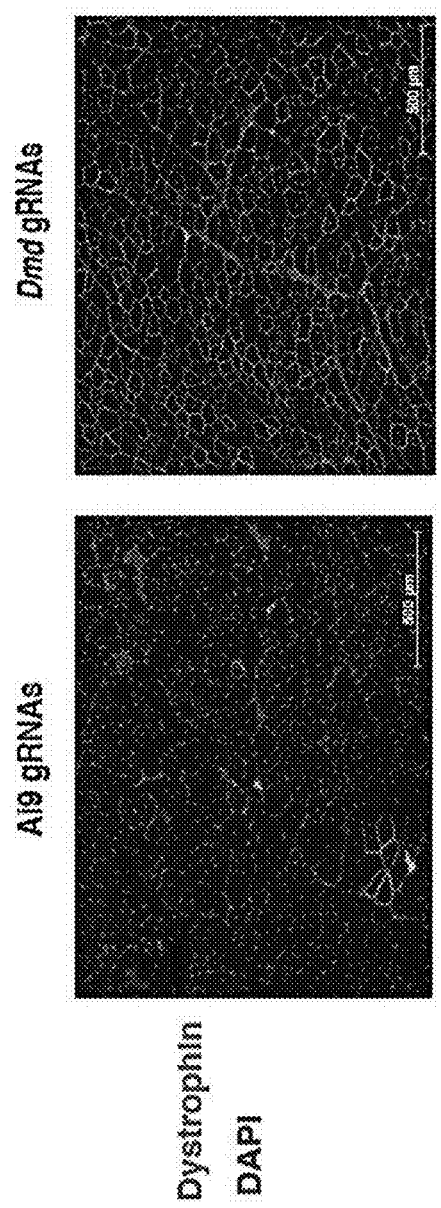
FIG. 15F displays images of immunofluorescence staining for Dystrophin (green) in mdx;Ai9 muscles injected with CRISPR AAVs targeting Ai9 (Left) or DMD23 (Right).

Similar to targeting at the Ai9 locus, co-delivery of AAV9-SaCas9+AAV9-Dmd23 gRNAs resulted in robust and specific modification of the Dmd locus in skeletal muscles in vivo. Genomic PCR and sanger sequencing demonstrated precise excision of exon 23 in muscles of mice injected with AAV9-SaCas9+AAV9-Dmd23 gRNAs, but not AAV9-Sa Cas9+AAV9-Ai9 gRNAs (FIG. 15B). Consistent with genomic data, RT-PCR and sanger sequencing analysis demonstrated the presence of exon skipped DMD mRNA specifically in muscles receiving AAV9-SaCas9+AAV9-Dmd23 gRNAs (FIG. 15C). Quantification of exon skipping efficiency by Taqman indicated an average targeting rate of 39% (+/−8.3%) (FIG. 15D). As seen for targeting of primary satellite cells in culture, local, in vivo CRISPR-based editing of skeletal muscle restored expression of Dystrophin protein, which was detected by Western blot (FIG. 15E) and present at the surface of muscle fibers of mdx;Ai9 mouse muscle for at least four weeks after transduction with AAV-Dmd CRISPR (FIG. 15F). In contrast, Dystrophin expression was undetectable by Western blot (FIG. 15E) and present only on rare revertant fibers (FIG. 15F) in mdx;Ai9 mice receiving control Ai9 gRNAs.

EXAMPLE XVI

In Situ Muscle Force Assessment

Figures 15G, 15H:
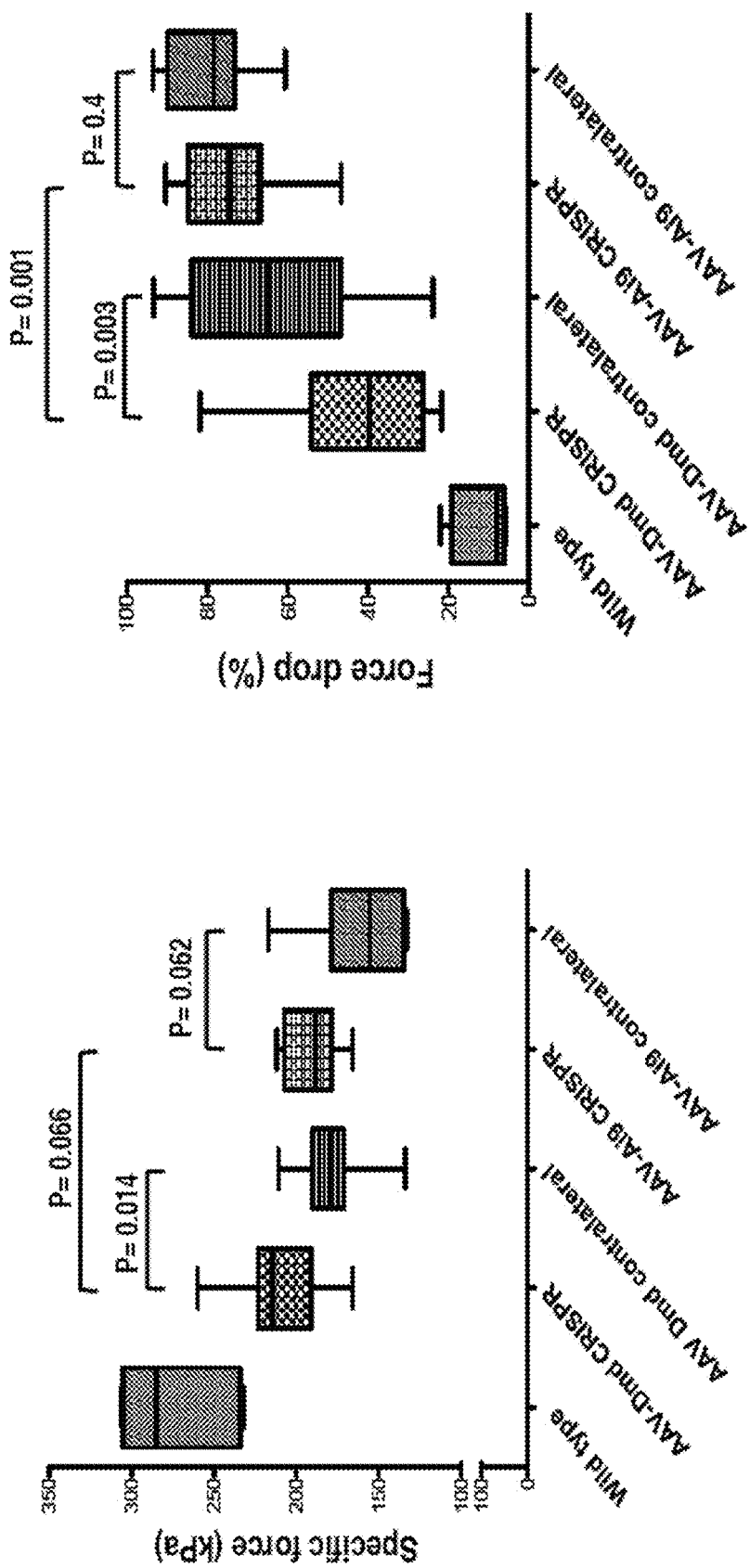
FIG. 15G graphically depicts the analysis of muscle specific force, and FIG. 15H graphically depicts the decrease in force after eccentric damage n=6 for wild type mice injected with vehicle, n=9 for mdx;Ai9 mice injected with AAV-DMD CRISPR in the right leg and vehicle in the left leg and n=8 for mdx;Ai9 mice injected with AAV-Ai9 CRISPR in the right leg and vehicle in the left leg. P-values calculated by paired student t-test for comparing contralateral legs and unpaired student t-test for comparing muscles from different mice.

To evaluate the functional consequences of CRISPR-mediated induction of exon-skipped DMD mRNA in mdx muscle, a subset of mice injected intramuscularly with AAV-Dmd23 CRISPR were subjected to in situ muscle force assessment. Muscles injected with AAV9-SaCas9+AAV9-Dmd23 showed significantly increased specific force (FIG. 15G), and attenuated force drop after eccentric damage (FIG. 15H) compared to the contralateral vehicle injected muscle, demonstrating a therapeutic benefit of permanent exon skipping in the mdx model. In contrast, differences in specific force (FIG. 15G) and force drop (FIG. 15H) for AAV9-SaCas9+AAV9-Ai9 gRNAs injected mice were not statistically significant between the virus-injected and vehicle-injected muscles. According to certain aspects, CRISPR/Cas9 gene editing systems and methods described herein are effective for in vivo genomic modification, including the introduction of therapeutic gene deletions, even in highly multinucleated, post-mitotic cell types such as muscle fibers. The CRISPR-Cas9 system enables permanent modification of the targeted loci, providing enduring production of the modified gene product for as long as the targeted cell/nucleus survives.

EXAMPLE XVII

Systemic Delivery of Gene Editing Complex

Figure 16A:
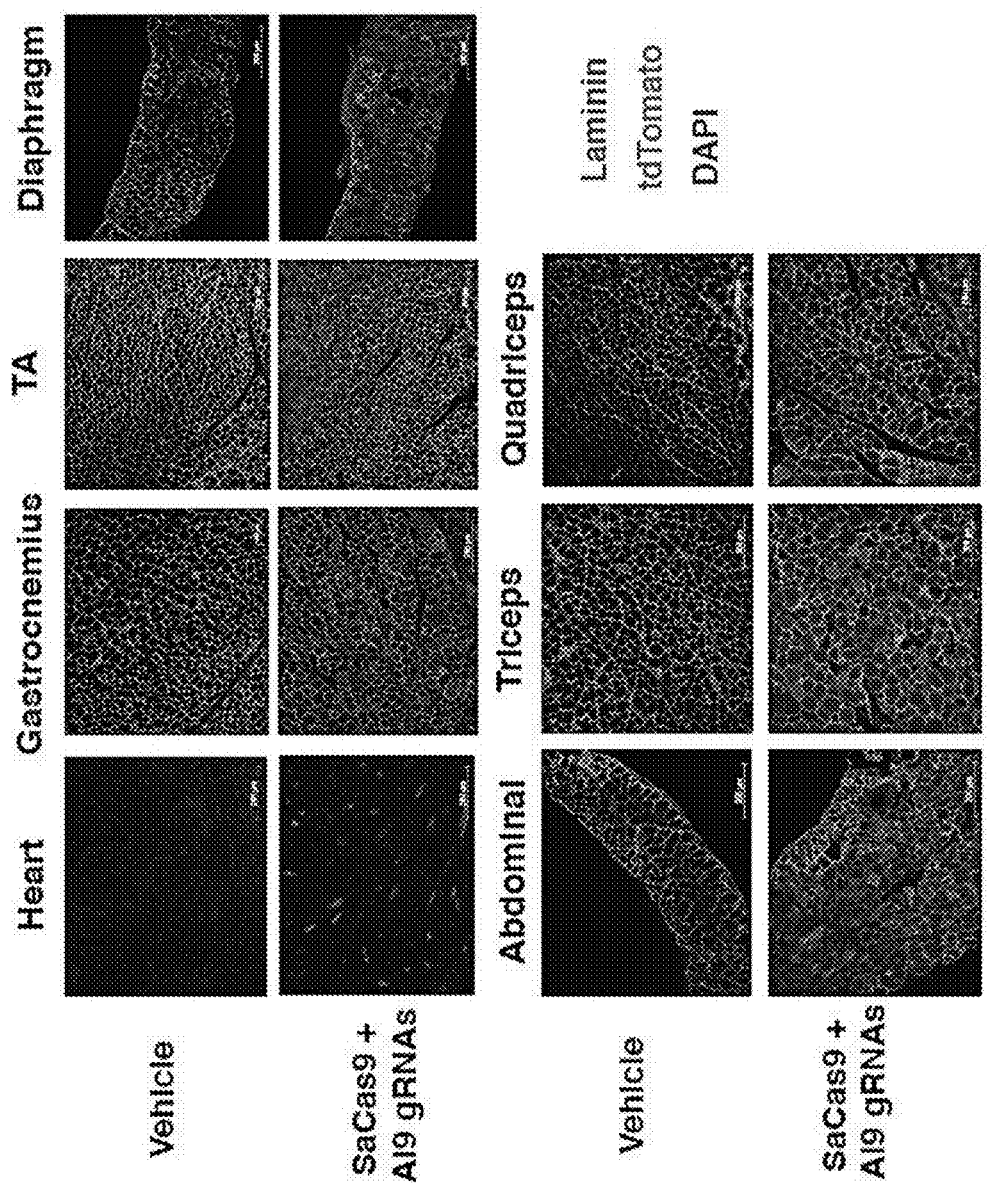
FIG. 16A illustrates representative immunofluorescence analysis of different muscles from 3 weeks old mdx;Ai9 mice injected systemically with vehicle or dual AAVs encoding for SaCas9 and Ai9 gRNAs on P3. The dual AAV-CRISPR system efficiently targets the Ai9 locus in neonatal dystrophic muscle after systemic injection, resulting in tdTomato expression (red). Individual muscle fibers are marked by laminin (green), and nuclei by DAPI (blue). Scale bar: 200 um.
Figure 16B:
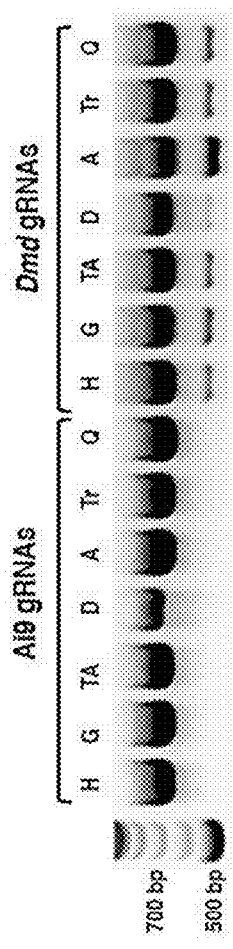
FIG. 16B depicts the detection of exon skipping by RT-PCR using primers spanning DMD exon 23. RNA was isolated from the indicated tissues of mdx;Ai9 mice injected intraperitoneally with AAV-SaCas9+AAV-Ai9 (left) or AAV-DMD23 (right) gRNAs. Exon 23-skipped mRNA is detected only in muscles receiving AAV-DMD23 gRNAs.
Figure 16C:
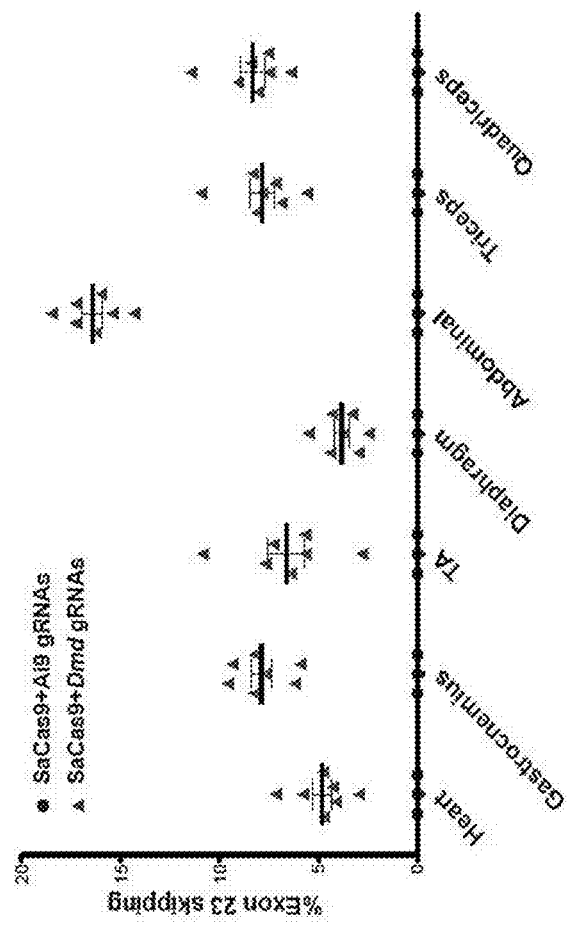
FIG. 16C graphically depicts the quantification of exon skipping in injected muscles by Taqman assay.
Figure 16D:
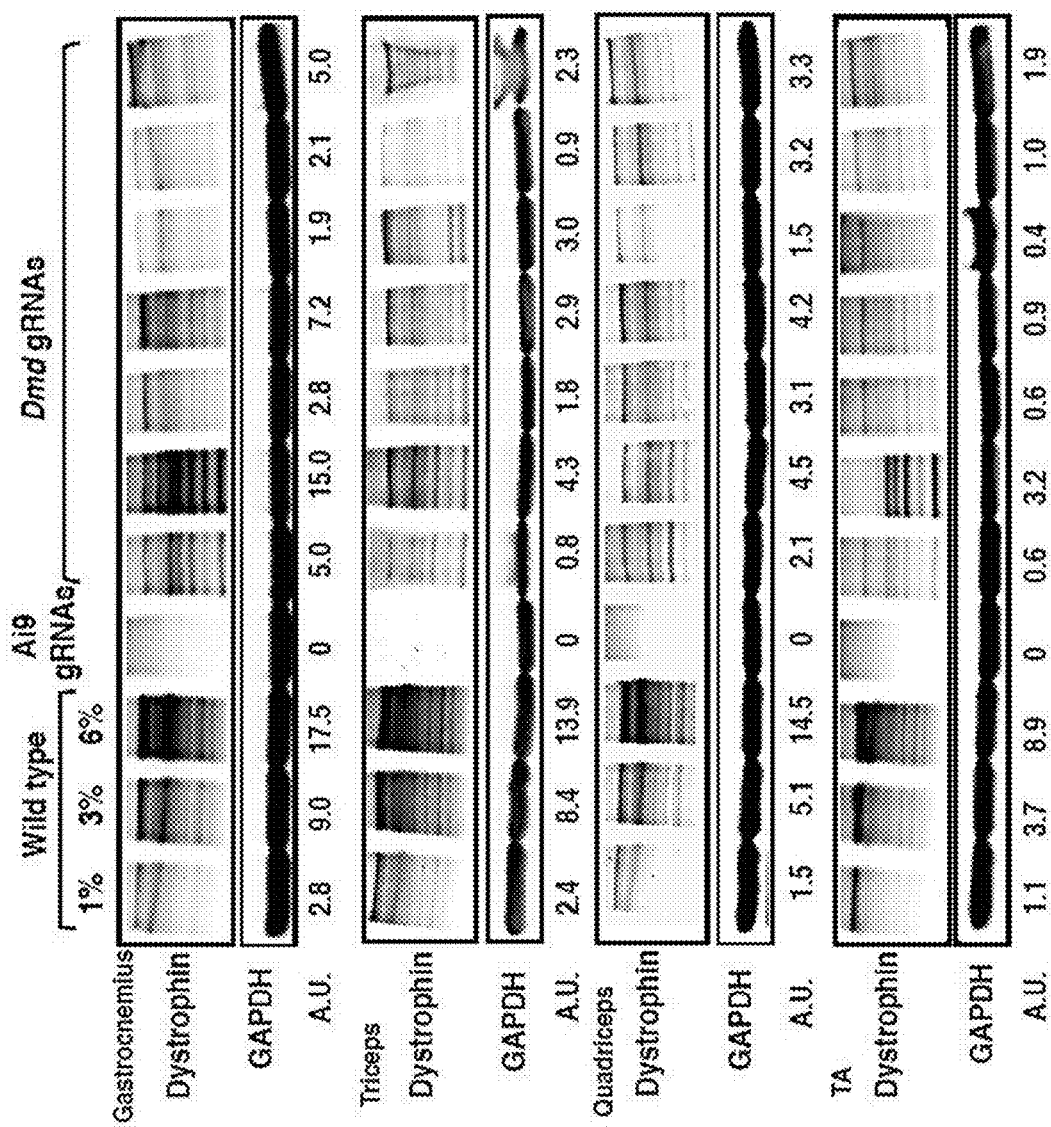
FIG. 16D depicts the detection of Dystrophin and GAPDH (loading control) by Western blot in the indicated muscles of mdx;Ai9 mice receiving systemic AAV-CRISPR. Right lanes correspond to muscles from 7 different mice injected systemically with AAV-DMD CRISPR. Signal intensity is quantified by densitometry at the bottom. A.U.: Arbitrary Unit normalized to GAPDH.
Figure 16E:
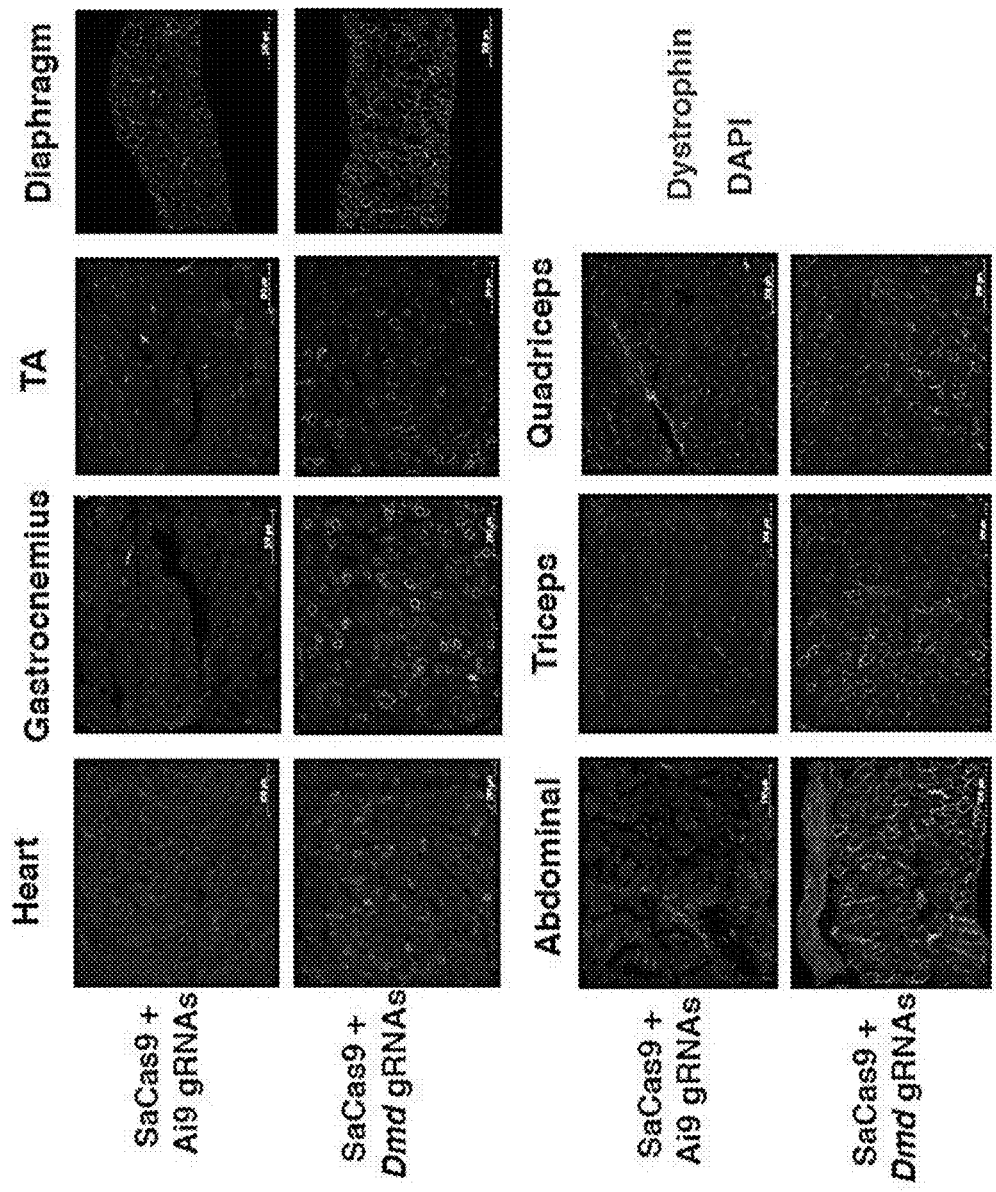
FIG. 16E displays the representative images of immunofluorescence staining for Dystrophin (green) in mdx;Ai9 muscles injected with CRISPR AAVs targeting Ai9 or DMD23. Scale bar: 200 um.
Figure 19A:
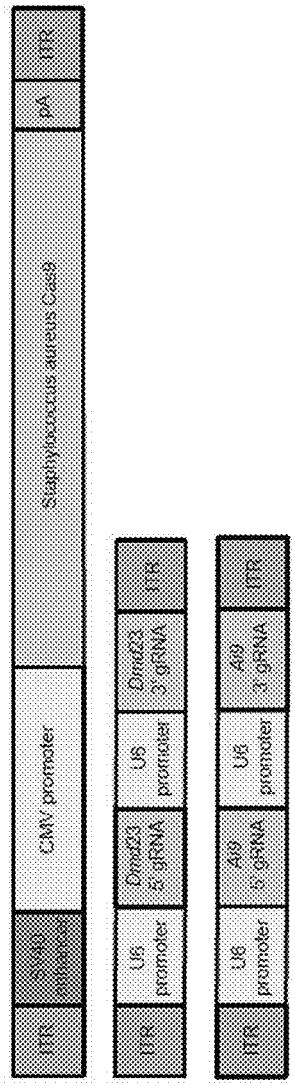
FIG. 19A depicts the schematics of AAV-SaCas9 (top) AAV-DMD23 gRNAs (middle) and AAV-Ai9 gRNAs (bottom) constructs used for dual CRISPR AAV experiments.
Figure 19B:
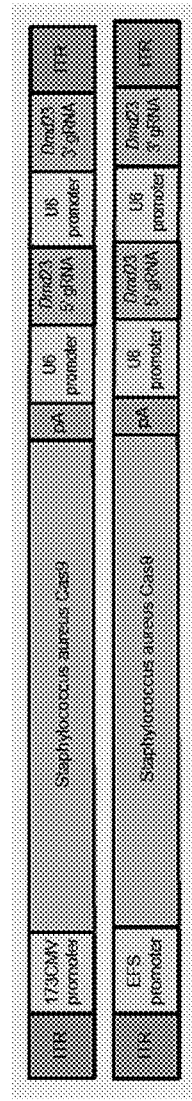
FIG. 19B depicts the schematic of 173CMV_SaCas9_DMD23 gRNAs and EFS_SaCas9_DMD23 gRNAs single AAV constructs.
Figure 19C:
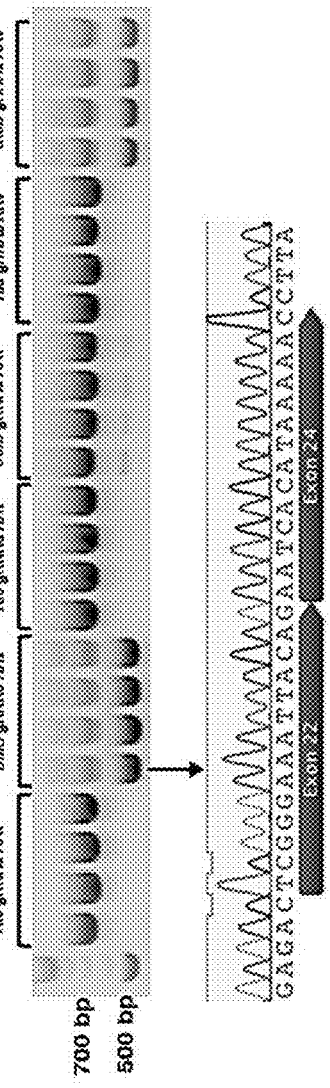
FIG. 19C is an image of the detection of exon skipping by RT-PCR using primers spanning DMD exon 23. RNA was isolated from mdx;Ai9 in vitro differentiated myotubes, transduced with AAV DJ encoding the indicated constructs. Exon 23-skipped mRNA is detected only in myotubes receiving AAV-DMD CRISPR. Sequencing result from unedited and exon skipped mRNA, confirms skipping of exon 23 in the mRNA. (SEQ ID NO:13)
Figure 19E:
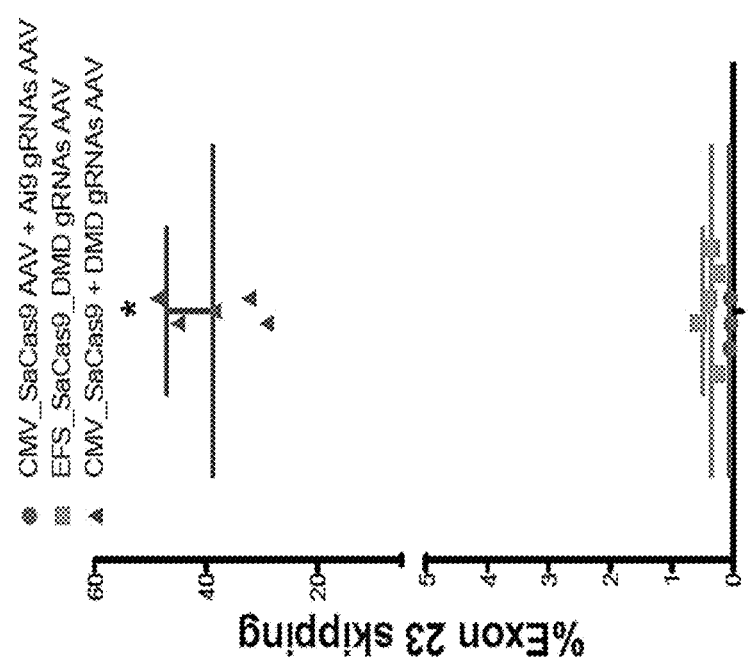
FIG. 19E graphically depicts Taqman-based quantification of exon skipping in muscles injected locally with dual AAVs encoding SaCas9+DMD23 gRNAs or a single AAV encoding EFS_SaCas9_DMD23 gRNAs. *: P<0.05.
Figure 19D:
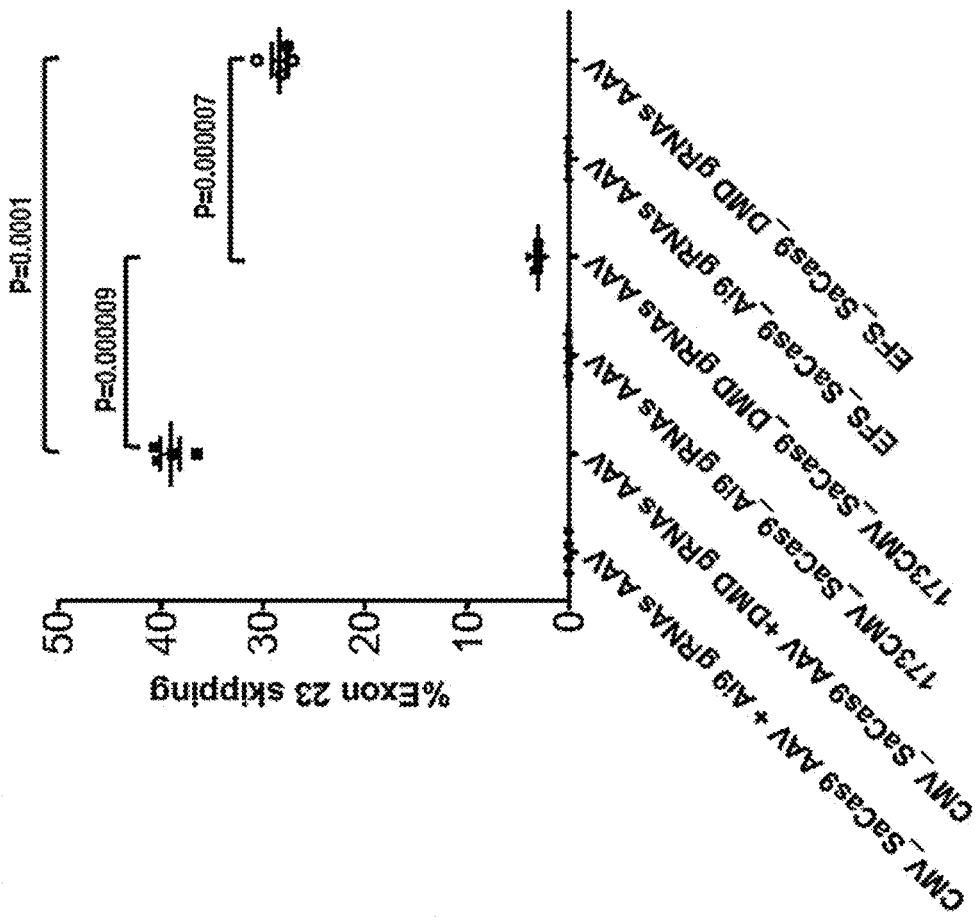
FIG. 19D graphically depicts Taqman-based quantification of exon skipping in myotubes transduced with AAV DJ encoding dual or single DMD23 CRISPR constructs.
Figure 19F:
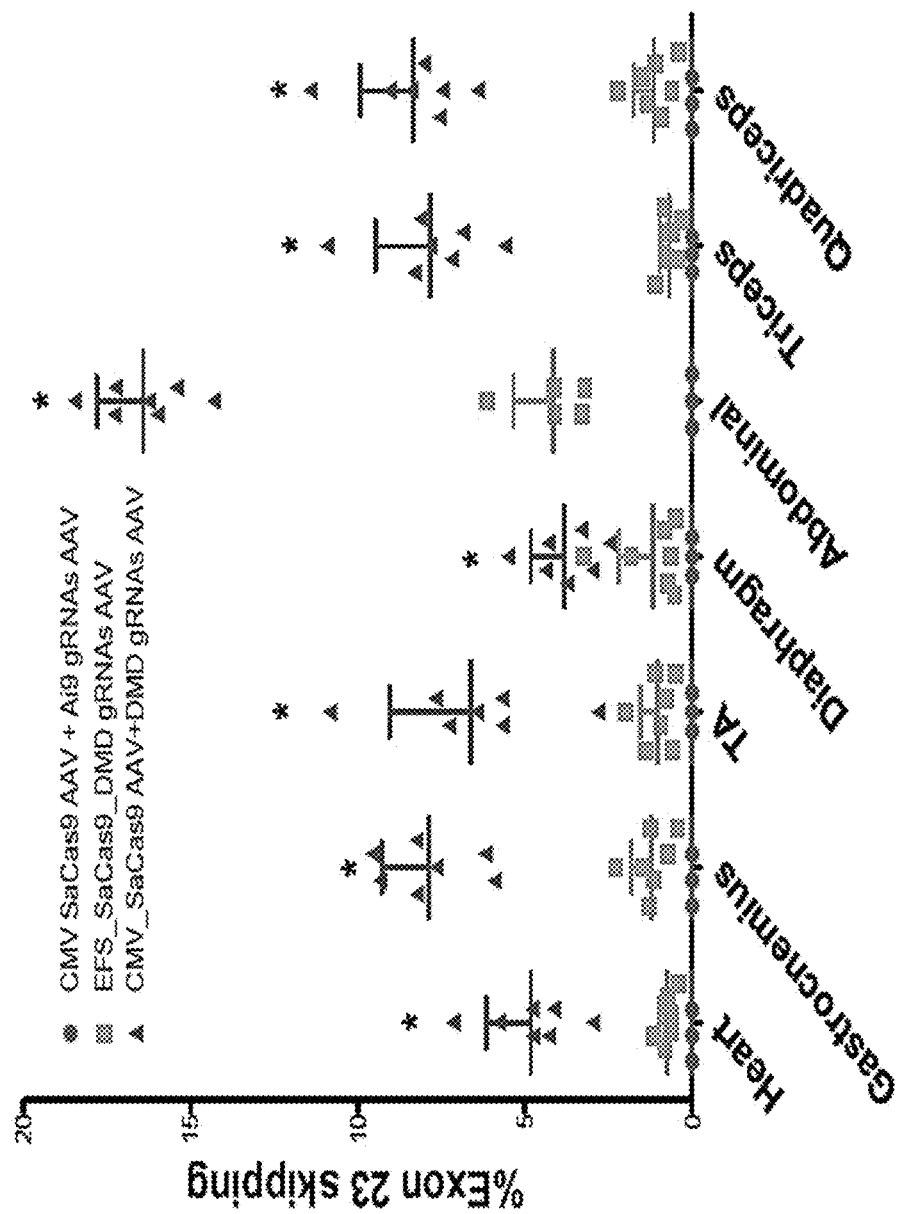
FIG. 19F graphically depicts Taqman-based quantification of exon skipping in different muscles of mice systemically injected with dual AAVs encoding SaCas9+DMD23 gRNAs or a single AAV encoding EFS_SaCas9_DMD23 gRNAs. *: P<0.05.
Figure 20A:
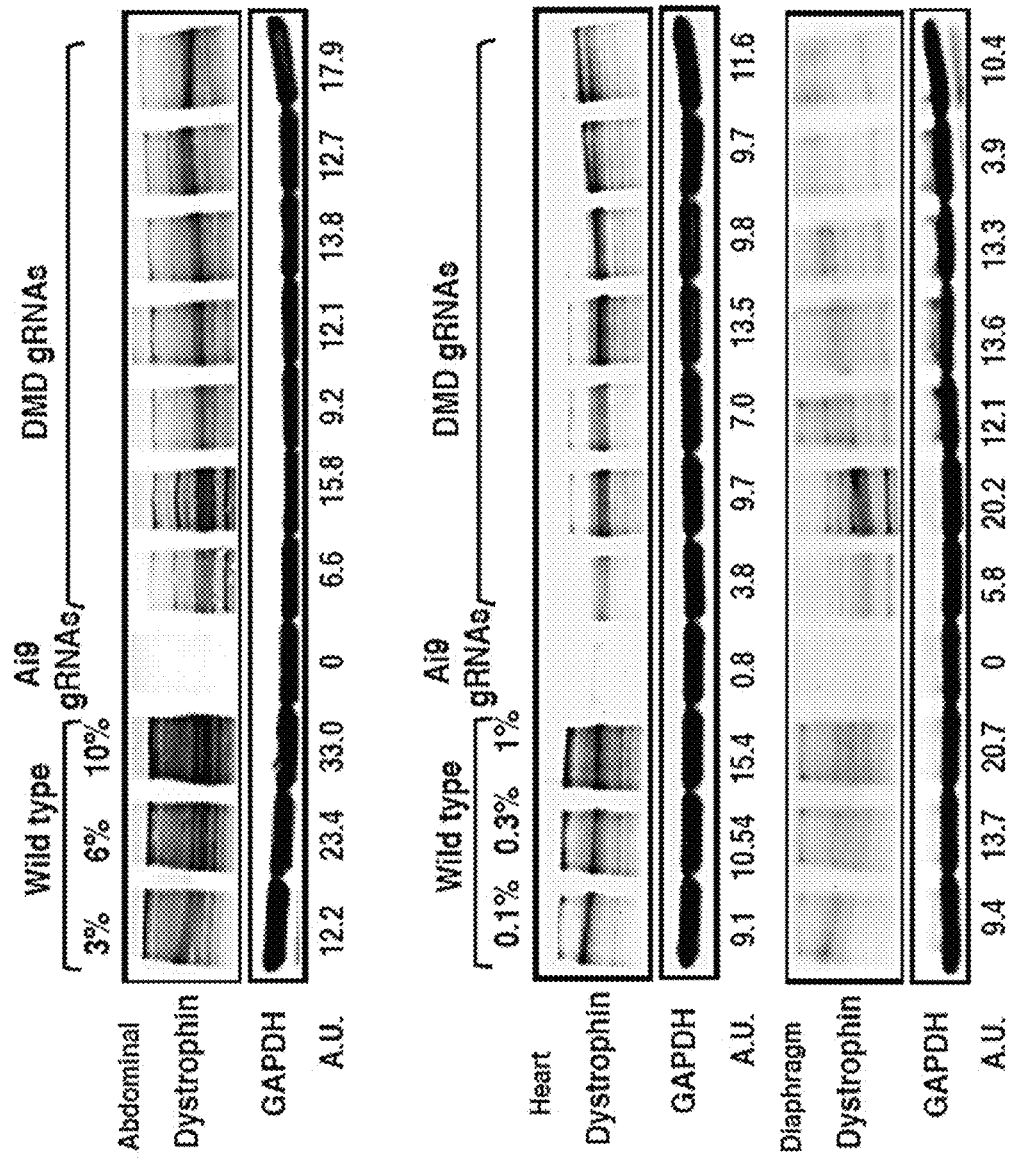
FIG. 20A is an image of the detection of Dystrophin and GAPDH (loading control) by Western blot in the abdominal (top), heart (middle) and diaphragm (bottom) muscles of mdx;Ai9 mice receiving systemic AAV-CRISPR. Right lanes correspond to muscles from 7 different mice injected systemically with AAV-DMD CRISPR. Signal intensity is quantified by densitometry at the bottom. A.U.: Arbitrary Unit normalized to GAPDH.
Figure 20B:
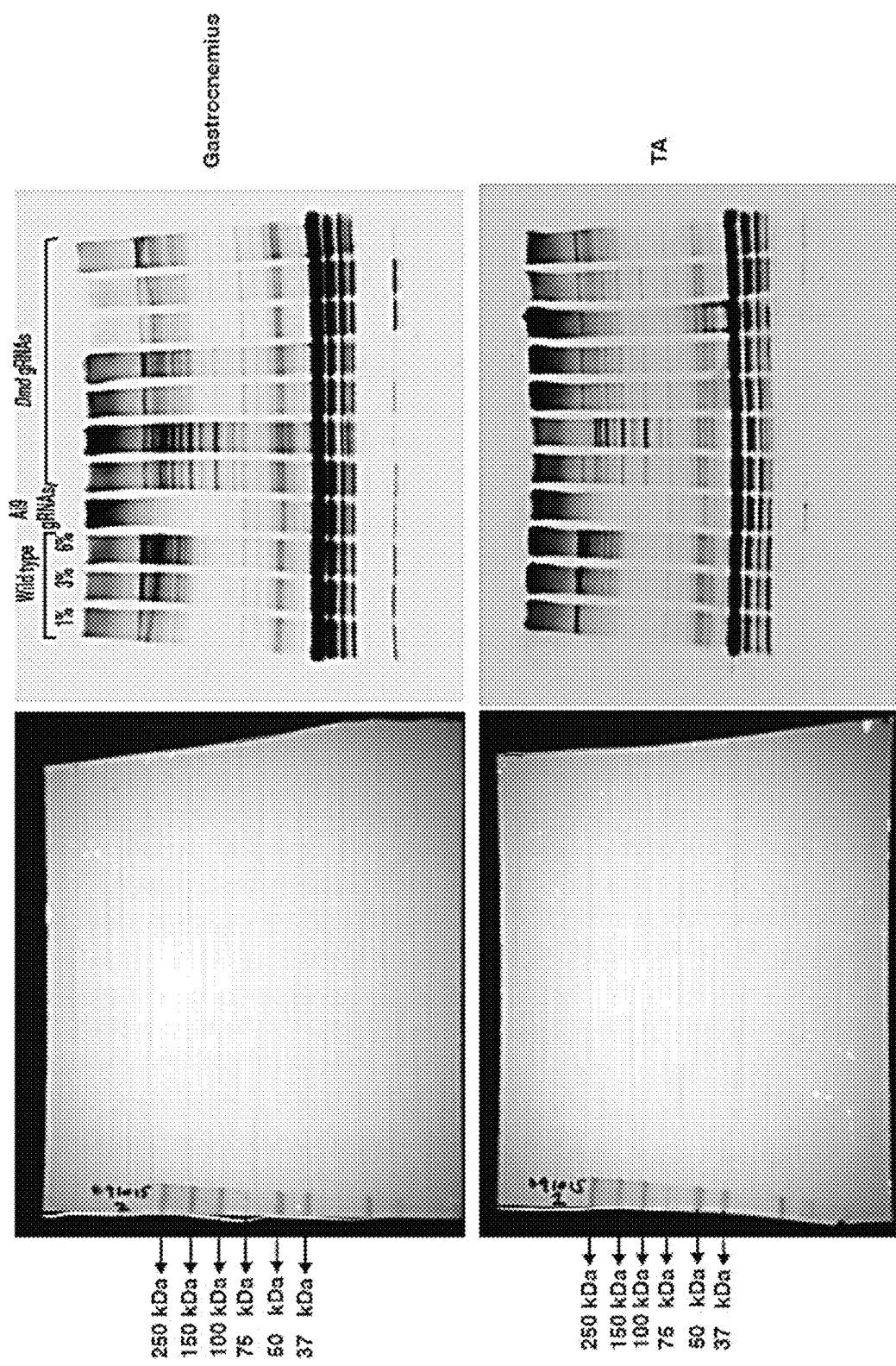
FIG. 20B includes Brightfield (left) and chemiluminescent (right) images of uncropped Dystrophin and GAPDH Western blots from gastrocnemius (top) and TA (bottom) muscles of mice systemically injected with AAV CRISPR.

Methods described herein restore Dystrophin expression after intramuscular delivery of AAV-Dmd CRISPR in mdx mice. Aspects of the present disclosure also include systemic administration of a Cas9/guide RNA system using an AAV. According to this aspect, dual AAV9 vectors (1.5E+12 vg each) were co-injected intraperitoneally into mdx;Ai9 mice at postnatal day 3 (P3). 3 weeks later, muscles were harvested and analyzed for locus-specific gene targeting. RT-PCR and sanger sequencing demonstrated detectable exon 23 skipping in multiple skeletal muscles and cardiac muscle of mice receiving systemic AAV9-SaCas9+AAV9-Dmd23 gRNAs. In contrast, no exon skipping was apparent in dystrophin mRNA in animals receiving Ai9 gRNAs instead (FIG. 16B). Quantification of exon skipped transcripts as a percentage of total DMD mRNA confirmed widespread targeting in animals receiving systemic AAV9-SaCas9+AAV9-Dmd23 gRNAs, with levels varying from 3-18% in different muscle groups (FIG. 16C). Finally, Western blot (FIG. 16D and FIG. 20) and immunofluorescence analysis (FIG. 16E) of Dystrophin protein expression, which is normally lacking in mdx mice and absent from cardiac and skeletal muscles of mdx;Ai9 mice receiving AAV9-SaCas9+AAV9-Ai9 gRNAs, showed restoration of Dystrophin in mice receiving AAV9-SaCas9+AAV9-Dmd23 gRNAs in all muscle groups examined Levels of Dystrophin protein in dual AAV-Dmd CRIPSR treated mice varied among individual mice and muscle groups, with amounts as high as 5% and as low as <0.1% of wild-type. Local and systemic injection of the single vector AAV-Dmd CRISPR, in which SaCas9 is expressed under the control of the EFS promoter, yielded lower exon skipping efficiencies compared to the dual AAV-Dmd CRISPR system (FIGS. 19E and 19F).

EXAMPLE XVIII

Targeting of Satellite Cells In Vivo

According to certain aspects, a Cas9/guide RNA system encoded into one or more AAV vectors is targeted to stem cells (satellite cells) where the target gene is edited in the stem cell (satellite cell). According to certain aspects, dystrophic pathology and other acute and chronic muscle injuries activate satellite cells, leading to muscle regenerative responses that add new nuclei to damaged fibers. In the context of gene therapy in muscle as described herein, the target gene in the satellite cells is permanently edited/corrected to avoid the addition of new, non-targeted nuclei reducing the fraction of nuclei in muscle fibers producing therapeutic exon skipped mRNAs. According to one aspect, the satellite cells are targeted in vivo for target gene modification or alteration so as to provide continual replenishment of gene-edited myonuclei through normal muscle damage and repair mechanisms.

Figure 17A:
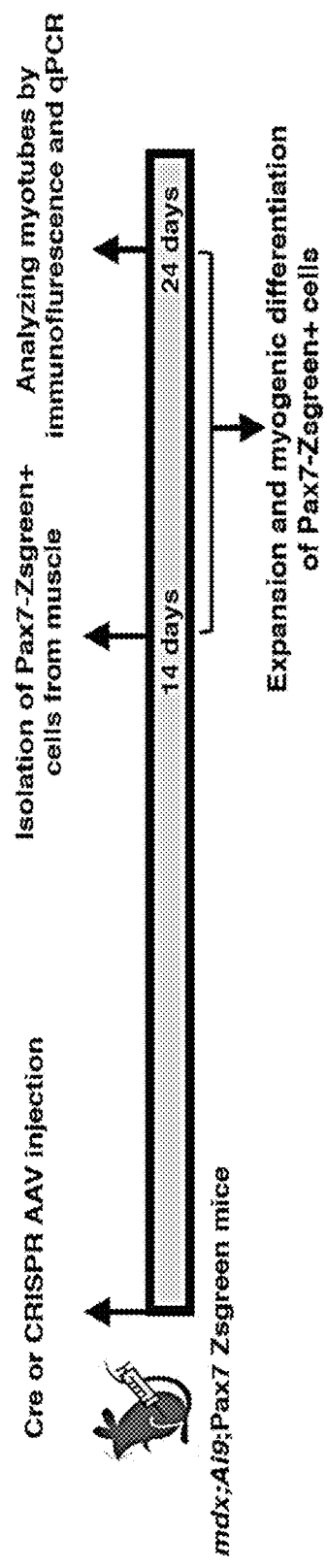
FIG. 17A depicts the experimental design schematic. Pax7-ZsGreen;Mdx;Ai9 mice were injected intramuscularly or intraperitoneally with Cre or CRISPR AAV targeting Ai9 or DMD23. Two weeks later, Pax7+ satellite cells were isolated by FACS, expanded in culture, differentiated to myotubes and analyzed for gene editing.
Figure 17B:
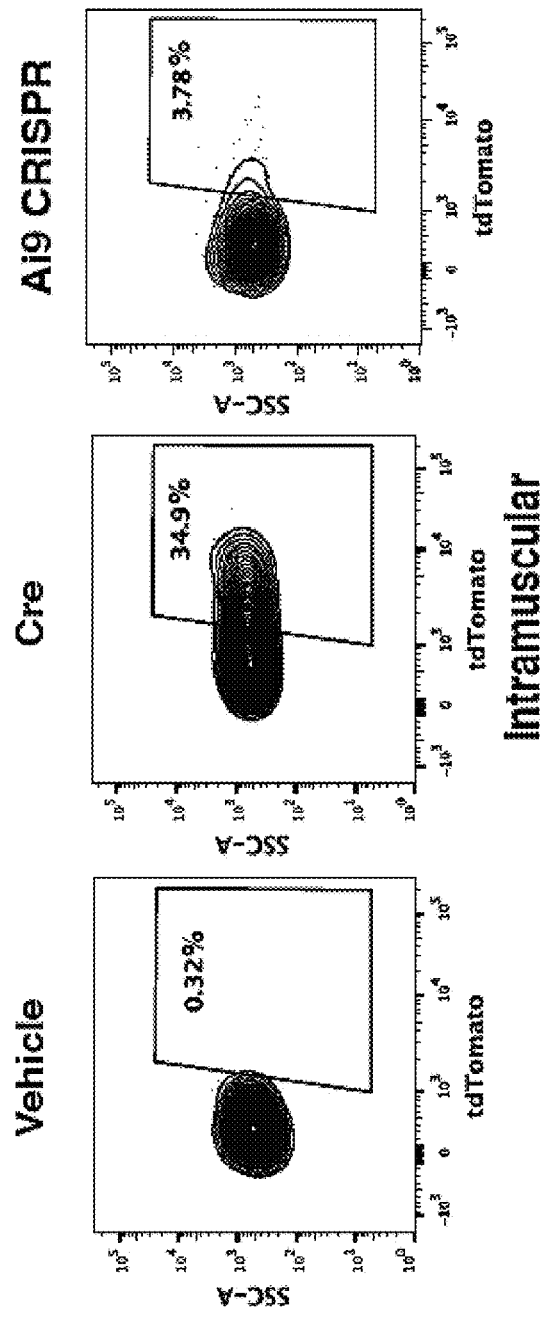
FIG. 17B is representative of FACS plots of tdTomato expression among Zsgreen+ satellite cells isolated from mice injected intramuscularly with vehicle (left), AAV9-Cre (middle) or AAV9-Ai9 CRISPR (right). FACS plots were previously gated for Pax7-ZsGreen positive, Sca1, CD45, Ter119 and Mac 1 negative, live mononuclear cells, and numbers indicate percent tdTomato+ cells for each plot.
Figure 17E:
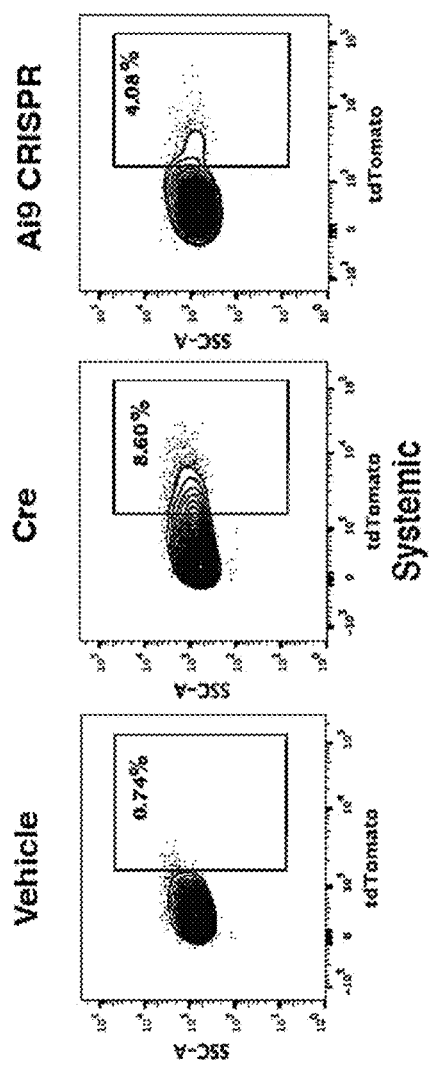
FIG. 17E is representative of FACS plots of tdTomato expression among ZsGreen+ satellite cells isolated from mice injected systemically with vehicle (left), AAV9-Cre (middle) or AAV9-Ai9 CRISPR (right). FACS plots were previously gated for Pax7-ZsGreen positive, Sca1, CD45, Ter119 and Mac1 negative, live mononuclear cells, and numbers indicate percent tdTomato+ cells for each plot.
Figure 17G:
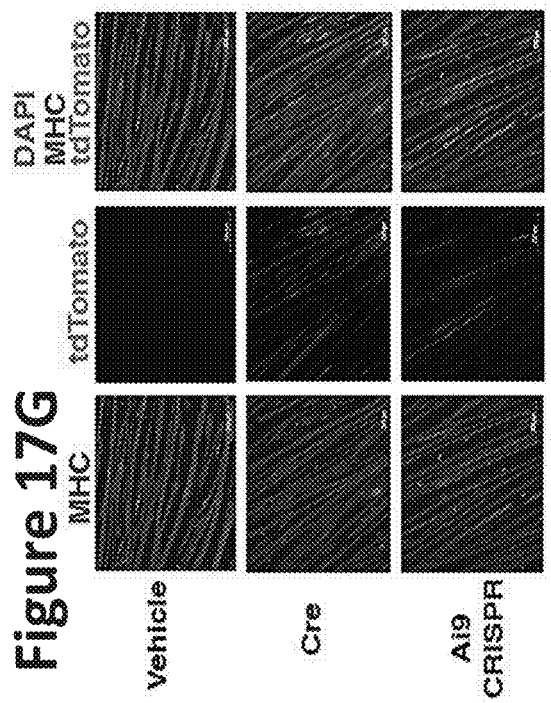
FIG. 17G is representative immunofluorescence images of myotubes differentiated from FACSorted Pax7-ZsGreen+ cells from mice injected systemically with vehicle (top), AAV9-Cre (middle) and AAV9-Ai9 CRISPR (bottom). Myosin heavy chain (MHC, green); tdTomato (red). 1 bar: 200 um.
Figure 17F:
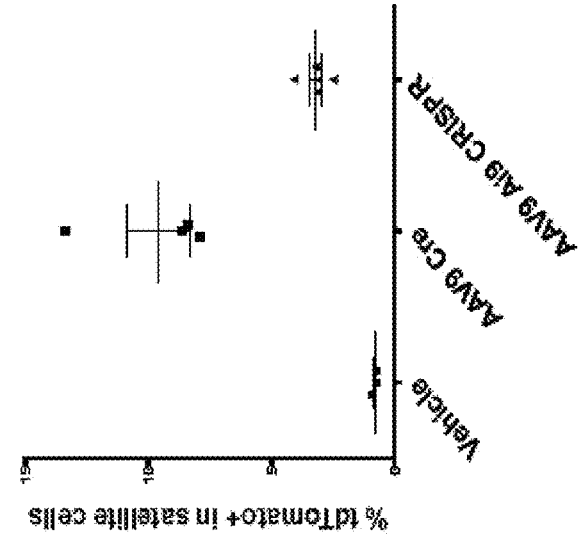
FIG. 17F graphically depicts the quantification of tdTomato+ cells among ZsGreen+ satellite cells isolated from mice injected systemically with vehicle, AAV9-Cre or AAV9-Ai9 CRISPR.

AAV9-CRISPR gene editing in satellite cells in vivo was monitored using the sensitive Ai9 fluorescent reporter system described herein. To facilitate the discrimination of satellite cells, the mdx;Ai9 mice were crossed with previously described Pax7-ZsGreen animals, in which satellite cells are specifically marked by green fluorescence. Pax7-ZsGreen$^{+/}$;Mdx;Ai9 mice were injected intramuscularly (FIG. 17B-17D) or intraperitoneally (FIG. 17E-17G,) with AAV9 encoding Cre recombinase or Ai9 CRISPR components, and skeletal muscles were harvested 2 weeks later for FACS isolation of ZsGreen+ muscle satellite cells (FIG. 17A). Flow cytometric analysis demonstrated that about 36% (+−1.9%) of Pax7-ZsGreen+ cells expressed tdTomato when isolated from muscles injected locally with AAV9-Cre (6E+11 vg), suggesting significant transduction by AAV of endogenous satellite cells in these mice (FIG. 17B, 17C). Systemic delivery of AAV9-Cre (3E+11 vg) also resulted in transduction of muscle satellite cells, albeit at lower frequencies (9.6%+/−2.6%) (FIG. 17E, 17F). Myogenic differentiation of ZsGreen+ satellite cells isolated from mice receiving either intramuscular or systemic AAV9-Cre produced tdTomato+ myotubes, demonstrating that permanent recombination at the Ai9 locus was induced in these muscle progenitors by AAV9-Cre. (FIGS. 17D and 17G).

TdTomato expression was also detected in Pax7-ZsGreen+ satellite cells harvested from mice receiving AAV9-SaCas9+AAV9-Ai9 gRNAs intramuscularly (FIG. 17B, 17C) or intraperitoneally (FIG. 17E, 17F) with efficiency of ~3%. These CRISPR-targeted satellite cells also differentiated to produce tdTomato+ myotubes (FIGS. 17D and 17G), again consistent with stable modification of the Ai9 allele following in vivo exposure to Ai9-CRISPR.

EXAMPLE XVIII

Permanent Genetic Modification of Cells Derived from Satellite Cells

Methods described herein are directed to in vivo administration of a Cas9/guide RNA system as described herein to an animal sufficient to introduce the Cas9/guide RNA system to in vivo produced satellite cells and wherein the Cas9/guide RNA system edits the target gene in the satellite cell and wherein the genetically modified satellite cell differentiates into a muscle cell that has retained the genetic modification. According to certain aspects, methods described herein use a Cas9/guide RNA system to transduce and genomically modify endogenous satellite cells. The genomically modify endogenous satellite cells differentiate into muscle cells with the genetic modification. According to certain aspects, methods described herein use a Cas9/guide RNA system targeting Dmd to transduce and genomically modify endogenous satellite cells which are precursor cells in dystrophic muscles, and wherein the transformed satellite cells diferentiate into muscle cells with the genetically altered Dmd. According to certain aspects, methods are provided for in situ gene editing in muscle satellite cells as well as terminally differentiated multinucleated fibers.

Myosatellite cells or satellite cells are small mononuclear multipotent cells with virtually no cytoplasm found in mature muscle. Satellite cells are precursors to skeletal muscle cells, able to give rise to satellite cells or differentiated skeletal muscle cells. They have the potential to provide additional myonuclei to their parent muscle fiber, or return to a quiescent state. More specifically, upon activation, satellite cells can re-enter the cell cycle to proliferate and differentiate into myoblasts.

Myosatellite cells are located between the basement membrane and the sarcolemma of muscle fibers, and can lie in grooves either parallel or transversely to the longitudinal axis of the fibre. Their distribution across the fibre can vary significantly. Non-proliferative, quiescent myosatellite cells, which adjoin resting skeletal muscles, can be identified by their distinct location between sarcolemma and basal lamina, a high nuclear-to-cytoplasmic volume ratio, few organelles (e.g. ribosomes, endoplasmic reticulum, mitochondria, golgi complexes), small nuclear size, and a large quantity of nuclear heterochromatin relative to myonuclei. On the other hand, activated satellite cells have an increased number of caveolae, cytoplasmic organelles, and decreased levels of heterochromatin. Satellite cells are able to differentiate and fuse to augment existing muscle fibers and to form new fibers. These cells represent the oldest known adult stem cell niche, and are involved in the normal growth of muscle, as well as regeneration following injury or disease. In undamaged muscle, the majority of satellite cells are quiescent; they neither differentiate nor undergo cell division. In response to mechanical strain, satellite cells become activated. Activated satellite cells initially proliferate as skeletal myoblasts before undergoing myogenic differentiation.

Figure 17H:
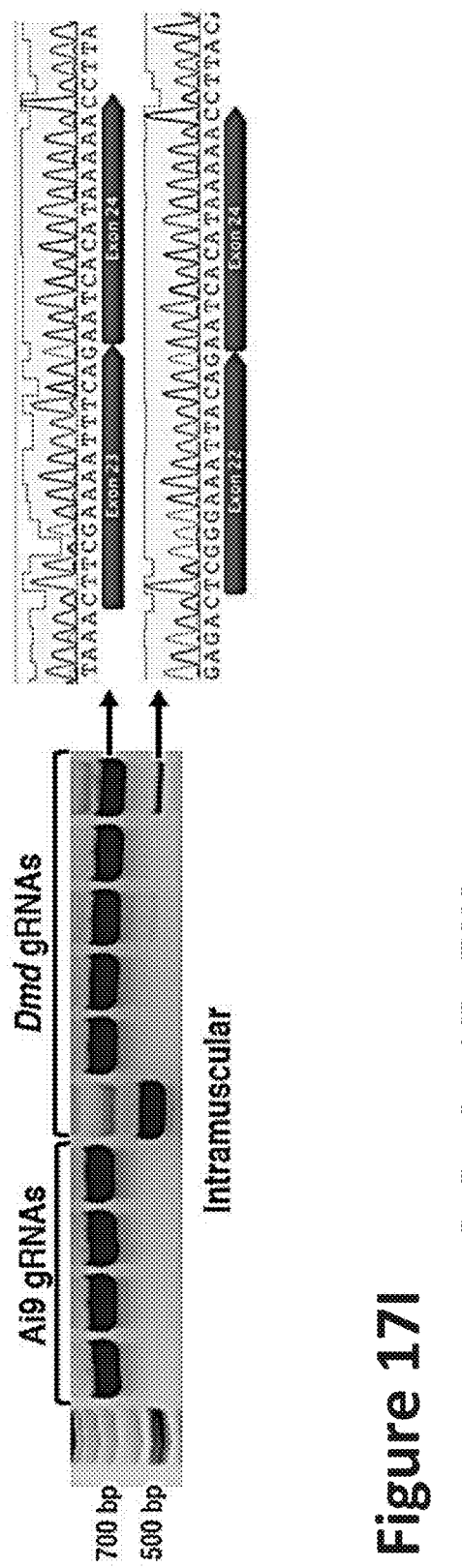
FIG. 17H illustrates RT-PCR with exon23 spanning primers indicates expression of exon 23-skipped DMD mRNA in myotubes differentiated in vitro from satellite cells isolated from adult mice receiving AAV-DMD CRISPR (right lanes), but not those from muscles injected with AAV-Ai9 CRISPR (left lanes) after intramuscular delivery of AAVs. Sequencing result from unedited and exon skipped mRNA, confirms skipping of exon 23 in the mRNA. (SEQ ID NO:7-8)
Figure 17I:
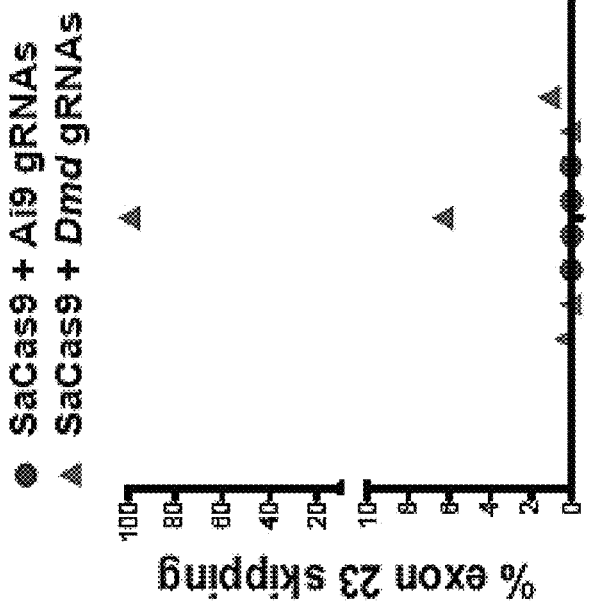
FIG. 17I graphically depicts quantification of exon skipping in myotubes derived from satellite cells isolated from intramuscularly injected muscles by Taqman assay.
Figure 17J:
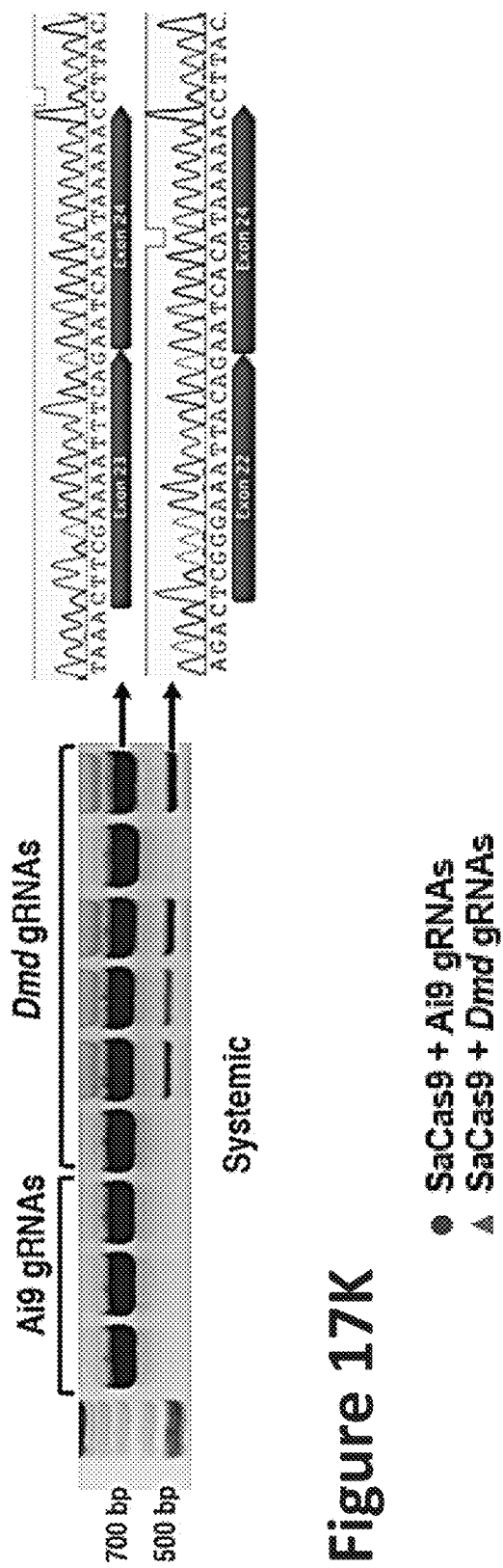
FIG. 17J illustrates RT-PCR with exon 23 spanning primers indicates expression of exon 23-skipped DMD mRNA in myotubes differentiated in vitro from satellite cells isolated from 3 weeks old mice receiving AAV-DMD CRISPR (right lanes), but not those from muscles injected with AAV-Ai9 CRISPR (left lanes) after systemic delivery of AAVs on P3. Sequencing result from unedited and exon skipped mRNA, confirms skipping of exon 23 in the mRNA. (SEQ ID NO:9-10)
Figure 17K:
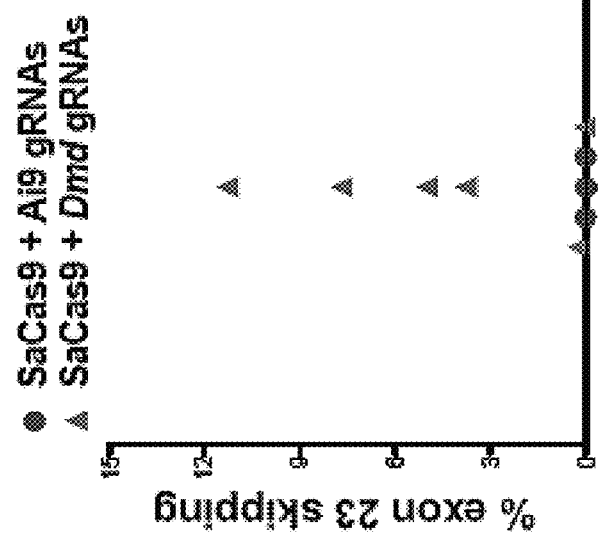
FIG. 17K graphically depicts quantification of exon skipping in myotubes derived from satellite cells isolated from systemically injected mice by Taqman assay.

Pax7-ZsGreen+ satellite cells from Pax7-ZsGreen+/−; Mdx;Ai9 mice injected intramuscularly or systemically with AAV9-SaCas9+AAV9-Dmd gRNAs or AAV9-SaCas9+ AAV9-Ai9 gRNAs were isolated and expanded and differentiated in vitro. RT-PCR analysis of mRNA isolated from satellite cell-derived myotubes demonstrated the presence of a truncated transcript of the expected size for gene-edited Dmd in many of the AAV-Dmd CRISPR injected muscles, but not AAV-Ai9 CRISPR injected ones. In addition, sequencing of this shorter transcript confirmed site directed excision of exon 23 and production of an exon-skipped mRNA in which exon 22 is fused to exon 24 (FIGS. 17H and 17J). Levels of exon-skipped transcripts in the differentiated myotubes were also quantified using Taqman-based real time PCR (FIGS. 17I and 17K).

EXAMPLE XIX

Embodiments

Aspects of the present disclosure include a method of producing an altered gene product in a eukaryotic cell including providing to the cell two or more guide RNAs and a Cas9 protein, wherein the two or more guide RNAs are complementary to two or more target genomic DNA sequences flanking a target excision sequence including one or more exons in a target gene encoding a biologically functional polypeptide, wherein the two or more guide RNAs bind to the two or more complementary target genomic DNA sequences and the Cas9 protein cleaves the two or more target genomic DNA sequences thereby removing the one or more exons from the target gene to produce an altered target gene and wherein the altered target gene recombines, and wherein the eukaryotic cell expresses the altered target gene to produce an altered biologically functional polypeptide. According to one aspect, the altered biologically functional polypeptide lacks a polypeptide sequence corresponding to the one or more removed exons. According to one aspect, the two or more guide RNAs and the Cas9 protein are foreign to the eukaryotic cell. According to one aspect, the two or more guide RNAs and the Cas9 protein are foreign to each other. According to one aspect, the two or more guide RNAs and the Cas9 protein are non-naturally occurring. According to one aspect, the two or more guide RNAs are provided to the cell by electroporation of the two or more guide RNAs into the cell. According to one aspect, the Cas9 protein is provided to the cell by electroporation of the Cas9 protein into the cell. According to one aspect, the two or more guide RNAs are provided to the cell by introducing into the cell a first foreign nucleic acid sequence encoding the two or more guide RNAs. According to one aspect, the two or more guide RNAs are provided to the cell by introducing into the cell a first foreign nucleic acid sequence encoding the two or more guide RNAs present in a plasmid or vector. According to one aspect, the Cas 9 protein is provided to the cell by introducing into the cell a second foreign nucleic acid sequence encoding the Cas 9 protein. According to one aspect, the Cas 9 protein is provided to the cell by introducing into the cell a second foreign nucleic acid sequence encoding the Cas 9 protein present in a plasmid or vector. According to one aspect, the eukaryotic cell is a yeast cell, a plant cell, a vertebrate cell, a mammalian cell or a human cell. According to one aspect, the eukaryotic cell is within a mammal. According to one aspect, the eukaryotic cell is a skeletal muscle cell. According to one aspect, the eukaryotic cell is a cardiac muscle cell. According to one aspect, the target excision sequence is greater than 45 kb. According to one aspect, the target gene encodes dystrophin protein. According to one aspect, the target gene encodes dystrophin protein and the one or more exons is exon 23. According to one aspect, the target gene encodes dystrophin protein and the one or more exons is exon 52 and exon 53. According to one aspect, the RNA includes between about 10 to about 250 nucleotides. According to one aspect, the RNA includes between about 20 to about 100 nucleotides. According to one aspect, the guide RNA includes a guide sequence fused to a trans-activating cr (tracr) sequence. According to one aspect, the ratio of plasmid encoding the Cas9 protein to the plasmid encoding the guide RNA is between 1:5 and 2:1. According to one aspect, the plasmid encoding the guide RNA is modified to increase the expression of the RNA by removing a potential premature transcription termination site. According to one aspect, the one or more exons includes a mutation. According to one aspect, the Cas9 protein is provided to the cell by electroporation of the Cas9 mRNA into the cell. According to one aspect, the guide RNA and the Cas9 protein co-localize to the target genomic DNA sequence to form a complex. According to one aspect, the target nucleic acid is chromosomal DNA. According to one aspect, the Cas9 protein is wild type Cas9, Cas9 nickase or a nuclease null Cas9 including a nuclease. According to one aspect, the guide RNA and the Cas9 protein are combined and then contacted with the target gene. According to one aspect, the guide RNA and the Cas9 protein are combined and then contacted with the target gene within a cell. According to one aspect, the method includes providing to the cell a plurality of guide RNAs with each having a portion complementary to a target genomic DNA sequence. According to one aspect, the cell is a transplantable cell. According to one aspect, the cell is a progenitor cell. According to one aspect, the cell is a stem cell. According to one aspect, the cell is a muscle stem cell.

Aspects of the present disclosure are directed to a skeletal muscle cell including a Cas9 protein and two or more guide RNAs complementary to two or more target genomic DNA sequences flanking a target excision sequence including one or more exons in a target gene encoding dystrophin protein. According to one aspect, the one or more exons are in the exon 45-55 region. According to one aspect, the one or more exons include exon 23, exon 52 or exon 53.

Aspects of the present disclosure are directed to according to a skeletal muscle cell including a first nucleic acid encoding two or more guide RNAs complementary to two or more target genomic DNA sequences flanking a target excision sequence including one or more exons in a target gene encoding dystrophin protein and a second nucleic acid encoding a Cas9 protein. According to one aspect, the one or more exons are in the exon 45-55 region. According to one aspect, the one or more exons include exon 23, exon 52 or exon 53. According to one aspect, the first nucleic acid is within a plasmid or vector. According to one aspect, the second nucleic acid is within a plasmid or vector. According to one aspect, the second nucleic acid is within a viral vector. According to one aspect, the second nucleic acid is within a viral vector selected from the group consisting of lentivirus, adenovirus, adeno-associated virus, retrovirus, herpes simplex virus, or sendai virus.

Aspects of the present disclosure are directed to a skeletal muscle cell including a Cas9 protein and two or more guide RNAs complementary to two or more target genomic DNA sequences flanking a target excision sequence including one or more exons in a target gene encoding dystrophin protein. According to one aspect, the one or more exons are in the exon 45-55 region. According to one aspect, the one or more exons include exon 23, exon 52 or exon 53.

Aspects of the present disclosure are directed to a muscle stem cell including a first nucleic acid encoding two or more guide RNAs complementary to two or more target genomic DNA sequences flanking a target excision sequence including one or more exons in a target gene encoding dystrophin protein and a second nucleic acid encoding a Cas9 protein. According to one aspect, the one or more exons are in the exon 45-55 region. According to one aspect, the one or more exons include exon 23, exon 52 or exon 53. According to one aspect, the first nucleic acid is within a plasmid or vector. According to one aspect, the second nucleic acid is within a plasmid or vector. According to one aspect, the second nucleic acid is within a viral vector. According to one aspect, the second nucleic acid is within a viral vector selected from the group consisting of lentivirus, adenovirus, adeno-associated virus, retrovirus, herpes simplex virus, or sendai virus.

Aspects of the present disclosure are directed to a genetically modified skeletal muscle cell including a first nucleic acid encoding two or more guide RNAs complementary to two or more target genomic DNA sequences flanking a target excision sequence including one or more exons in a target gene encoding dystrophin protein and a second nucleic acid encoding a Cas9 protein and wherein the target gene encoding dystrophin protein lacks one or more of exon 23, exon 52 or exon 53.

Aspects of the present disclosure are directed to a genetically modified muscle stem cell including a first nucleic acid encoding two or more guide RNAs complementary to two or more target genomic DNA sequences flanking a target excision sequence including one or more exons in a target gene encoding dystrophin protein and a second nucleic acid encoding a Cas9 protein and wherein the target gene encoding dystrophin protein lacks one or more of exon 23, exon 52 or exon 53.

Aspects of the present disclosure are directed to a method of producing an altered gene product in a eukaryotic cell within a mammal comprising injecting two plasmids into the mammal, wherein the two plasmids include a first nucleic acid encoding two or more guide RNAs complementary to two or more target genomic DNA sequences flanking a target excision sequence including one or more exons in a target gene encoding dystrophin protein and a second nucleic acid encoding a Cas9 protein, wherein the two or more guide RNAs bind to the two or more complementary target genomic DNA sequences and the Cas9 protein cleaves the two or more target genomic DNA sequences thereby removing the one or more exons from the target gene to produce an altered target gene and wherein the altered target gene recombines, and wherein the eukaryotic cell expresses the altered target gene to produce an altered biologically functional polypeptide. According to one aspect, the eukaryotic cell is a skeletal muscle cell oir cardiac cell. According to one aspect, the eukaryotic cell is a muscle stem cell or cardiac stem cell. According to one aspect, the eukaryotic cell is a member of the group consisting of a skeletal muscle cell, a muscle stem cell, a progenitor cell and a stem cell. According to one aspect, the one or more exons is exon 23, exon 52 or exon 53.

Aspects of the present disclosure are directed to a method of removing one or more mutations from a target gene encoding a dystrophin protein in a eukaryotic cell inclouding providing to the cell two or more guide RNAs and a Cas9 protein, wherein the two or more guide RNAs are complementary to two or more target genomic DNA sequences flanking a target excision sequence including one or more exons having one or more mutations in the target gene, wherein the two or more guide RNAs bind to the two or more complementary target genomic DNA sequences and the Cas9 protein cleaves the two or more target genomic DNA sequences thereby removing the one or more exons having one or more mutations from the target gene to produce an altered target gene and wherein the altered target gene recombines, and wherein the eukaryotic cell expresses the altered target gene to produce a functional truncated dystrophin protein. According to one aspect, the eukaryotic cell is a skeletal muscle cell or cardiac cell. According to one aspect, the eukaryotic cell is a muscle stem cell or cardiac stem cell. According to one aspect, the eukaryotic cell is a member of the group consisting of a skeletal muscle cell, a muscle stem cell, a progenitor cell and a stem cell. According to one aspect, the one or more exons is exon 23, exon 52 or exon 53. According to one aspect, the eukaryotic cell is within a mammal. According to one aspect, the one or more exons are in the exon 45-55 region.

SEQUENCE LISTING

```
Sequence total quantity: 34
SEQ ID NO: 1            moltype = DNA   length = 37
FEATURE                 Location/Qualifiers
misc_feature            1..37
                        note = Figure 14E intron 22 and intron 23
```

```
source                    1..37
                          mol_type = other DNA
                          organism = synthetic construct
SEQUENCE: 1
aaatataata tgccctgtcc gaggtttggc ctttaaa                              37

SEQ ID NO: 2              moltype = DNA  length = 37
FEATURE                   Location/Qualifiers
misc_feature              1..37
                          note = Figure 14G exon 23 and exon 24
source                    1..37
                          mol_type = other DNA
                          organism = synthetic construct
SEQUENCE: 2
taaacttcga aaatttcaga atcacataaa aaccta                               37

SEQ ID NO: 3              moltype = DNA  length = 37
FEATURE                   Location/Qualifiers
misc_feature              1..37
                          note = Figure 14G exon 22 and exon 24
source                    1..37
                          mol_type = other DNA
                          organism = synthetic construct
SEQUENCE: 3
gagactcggg aaattacaga atcacataaa aaccta                               37

SEQ ID NO: 4              moltype = DNA  length = 37
FEATURE                   Location/Qualifiers
misc_feature              1..37
                          note = Figure 15B Exon 23 excision in DNA
source                    1..37
                          mol_type = other DNA
                          organism = synthetic construct
SEQUENCE: 4
taatataata gaaattattt tcttggattg tctgtat                              37

SEQ ID NO: 5              moltype = DNA  length = 36
FEATURE                   Location/Qualifiers
misc_feature              1..36
                          note = Figure 15C Exon 23 excision in DNA
source                    1..36
                          mol_type = other DNA
                          organism = synthetic construct
SEQUENCE: 5
taaacttcga aaatttcaga atcacataaa aacctt                               36

SEQ ID NO: 6              moltype = DNA  length = 36
FEATURE                   Location/Qualifiers
misc_feature              1..36
                          note = Figure 15C Exon 23 excision in DNA
source                    1..36
                          mol_type = other DNA
                          organism = synthetic construct
SEQUENCE: 6
agactcggga aattacagaa tcacataaaa acctaa                               36

SEQ ID NO: 7              moltype = DNA  length = 37
FEATURE                   Location/Qualifiers
misc_feature              1..37
                          note = Figure 17H skipping of exon 23 in the mRNA
source                    1..37
                          mol_type = other DNA
                          organism = synthetic construct
SEQUENCE: 7
taaacttcga aaatttcaga atcacataaa aaccta                               37

SEQ ID NO: 8              moltype = DNA  length = 38
FEATURE                   Location/Qualifiers
misc_feature              1..38
                          note = Figure 17H skipping of exon 23 in the mRNA
source                    1..38
                          mol_type = other DNA
                          organism = synthetic construct
SEQUENCE: 8
gagactcggg aaattacaga atcacataaa aaccttac                             38

SEQ ID NO: 9              moltype = DNA  length = 38
FEATURE                   Location/Qualifiers
```

-continued

```
misc_feature               1..38
                           note = Figure 17J exon 23 and 24
source                     1..38
                           mol_type = other DNA
                           organism = synthetic construct
SEQUENCE: 9
taaacttcga aaatttcaga atcacataaa aaccttac                              38

SEQ ID NO: 10              moltype = DNA   length = 37
FEATURE                    Location/Qualifiers
misc_feature               1..37
                           note = Figure 17J exon 22 and 24
source                     1..37
                           mol_type = other DNA
                           organism = synthetic construct
SEQUENCE: 10
agactcggga aattacagaa tcacataaaa accttac                               37

Figure 18A:
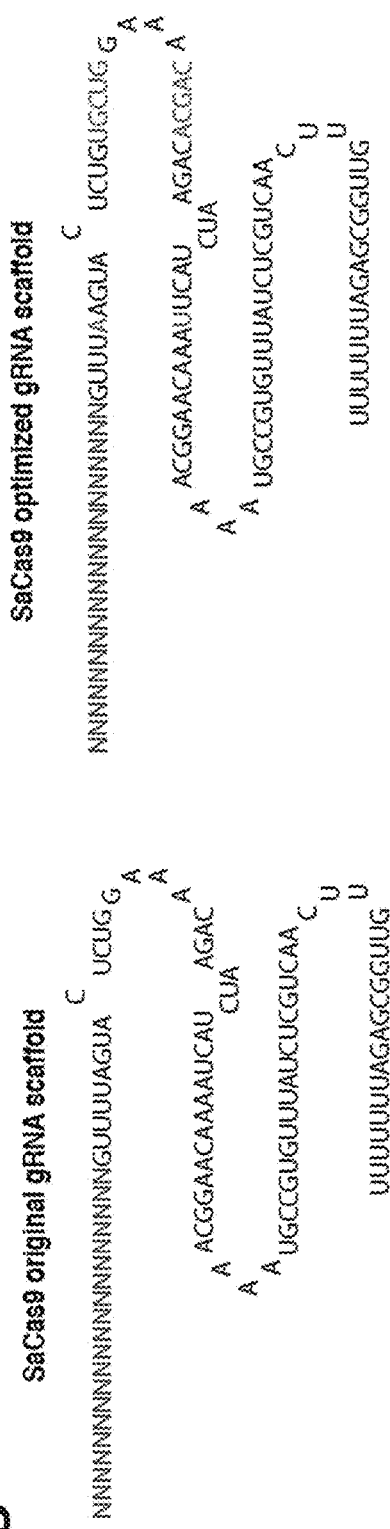
FIG. 18A schematically depicts the sequence of the original (left) and optimized (left) Sa gRNA scaffold. (SEQ ID NO:11-12)
Figure 18B:
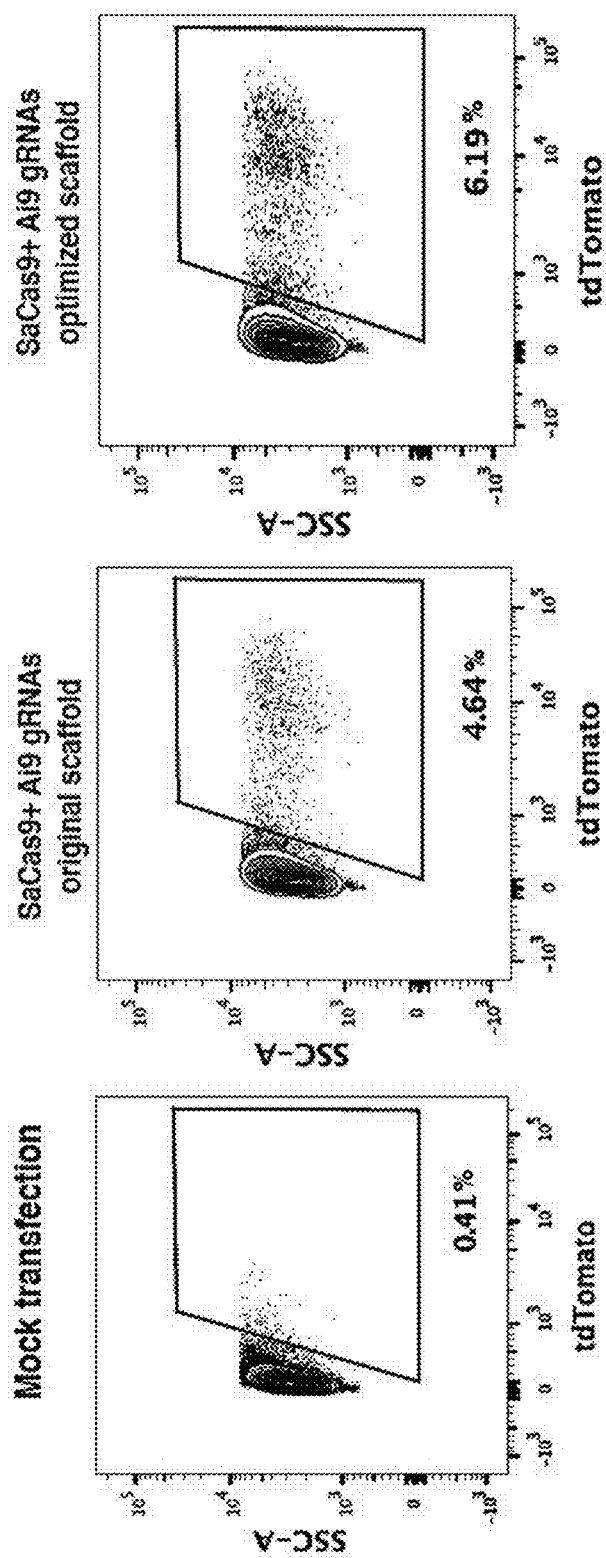
FIG. 18B illustrates the representative FACS plots from Ai9 mouse tail tip fibroblasts transfected with no plasmids (left panel), plasmids encoding SaCas9 and Ai9 gRNAs with the original scaffold (middle panel) or the optimized scaffold (right panel).
Figure 18C:
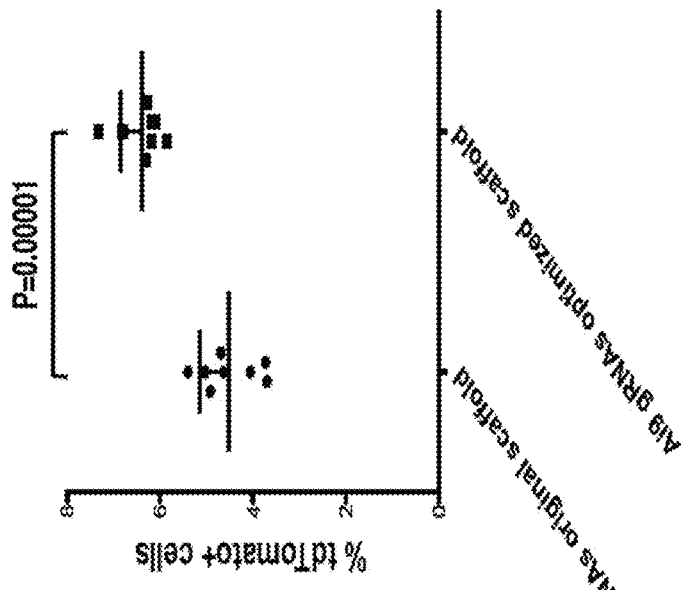
FIG. 18C graphically depicts quantification of percent tdTomato+ targeted cells in transfected Ai9 tail tip fibroblasts.
Figure 18D:
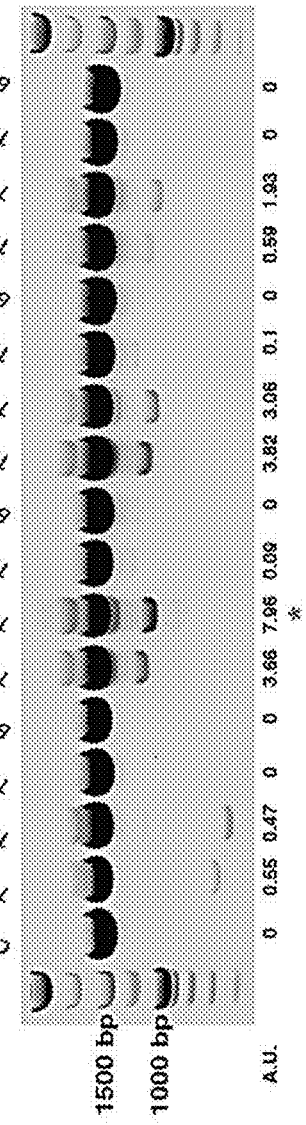
FIG. 18D is an image illustrating the result of the screening for different pairs of Sa DMD23 gRNAs by genomic PCR using primers spanning exon 23. Intensity of the cut band was quantified by densitometry. A.U.: Arbitrary Unit normalized to the wild-type band.

SEQ ID NO: 11              moltype = RNA   length = 103
FEATURE                    Location/Qualifiers
misc_feature               1..103
                           note = Figure 18A gRNA scaffold
source                     1..103
                           mol_type = other RNA
                           organism = synthetic construct
variation                  1..20
                           note = wherein n is a, c, g, t or u
SEQUENCE: 11
nnnnnnnnnn nnnnnnnnnn gttttagtac tctggaaaca gaatctacta aacaaggca       60
aaatgccgtg tttatctcgt caacttgttg gcgagatttt ttt                       103

SEQ ID NO: 12              moltype = RNA   length = 114
FEATURE                    Location/Qualifiers
misc_feature               1..114
                           note = Figure 18A gRNA scaffold
source                     1..114
                           mol_type = other RNA
                           organism = synthetic construct
variation                  1..20
                           note = wherein n is a, c, g, t or u
SEQUENCE: 12
nnnnnnnnnn nnnnnnnnnn gttttaagta ctctgtgctg gaaacagcac agaatctact      60
taaacaaggc aaaatgccgt gtttatctcg tcaacttgtt ggcgagattt tttt           114

SEQ ID NO: 13              moltype = DNA   length = 37
FEATURE                    Location/Qualifiers
misc_feature               1..37
                           note = Figure 19C exon 22 and 24
source                     1..37
                           mol_type = other DNA
                           organism = synthetic construct
SEQUENCE: 13
gagactcggg aaattacaga atcacataaa aaccta                                37

SEQ ID NO: 14              moltype = AA   length = 1368
FEATURE                    Location/Qualifiers
source                     1..1368
                           mol_type = protein
                           organism = Streptococcus pyogenes
SEQUENCE: 14
MDKKYSIGLD IGTNSVGWAV ITDEYKVPSK KFKVLGNTDR HSIKKNLIGA LLFDSGETAE       60
ATRLKRTARR RYTRRKNRIC YLQEIFSNEM AKVDDSFFHR LEESFLVEED KKHERHPIFG      120
NIVDEVAYHE KYPTIYHLRK KLVDSTDKAD LRLIYLALAH MIKFRGHFLI EGDLNPDNSD      180
VDKLFIQLVQ TYNQLFEENP INASGVDAKA ILSARLSKSR RLENLIAQLP GEKKNGLFGN      240
LIALSLGLTP NFKSNFDLAE DAKLQLSKDT YDDDLDNLLA QIGDQYADLF LAAKNLSDAI      300
LLSDILRVNT EITKAPLSAS MIKRYDEHHQ DLTLLKALVR QQLPEKYKEI FFDQSKNGYA      360
GYIDGGASQE EFYKFIKPIL EKMDGTEELL VKLNREDLLR KQRTFDNGSI PHQIHLGELH      420
AILRRQEDFY PFLKDNREKI EKILTFRIPY YVGPLARGNS RFAWMTRKSE ETITPWNFEE      480
VVDKGASAQS FIERMTNFDK NLPNEKVLPK HSLLYEYFTV YNELTKVKYV TEGMRKPAFL      540
SGEQKKAIVD LLFKTNRKVT VKQLKEDYFK KIECFDSVEI SGVEDRFNAS LGTYHDLLKI      600
IKDKDFLDNE ENEDILEDIV LTLTLFEDRE MIEERLKTYA HLFDDKVMKQ LKRRRYTGWG      660
RLSRKLINGI RDKQSGKTIL DFLKSDGFAN RNFMQLIHDD SLTFKEDIQK AQVSGQGDSL      720
HEHIANLAGS PAIKKGILQT VKVVDELVKV MGRHKPENIV IEMARENQTT QKGQKNSRER      780
MKRIEEGIKE LGSQILKEHP VENTQLQNEK LYLYYLQNGR DMYVDQELDI NRLSDYDVDH      840
IVPQSFLKDD SIDNKVLTRS DKNRGKSDNV PSEEVVKKMK NYWRQLLNAK LITQRKFDNL      900
TKAERGGLSE LDKAGFIKRQ LVETRQITKH VAQILDSRMN TKYDENDKLI REVKVITLKS      960
KLVSDFRKDF QFYKVREINN YHHAHDAYLN AVVGTALIKK YPKLESEFVY GDYKVYDVRK     1020
MIAKSEQEIG KATAKYFFYS NIMNFFKTEI TLANGEIRKR PLIETNGETG EIVWDKGRDF    1080
ATVRKVLSMP QVNIVKKTEV QTGGFSKESI LPKRNSDKLI ARKKDWDPKK YGGFDSPTVA    1140
```

```
YSVLVVAKVE KGKSKKLKSV KELLGITIME RSSFEKNPID FLEAKGYKEV KKDLIIKLPK    1200
YSLFELENGR KRMLASAGEL QKGNELALPS KYVNFLYLAS HYEKLKGSPE DNEQKQLFVE    1260
QHKHYLDEII EQISEFSKRV ILADANLDKV LSAYNKHRDK PIREQAENII HLFTLTNLGA    1320
PAAFKYFDTT IDRKRYTSTK EVLDATLIHQ SITGLYETRI DLSQLGGD                1368

SEQ ID NO: 15            moltype = DNA    length = 22
FEATURE                  Location/Qualifiers
misc_feature             1..22
                         note = gRNA
source                   1..22
                         mol_type = other DNA
                         organism = synthetic construct
SEQUENCE: 15
gaataatttc tattatatta ca                                              22

SEQ ID NO: 16            moltype = DNA    length = 22
FEATURE                  Location/Qualifiers
misc_feature             1..22
                         note = gRNA
source                   1..22
                         mol_type = other DNA
                         organism = synthetic construct
SEQUENCE: 16
ttcgaaaatt tcaggtaagc cg                                              22

SEQ ID NO: 17            moltype = DNA    length = 22
FEATURE                  Location/Qualifiers
misc_feature             1..22
                         note = gRNA
source                   1..22
                         mol_type = other DNA
                         organism = synthetic construct
SEQUENCE: 17
tcatttctaa aagtcttttg cc                                              22

SEQ ID NO: 18            moltype = DNA    length = 22
FEATURE                  Location/Qualifiers
misc_feature             1..22
                         note = gRNA
source                   1..22
                         mol_type = other DNA
                         organism = synthetic construct
SEQUENCE: 18
tttgagacac agtataggtt at                                              22

SEQ ID NO: 19            moltype = DNA    length = 115
FEATURE                  Location/Qualifiers
misc_feature             1..115
                         note = gRNA
source                   1..115
                         mol_type = other DNA
                         organism = synthetic construct
SEQUENCE: 19
gaataatttc tattatatta cagtttaaga gctatgctgg aaacagcata gcaagtttaa     60
ataaggctag tccgttatca acttgaaaaa gtggcaccga gtcggtgctt ttttt         115

SEQ ID NO: 20            moltype = DNA    length = 115
FEATURE                  Location/Qualifiers
misc_feature             1..115
                         note = gRNA
source                   1..115
                         mol_type = other DNA
                         organism = synthetic construct
SEQUENCE: 20
ttcgaaaatt tcaggtaagc cggtttaaga gctatgctgg aaacagcata gcaagtttaa     60
ataaggctag tccgttatca acttgaaaaa gtggcaccga gtcggtgctt ttttt         115

SEQ ID NO: 21            moltype = DNA    length = 115
FEATURE                  Location/Qualifiers
misc_feature             1..115
                         note = gRNA
source                   1..115
                         mol_type = other DNA
                         organism = synthetic construct
SEQUENCE: 21
tcatttctaa aagtcttttg ccgtttaaga gctatgctgg aaacagcata gcaagtttaa     60
ataaggctag tccgttatca acttgaaaaa gtggcaccga gtcggtgctt ttttt         115

SEQ ID NO: 22            moltype = DNA    length = 115
```

```
FEATURE                 Location/Qualifiers
misc_feature            1..115
                        note = gRNA
source                  1..115
                        mol_type = other DNA
                        organism = synthetic construct
SEQUENCE: 22
tttgagacac agtataggtt atgtttaaga gctatgctgg aaacagcata gcaagtttaa    60
ataaggctag tccgttatca acttgaaaaa gtggcaccga gtcggtgctt ttttt       115

SEQ ID NO: 23           moltype = AA   length = 1395
FEATURE                 Location/Qualifiers
REGION                  1..1395
                        note = Cas9 protein with NLS
source                  1..1395
                        mol_type = protein
                        organism = synthetic construct
SEQUENCE: 23
MDKKYSIGLD IGTNSVGWAV ITDEYKVPSK KFKVLGNTDR HSIKKNLIGA LLFDSGETAE    60
ATRLKRTARR RYTRRKNRIC YLQEIFSNEM AKVDDSFFHR LEESFLVEED KKHERHPIFG   120
NIVDEVAYHE KYPTIYHLRK KLVDSTDKAD LRLIYLALAH MIKFRGHFLI EGDLNPDNSD   180
VDKLFIQLVQ TYNQLFEENP INASGVDAKA ILSARLSKSR RLENLIAQLP GEKKNGLFGN   240
LIALSLGLTP NFKSNFDLAE DAKLQLSKDT YDDDLDNLLA QIGDQYADLF LAAKNLSDAI   300
LLSDILRVNT EITKAPLSAS MIKRYDEHHQ DLTLLKALVR QQLPEKYKEI FFDQSKNGYA   360
GYIDGGASQE EFYKFIKPIL EKMDGTEELL VKLNREDLLR KQRTFDNGSI PHQIHLGELH   420
AILRRQEDFY PFLKDNREKI EKILTFRIPY YVGPLARGNS RFAWMTRKSE ETITPWNFEE   480
VVDKGASAQS FIERMTNFDK NLPNEKVLPK HSLLYEYFTV YNELTKVKYV TEGMRKPAFL   540
SGEQKKAIVD LLFKTNRKVT VKQLKEDYFK KIECFDSVEI SGVEDRFNAS LGTYHDLLKI   600
IKDKDFLDNE ENEDILEDIV LTLTLFEDRE MIEERLKTYA HLFDDKVMKQ LKRRRYTGWG   660
RLSRKLINGI RDKQSGKTIL DFLKSDGFAN RNFMQLIHDD SLTFKEDIQK AQVSGQGDSL   720
HEHIANLAGS PAIKKGILQT VKVVDELVKV MGRHKPENIV IEMARENQTT QKGQKNSRER   780
MKRIEEGIKE LGSQILKEHP VENTQLQNEK LYLYYLQNGR DMYVDQELDI NRLSDYDVDH   840
IVPQSFLKDD SIDNKVLTRS DKNRGKSDNV PSEEVVKKMK NYWRQLLNAK LITQRKFDNL   900
TKAERGGLSE LDKAGFIKRQ LVETRQITKH VAQILDSRMN TKYDENDKLI REVKVITLKS   960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGDSR ADPKKKRKVD  1380
PKKKRKVDPK KKRKV                                                 1395

SEQ ID NO: 24           moltype = DNA   length = 40
FEATURE                 Location/Qualifiers
misc_feature            1..40
                        note = Spacer sequence
source                  1..40
                        mol_type = other DNA
                        organism = synthetic construct
SEQUENCE: 24
gggccatgtg gacatccatg aggtgagaca gtgccagcgt                          40

SEQ ID NO: 25           moltype = DNA   length = 37
FEATURE                 Location/Qualifiers
misc_feature            1..37
                        note = Spacer sequence
source                  1..37
                        mol_type = other DNA
                        organism = synthetic construct
SEQUENCE: 25
ggcctgaagc cactacagct gctggagatc aaggctc                             37

SEQ ID NO: 26           moltype = DNA   length = 38
FEATURE                 Location/Qualifiers
misc_feature            1..38
                        note = Spacer sequence
source                  1..38
                        mol_type = other DNA
                        organism = synthetic construct
SEQUENCE: 26
ggcctgaagc cactacagct gctggagatc aaggctcg                            38

SEQ ID NO: 27           moltype = DNA   length = 30
FEATURE                 Location/Qualifiers
misc_feature            1..30
                        note = Spacer sequence
```

```
source                      1..30
                            mol_type = other DNA
                            organism = synthetic construct
SEQUENCE: 27
gccattgcag ctgttagaag tgaaagcaag                                            30

SEQ ID NO: 28               moltype = DNA   length = 27
FEATURE                     Location/Qualifiers
misc_feature                1..27
                            note = Spacer sequence
source                      1..27
                            mol_type = other DNA
                            organism = synthetic construct
SEQUENCE: 28
ggccctagca tctaagttct cgcaggc                                               27

SEQ ID NO: 29               moltype = DNA   length = 35
FEATURE                     Location/Qualifiers
misc_feature                1..35
                            note = Spacer sequence
source                      1..35
                            mol_type = other DNA
                            organism = synthetic construct
SEQUENCE: 29
ggtcattcca tctcagctgt gacagcagcg cagaa                                      35

SEQ ID NO: 30               moltype = DNA   length = 34
FEATURE                     Location/Qualifiers
misc_feature                1..34
                            note = Spacer sequence
source                      1..34
                            mol_type = other DNA
                            organism = synthetic construct
SEQUENCE: 30
ggaagtcaag gtgacagaca cacccaagag gtcc                                       34

SEQ ID NO: 31               moltype = DNA   length = 31
FEATURE                     Location/Qualifiers
misc_feature                1..31
                            note = Spacer sequence
source                      1..31
                            mol_type = other DNA
                            organism = synthetic construct
SEQUENCE: 31
ggacacaccc aagaggtccc ggagagactt t                                          31

SEQ ID NO: 32               moltype = DNA   length = 30
FEATURE                     Location/Qualifiers
misc_feature                1..30
                            note = Spacer sequence
source                      1..30
                            mol_type = other DNA
                            organism = synthetic construct
SEQUENCE: 32
gtcaagccca aagtctctcc gggacctctt                                            30

SEQ ID NO: 33               moltype = DNA   length = 29
FEATURE                     Location/Qualifiers
misc_feature                1..29
                            note = Spacer sequence
source                      1..29
                            mol_type = other DNA
                            organism = synthetic construct
SEQUENCE: 33
ggaatcccgg tgctgccgct accccctca                                             29

SEQ ID NO: 34               moltype = DNA   length = 83
FEATURE                     Location/Qualifiers
misc_feature                1..83
                            note = Scaffold sequence
source                      1..83
                            mol_type = other DNA
                            organism = synthetic construct
SEQUENCE: 34
gttttagagc tagaaatagc aagttaaaat aaggctagtc cgttatcaac ttgaaaaagt           60
ggcaccgagt cggtgctttt ttt                                                   83
```

The invention claimed is:

1. A method of producing an altered dystrophin gene product in a eukaryotic cell within a mammal comprising
providing to the eukaryotic cell one or more nucleic acid molecules encoding two or more guide RNAs complementary to two or more target genomic dystrophin DNA sequences flanking one or more exons of exons 45-55 of a target dystrophin gene, and
wherein the one or more nucleic acid molecules encode a Cas9 protein,
wherein the one or more nucleic acid molecules are expressed in the eukaryotic cell,
wherein the two or more guide RNAs bind to the two or more sequences on the target dystrophin gene and the Cas9 protein cleaves at the two or more sequences thereby removing the one or more exons from the target dystrophin gene to produce an altered dystrophin gene,
wherein the two or more guide RNAs are each a tracrRNA-crRNA fusion comprising (SEQ ID NO: 12)
NNNNNNNNNNNNNNNNNNNNNNNGUUUAAGUACUCUGUGCUGGAAACAGCACA

GAAUCUACUUAAACAAGGCAAAAUGCCGUGUUUAUCUCGUCAACUUGUUG

GCGAGAUUUUUUU,
and
wherein the eukaryotic cell expresses the altered dystrophin gene to produce a truncated dystrophin polypeptide.

2. The method of claim 1, wherein the eukaryotic cell is a skeletal muscle cell.

3. The method of claim 1, wherein the eukaryotic cell is a skeletal muscle cell, a muscle stem cell, a progenitor cell or a stem cell.

4. The method of claim 1, wherein the two or more target genomic dystrophin DNA sequences flank exon 52 and exon 53.

5. The method of claim 1 wherein the one or more nucleic acid molecules are encapsulated within a viral vector.

6. The method of claim 5 wherein the viral vector is a member selected from the group consisting of lentivirus, adenovirus, adeno-associated virus, retrovirus, herpes simplex virus, and sendai virus.

7. The method of claim 1 wherein the two or more sequences are within intron 51 and intron 53.

8. The method of claim 1 wherein the one or more nucleic acid molecules are encapsulated within a liposome.

9. The method of claim 1 wherein the eukaryotic cell produces mRNA skipping exon 52 and exon 53 and wherein exon 51 is fused directly to exon 54.

10. A method of removing one or more mutations from a target dystrophin gene in a eukaryotic cell comprising
providing to the cell two or more guide RNAs and a Cas9 protein,
wherein the two or more guide RNAs bind to two or more sequences of the target dystrophin gene,
wherein the two or more sequences flank one or more exons of exons 45-55 in the target dystrophin gene,
wherein the Cas9 protein cleaves at the two or more sequences thereby removing the one or more exons to produce an altered target dystrophin gene,
wherein the two or more guide RNAs are each a tracrRNA-crRNA fusion comprising (SEQ ID NO: 12)
NNNNNNNNNNNNNNNNNNNNNNNGUUUAAGUACUCUGUGCUGGAAACAGCACA

GAAUCUACUUAAACAAGGCAAAAUGCCGUGUUUAUCUCGUCAACUUGUUG

GCGAGAUUUUUUU,
and
wherein the eukaryotic cell expresses the altered target dystrophin gene to produce a truncated dystrophin protein.

11. The method of claim 10 wherein the eukaryotic cell is a skeletal muscle cell.

12. The method of claim 10 wherein the eukaryotic cell is a skeletal muscle cell, a muscle stem cell, a progenitor cell or a stem cell.

13. The method of claim 10, wherein the two or more target genomic dystrophin DNA sequences flank exon 52 and exon 53.

14. The method of claim 10 wherein the eukaryotic cell is within a mammal.

15. The method of claim 10 wherein the two or more sequences of the target dystrophin gene are within intron 51 and intron 53.

16. The method of claim 10 wherein the eukaryotic cell produces mRNA skipping exon 52 and exon 53 and wherein exon 51 is fused directly to exon 54.

* * * * *